United States Patent
Nittoli

(10) Patent No.: US 12,378,258 B2
(45) Date of Patent: Aug. 5, 2025

(54) BIOLOGICALLY ACTIVE MOLECULES, CONJUGATES THEREOF, AND THERAPEUTIC USES

(71) Applicant: REGENERON PHARMACEUTICALS, INC., Tarrytown, NY (US)

(72) Inventor: Thomas Nittoli, Pearl River, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 543 days.

(21) Appl. No.: 17/733,974

(22) Filed: Apr. 29, 2022

(65) Prior Publication Data

US 2022/0332729 A1    Oct. 20, 2022

Related U.S. Application Data

(62) Division of application No. 16/740,312, filed on Jan. 10, 2020, now Pat. No. 11,345,715, which is a
(Continued)

(51) Int. Cl.
| | |
|---|---|
| *C07D 507/00* | (2006.01) |
| *A61K 31/5365* | (2006.01) |
| *A61K 47/68* | (2017.01) |

(52) U.S. Cl.
CPC ........ *C07D 507/00* (2013.01); *A61K 31/5365* (2013.01); *A61K 47/68033* (2023.08);
(Continued)

(58) Field of Classification Search
None
See application file for complete search history.

(56) References Cited

U.S. PATENT DOCUMENTS

| | | |
|---|---|---|
| 4,260,608 A | 4/1981 | Miyashita et al. |
| 4,361,650 A | 11/1982 | Asai et al. |
| | (Continued) | |

FOREIGN PATENT DOCUMENTS

| | | |
|---|---|---|
| CN | 103 254 311 A | 8/2013 |
| EP | 0 425 235 A2 | 5/1991 |
| | (Continued) | |

OTHER PUBLICATIONS

Database Caplus Chemical Abstracts Service, Columbus, Ohio, US; Database Registry No. 1375089-51-2, Maytansine, N2'-deacetyl-N2'-[2-[(2-mercaptoacetyl)amino]acetyl], entered Jun. 4, 2012 (Year: 2012).*

(Continued)

*Primary Examiner* — Karl J Puttlitz
(74) *Attorney, Agent, or Firm* — FisherBroyles, LLP; Cara L. Crowley-Weber; Liang Zeng Yan

(57) ABSTRACT

The present disclosure relates to linker compounds that are useful in covalently linking biologically active molecules with Ligands. The disclosed compounds also relate to biologically active molecules and Ligand conjugates, wherein the biologically active molecule is linked to the Ligand through a linker. The disclosure further provides compositions comprising biologically active molecule-ligand conjugates, methods of modifying abnormal cell growth and methods of treatment using the conjugates or the compositions.

12 Claims, 10 Drawing Sheets

Specification includes a Sequence Listing.

Related U.S. Application Data division of application No. 14/776,668, filed as application No. PCT/US2014/029757 on Mar. 14, 2014, now Pat. No. 10,570,151.

(60) Provisional application No. 61/792,216, filed on Mar. 15, 2013.

(52) U.S. Cl.
CPC ...... *A61K 47/6849* (2017.08); *A61K 47/6855* (2017.08); *A61K 47/6869* (2017.08); *A61K 47/6871* (2017.08)

(56) References Cited

U.S. PATENT DOCUMENTS

| | | |
|---|---|---|
| 5,208,020 A | 5/1993 | Chari et al. |
| 5,714,586 A | 2/1998 | Kunstmann et al. |
| 6,596,541 B2 | 7/2003 | Murphy et al. |
| 7,595,292 B2 | 9/2009 | Brocchini et al. |
| 7,750,116 B1 | 7/2010 | Doronina et al. |
| 7,939,630 B2 | 5/2011 | Brocchini et al. |
| 8,816,051 B2 | 8/2014 | Brocchini et al. |
| 8,877,706 B2 | 11/2014 | Li et al. |
| 8,889,855 B2 | 11/2014 | Deng |
| 9,005,598 B2 | 4/2015 | Godwin et al. |
| 9,950,076 B2 | 4/2018 | Nittoli et al. |
| 9,951,141 B2 | 4/2018 | Nittoli et al. |
| 10,463,749 B2 | 11/2019 | Nittoli et al. |
| 10,570,151 B2 | 2/2020 | Nittoli |
| 10,772,972 B2 | 9/2020 | Rudge et al. |
| 2004/0235840 A1 | 11/2004 | Chari et al. |
| 2005/0169933 A1 | 8/2005 | Steeves et al. |
| 2007/0258987 A1 | 11/2007 | Francisco et al. |
| 2008/0171040 A1 | 7/2008 | Ebens et al. |
| 2008/0305044 A1 | 12/2008 | McDonagh et al. |
| 2008/0305497 A1 | 12/2008 | Kosmeder et al. |
| 2009/0068178 A1 | 3/2009 | Crowley et al. |
| 2009/0280056 A1 | 11/2009 | Dennis et al. |
| 2010/0129314 A1 | 5/2010 | Singh et al. |
| 2011/0250133 A1 | 10/2011 | Lattuada et al. |
| 2012/0058892 A1 | 3/2012 | Braun et al. |
| 2012/0096572 A1 | 4/2012 | Macdonald et al. |
| 2012/0276124 A1 | 11/2012 | Bouchard et al. |
| 2013/0029900 A1 | 1/2013 | Widdison |
| 2013/0039900 A1 | 2/2013 | Sunahara et al. |
| 2013/0101546 A1 | 4/2013 | Yurkovetskiy et al. |
| 2014/0178415 A1 | 6/2014 | Li et al. |
| 2014/0179917 A1 | 6/2014 | Deng |
| 2014/0363454 A1 | 12/2014 | Jackson et al. |
| 2014/0369960 A1 | 12/2014 | Brocchini et al. |
| 2015/0056222 A1 | 2/2015 | Papadopoulos et al. |
| 2015/0125473 A1 | 5/2015 | Burt et al. |
| 2015/0157736 A1 | 6/2015 | Rabuka et al. |
| 2015/0216994 A1 | 8/2015 | Godwin et al. |
| 2015/0283259 A1 | 10/2015 | Buet et al. |
| 2016/0058882 A1 | 3/2016 | Chari et al. |
| 2016/0354482 A1 | 12/2016 | Nittoli et al. |
| 2016/0375147 A1 | 12/2016 | Nittoli |
| 2017/0121413 A1 | 5/2017 | Nittoli et al. |
| 2017/0209591 A1 | 7/2017 | Nittoli et al. |
| 2018/0289834 A1 | 10/2018 | Nittoli et al. |
| 2018/0312597 A1 | 11/2018 | Nittoli et al. |
| 2019/0151323 A1 | 5/2019 | Nittoli et al. |
| 2020/0121806 A1 | 4/2020 | Nittoli et al. |
| 2021/0087272 A1 | 3/2021 | Kuhnert et al. |

FOREIGN PATENT DOCUMENTS

| | | |
|---|---|---|
| WO | WO 02/094325 A2 | 11/2002 |
| WO | WO 2005/010151 A2 | 2/2005 |
| WO | WO 2005/089808 | 9/2005 |
| WO | WO 2006/062779 A2 | 6/2006 |
| WO | WO 2008/122039 | 10/2008 |
| WO | WO 2008/141044 A2 | 11/2008 |
| WO | WO 2009/117277 A2 | 9/2009 |
| WO | WO 2010/010324 | 1/2010 |
| WO | WO 2010/126551 A1 | 4/2010 |
| WO | WO 2011/018611 | 2/2011 |
| WO | WO 2011/039724 A1 | 4/2011 |
| WO | WO 2011/130598 | 10/2011 |
| WO | WO 2012/005982 A1 | 1/2012 |
| WO | WO 2012/058592 A2 | 5/2012 |
| WO | WO 2012/061590 A1 | 5/2012 |
| WO | WO 2012/156918 A1 | 11/2012 |
| WO | WO 2012/166559 | 12/2012 |
| WO | WO 2012/177837 A2 | 12/2012 |
| WO | WO 2013/053872 | 4/2013 |
| WO | WO 2013/053873 | 4/2013 |
| WO | WO 2013/055990 | 4/2013 |
| WO | WO 2013/055993 | 4/2013 |
| WO | WO 2013/068874 | 4/2013 |
| WO | WO 2013/085925 A1 | 6/2013 |
| WO | WO 2013/190272 A1 | 12/2013 |
| WO | WO 2013/190292 A2 | 12/2013 |
| WO | WO 2014/064424 A1 | 5/2014 |
| WO | WO 2014/065661 | 5/2014 |
| WO | WO 2014/080251 | 5/2014 |
| WO | WO 2014/089335 A2 | 6/2014 |
| WO | WO 2014/145090 | 9/2014 |
| WO | WO 2014/194030 A2 | 12/2014 |
| WO | WO 2014/197849 A2 | 12/2014 |
| WO | WO 2014/197854 | 12/2014 |
| WO | WO 2014/197866 A1 | 12/2014 |
| WO | WO 2015/081281 A1 | 6/2015 |
| WO | WO 2015/081282 A1 | 6/2015 |
| WO | WO 2015/081857 | 6/2015 |

OTHER PUBLICATIONS

Agarwal et al., "A Pictet-Spengler ligation for Protein Chemical Modification", Proc. NatL Acad. Sci., Jan. 2, 2013, vol. 110, No. 1, pp. 46-51.

Akcakanat et al., "Heterogeneous expression of GAGE, NY-ESO-1, MAGE-A and SSX proteins in esophageal cancer: Implications for immunotherapy", Int. J. Cancer, 2006, vol. 118, pp. 123-128.

Auclair et al., "Strategies for stabilizing superoxide dismutase (SOD1), the protein destabilized in the most common form of familial amyotrophic lateral sclerosis", PNAS, Dec. 14, 2010, vol. 107, No. 50, pp. 21394-21399; www.pnas.org/cgi/doi/10.1073/pnas.1015463107.

Badescu et al., "Bridging Disulfides for Stable and Defined Antibody Drug Conjugates", Bioconjugate Chemistry, May 3, 2014, vol. 25, No. 6, pp. 1124-1136, XP055165403.

Badescu, George: Director Scientific Affairs—Bioconjugation & Protein Engineering, "Producing Better ADCs Using ThioBridge™ Conjugation", ABZENA—Enabling better biopharmaceuticals, World ADC Summit of Oct. 27, 2014, San Diego, 29 pages.

Brocchini et al., "PEGylation of native disulfide bonds in proteins", Nature Protocols, 2006, vol. 1, No. 5, pp. 2241-2252.

Carrico et al., Introducing Genetically Encoded Aldehydes into Proteins, *Nature Chemical Biology*, Jun. 2007, vol. 3, No. 6, pp. 321-322.

Davis et al., "In Vitro Characterization of the Drug-Drug Interaction Potential of Catabolites of Antibody-Maytansinoid Conjugates", Drug Metabolism and Disposition, Jun. 2012, vol. 40, No. 10, pp. 1927-1934.

Del Rosario et al., "Sulfhydryl Site-Specific Cross-Linking and Labeling of Monoclonal Antibodies by a Fluorescent Equilibrium Transfer Alkylation Cross-Link Reagent", *Bioconjugate Chemistry*, 1990, vol. 1, No. 1, pp. 51-59, XP002313938.

Dennler et al., "Transglutaminase-Based Chemo-Enzymatic Conjugation Approach Yields Homogeneous Antibody-Drug Conjugates", Bioconjugate Chemistry, 2014, vol. 25, pp. 569-578.

Doronina et al., "Development of potent monoclonal antibody aurostatin conjugates for cancer therapy," Nat. Biotech., 2003, vol. 21, No. 7, pp. 778-785.

Doronina et al., "Enhanced Activity of Monomethylauristatin F through Monoclonal Antibody Delivery: Effects of Linker Technology on Efficacy and Toxicity", Bioconjugate Chem, 2006, vol. 17, pp. 114-124.

(56) References Cited

OTHER PUBLICATIONS

Dubowchik et al., "Cathepsin b-labile dipeptide linkers for lysosomal release of doxorubicin from internalizing immunoconjugates: model studies of enzymatic drug release and antigen specific in vitro anticancer activity." Bioconjugate Chem., (2002) vol. 13, pp. 855-869.
Erickson, Hans et al., "Antibody-Maytansinoid Conjugates are Activated In Targeted Cancer Cells by Lysosomal Degradation and Linker-Dependent Intracellular Processing"; Cancer Research, American Association for Cancer Research, US; Apr. 15, 2006; vol. 66, No. 8, pp. 4426-4433, XP008074767.
Fishkin et al., "A novel pathway for maytansinoid release from thioether linked antibody-drug conjugates (ADCs) under oxidative conditions"; Chemical Communications; Jan. 1, 2011; vol. 47, No. 38, p. 10752; XP055152687.
Gondi et al., "Cathepsin B as a cancer target", Expert Opinion on Therapeutic Targets, 2013, vol. 17, No. 3, pp. 281-291, DOI: 10.1517/14728222.2013.740461.
Grumbach et al., "Hydrophilic Interaction Chromatography Using Silica Colums for the Retention of Polar Analytes and Enhanced ESI-S Sensitivity", LCGC, North America 2004, An Advanstar Publication, ID No. 7200001048EN.
Hofer et al., "An Engineered Selenocysteine Defines a Unique Class of Antibody Derivatives", Proc. Natl. Acad. Sci., Aug. 26, 2008, vol. 105, No. 34, pp. 12451-12456.
Hollander et al., "Selection of Reaction Additives Used in the Preparation of Monomeric Antibody-Calicheamicin Conjugates", Bioconjugate Chemistry, 2008, vol. 19, pp. 358-361.
International Search Report and Written Opinion mailed Aug. 28, 2014, for PCT/US2014/29757, 13 pages.
International Search Report and Written Opinion of PCT/US2014/052757 mailed Nov. 28, 2014, 13 pages.
International Search Report and Written Opinion of PCT/US2015/033618 mailed 21December 2015, 20 pages.
International Search Report and Written Opinion of PCT/US2017/014782 mailed Mar. 20, 2017, 13 pages.
Invitation together with the Search Report and Written Opinion issued by the Singapore Patent office mailed on Aug. 10, 2016, for the Singapore patent application No. 11201507481W; 11 pages.
J. A. Davis et al., "In Vitro Characterization of the Drug-Drug Interaction Potential of Catabolites of Antibody-Maytansinoid Conjugates", Drug Metabolism And Disposition, Jun. 2012, 40:10; pp. 1927-1934.
J. A. Reddy et al., Folate Receptor-Specific Antitumor Activity of EC131, a Folate-Maytansinoid Conjugate, Cancer Research, Jul. 1, 2007; vol. 67, No. 12; pp. 6376-6382.
Kawai et al., "Chemical Modification of Ansamitocins 3. Synthesis and Biological Effects of 3 Acyl Esters of Maytansinol", Chemical and Pharmaceutical Bulletin, Pharmaceutical Society of Japan, vol. 32, No. 9, Jan. 1, 1984, pp. 3441-3451, XP008094318.
Phillips et al., "Targeting HER2-Positive Breast Cancer with Trastuzumab-DM1, an Antibody-Cytotoxic Drug Conjugate", Cancer Research, 2008, No. 62, p. 9280-9290. http://cancerres.aacrjournals.org/content/68/22/9280.full-text.pdf.
Pillow et al., "Site-Specific Trastuzumab Maytansinoid Antibody-Drug Conjugates with Improved Therapeutic Activity through Linker and Antibody Engineering", Journal of Medicinal Chemistry, Oct. 9, 2014, vol. 57, No. 19, pp. 7890-7899, XP055268691.
Rabuka et al., "Site-Specific Chemical Protein Conjugation Using Genetically Encoded Aldehyde Tags", Nat. Protocols, Dec. 1, 2012, vol. 7, No. 6, pp. 1052-1067.
Ryan et al., "Polyclonal Antibody Production Against Chito-Oligosaccharides", Food and Agricultural Immunology, 2001, vol. 13, pp. 127-130.
S. C. Jeffrey et al., "Dipeptide-Based Highly Potent Doxorubicin Antibody Conjugates," Bioorganic & Medicinal Chemistry Letters, 2006, vol. 16, pp. 358-362.
Salomon et al., "Sensitive ELISA Method for the Measurement of Catabolites of Antibody-Drug Conjugates (ADCs) in Target Cancer Cells", Molecular Pharmaceutics, Jun. 1, 2015, vol. 12, No. 6, pp. 1752-1761, XP055352192.
Sapra et al., "Monoclonal antibody-based therapies in cancer: Advances and Challenges", Pharmacology & Therapeutics, 2013, vol. 138, pp. 452-469.
Satyanarayanajois et al., "Medicinal chemistry for 2020", Fut. Med. Chem., (Oct. 2011), vol. 3, No. 14, pp. 1765-1786.
Search Report and Written Opinion issued by the Singapore Patent office, mailed on Aug. 10, 2016, for the SG application No. 11201507481W; 9 pages.
Shaunak et al., "Site-specific PEGylation of Native Disulfide Bonds in Therapeutic Proteins", Nature Chemical Biology, Jun. 2006, vol. 2, No. 6, pp. 312-313.
Sun et al., "Design of Antibody-Maytansinoid Conjugates Allows for Efficient Detoxification via Liver Metabolism", Bioconjugate Chemistry, Apr. 20, 2011, vol. 22, No. 4, pp. 728-735, XP055096244.
Tang et al., "The Analysis of Key Factors Related to ADCs Structural Design", Apr. 2019, vol. 10, article 373, DOI: 10.3389/fphar.2019.00373.
Trail, "Antibody Drug Conjugates as Cancer Therapeutics", Antibodies 2013, 2, pp. 113-129; doi:10.3390/antib2010113.
Widdison et al., "Development of Anilino-Maytansinoid ADCs that Efficiently Release Cytotoxic Metabolites in Cancer Cells and Induce High Levels of Bystander Killing", Bioconjugate Chemistry, DOI: 10.1021 /acs.bioconjchem.5b00430, 2015, pp. A-R (18 pages) together with Supporting Information Section, 2015, pp. 1-17.
Widdison et al., "Semisynthetic Maytansine Analogues for the Targeted Treatment of Cancer", Journal Of Medicinal Chemistry, American Chemical Society, US; Jul. 13, 2006, vol. 49, No. 14, pp. 4392-4408, XP002679529.
Wolf Philipp, "Anti-psma antibody-drug conjugates and immunotoxins", Chapter 15 of Antibody-drug conjugates and immunotoxins (2012) Gail Phillips (ed), ISBN 978-1-4614-5456-4.
Yoshitake et al., "Conjugation of Glucose Oxidase from Aspergillus niger and Rabbit Antibodies Using N-Hydroxysuccinimide Ester of N-(4-Carboxycyclohexylmethyl)-Maleimide", Eur. J. Biochem., vol. 101, 1979, pp. 395-399.
Zhao et al., "Synthesis and Evaluation of Hydrophilic Linkers for Antibody-Maytansinoid Conjugates", Journal of Medicinal Chemistry, May 26, 2011, vol. 54, No. 10, pp. 3606-3623; XP55046274.
Lowe, Derek; "Not alphafold's fault", Blog "In the Pipeline," entry of Sep. 7, 2022.
Reynolds, Fred et al; "A functional proteomic method for biomarker discovery", PLoS ONE (2011) 6(7) e22471.

\* cited by examiner

BIOLOGICALLY ACTIVE MOLECULES, CONJUGATES THEREOF, AND THERAPEUTIC USES

TECHNICAL FIELD

The present disclosure provides Ligand-Biologically Active Molecule Conjugates wherein the Ligand is connected to the Biologically Active Molecule through a linker compound. The present disclosure also provides conjugate compounds in pharmaceutical compositions for use in various therapeutic applications.

BACKGROUND OF THE INVENTION

Proliferative diseases are characterized by uncontrolled growth and spread of abnormal cells. If the spread is not controlled, it can result in death. Abnormal proliferation, for example, cancer, is caused by both external factors (e.g., tobacco, chemicals, radiation and infectious organisms) and internal factors (inherited mutations, immune system conditions, the mutations that occur from metabolism). These causal factors may act together or in sequence to initiate or promote abnormal proliferation. Cancer is treated by surgery, radiation, chemotherapy, hormones and immunotherapy. However, there is a need for more effective anti-proliferation drugs.

The ideal anti-proliferation therapy would enable targeted delivery of highly cytotoxic agents to tumor cells and would leave normal cells unaffected. Conventional chemotherapeutic treatment, with maytansine for example, is limited because of the toxic side-effects that arise from effects of the drug on non-cancerous cells. Various approaches to targeted drug delivery have been tried, including the use of conjugates of tumor targeted probes (such as antibodies or growth factors) with toxins such as pseudomonas or diphtheria toxins, which arrest the synthesis of proteins and cells. However, the side effects include reaction of the immune system due to non-human components of the conjugates. Further, the half-life of the drug conjugates were limited due to elimination from the circulation through renal filtration, and schematic degradation, uptake by the reticuloendothelial system (RES), and accumulation in non-targeted organs and tissues.

Another approach uses passive drug carriers such as polymers, liposomes, and polymeric micelles to take advantage of the hyper-permeability of vascular endothelia of tumor tissue. Polymeric drugs and macromolecules accumulate within solid tumors due to an enhanced permeability and retention mechanism. However, barriers of using such targeted deliveries include fast clearance of foreign particles from the blood, and technological hindrances in obtaining highly standardized, pharmaceutically acceptable drug delivery systems with the necessary specificity and selectivity for binding tumor cells.

Thus, a need exists for targeted anti-proliferative compounds.

SUMMARY OF THE INVENTION

The present disclosure relates to conjugate compounds represented by the following structural formula (I):

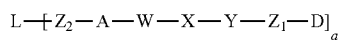
(I)

wherein:
L is absent or a ligand;
further wherein:
when L is a ligand, L is capable of binding to a cell or cell population;
a is an integer from 1 to 10;
$Z_2$ and $Z_1$ are each independently absent or a spacer;
D is a Biologically Active Molecule;
A is a natural or non-natural amino acid, or a peptide comprising 2-20 amino acids;
W is absent, —O—, —S—, —CR$_5$R$_6$—, —NR$_4$—;
further wherein: $R_4$, $R_5$, and $R_6$ are each independently H, or a substituted or unsubstituted: alkyl, alkenyl, alkynyl, aryl, heteroaryl, or heterocyclyl;
X is absent, aryl, heteroaryl, cycloalkyl, heterocyclyl, wherein aryl, heteroaryl, cycloalkyl, and heterocyclyl are optionally substituted; and
Y is absent, or a spacer.

The present disclosure also provides linker-biologically active compounds represented by the following structural formula (V):

(V)

wherein:
$Z_2$ and $Z_1$ are each independently absent or a spacer;
D is a Biologically Active Molecule;
A is a natural or non-natural amino acid, or a peptide comprising 2-20 amino acids;
W is absent, —O—, —S—, —CR$_5$R$_6$—, —NR$_4$—;
further wherein: $R_4$, $R_5$, and $R_6$ are each independently H, or a substituted or unsubstituted: alkyl, alkenyl, alkynyl, aryl, heteroaryl, or heterocyclyl;
X is absent, aryl, heteroaryl, cycloalkyl, heterocyclyl, wherein aryl, heteroaryl, cycloalkyl, and heterocyclyl are optionally substituted; and
Y is absent, or a spacer.

The present disclosure also provides linkers represented by the following structural formula (VI).

In one embodiment, the linker compounds is represented by formula (VI):

(VI)

wherein:
$Z_2$ and $Z_1$ are each independently absent or a spacer;
A is a natural or non-natural amino acid, or a peptide comprising 2-20 amino acids;
W is absent, —O—, —S—, —CR$_5$R$_6$—, —NR$_4$—;
X is absent, aryl, heteroaryl, cycloalkyl, heterocyclyl, wherein aryl, heteroaryl, cycloalkyl, and heterocyclyl are optionally substituted;
Y is absent,

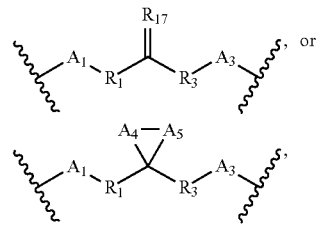

wherein $A_1$, $A_3$, $R_1$ and $R_3$ are each independently absent, an amino acid, a peptide having 2-20 amino acids, an alkyl, an alkynyl, an alkenyl, a cycloalkyl, an aryl, a heteroaryl, a heterocyclyl, —CR$_5$R$_6$—, —O—, —C(=O)—, —O—C(=O)—, —C(=O)—O—, —O—C(=O)—O—, —C(=O)—, —(CH$_x$)$_{p1}$—, —C(=O)—O—(CH$_x$)$_{p1}$—, —(CH$_x$)$_{p1}$—C(=O)—, —(CH$_x$)$_{p1}$—C(=O)—O—, —(O—(CH$_2$)$_{p2}$—)$_{p3}$—, —((CH$_2$)$_{p2}$—O—)$_{p3}$—, —C(=S)—, —C(=S)—S—, —S—C(=S)—, —C(=S)—NH—, —S—C(=S)—S—, —S—, —SO—, —SO$_2$—, —NR$_4$—, —N(R$_4$)—C(=O)—N(R$_8$)—, —N(R$_4$)—C(=O)O—, —N(R$_4$)—C(=O)—, —C(=O)—N(R$_4$)—, —C(=O)—N(R$_4$)—C(=O)—, —O—C(=O)—NR$_4$—, wherein alkyl, alkynyl, alkenyl, cycloalkyl, aryl, heteroaryl, and heterocyclyl are optionally substituted;

A$_4$ and A$_5$ are each independently —O—, —S—, —NR$_{18}$—, —CR$_5$R$_6$—;

R$_{17}$ is selected from the group consisting of O, S, NR$_{18}$, CR$_5$R$_6$;

R$_{18}$ is selected from the group consisting of H, alkyl, alkynyl, alkenyl, cycloalkyl, aryl, heteroaryl, heterocyclyl, and acyl, wherein alkyl, alkynyl, alkenyl, cycloalkyl, aryl, heteroaryl, heterocyclyl, and acyl are optionally substituted;

R$_4$, R$_5$, R$_6$ and R$_8$ are each independently H, or a substituted or unsubstituted: alkyl, alkenyl, alkynyl, aryl, heteroaryl, or heterocyclyl;

p1, p2 and p3 are each independently 0, or an integer from 1 to 100; and x is 0, 1 or 2.

In one aspect, the disclosure provides compounds of formula (VI), wherein Z$_2$ is represented by the following structural formula:

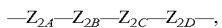

wherein:

Z$_{2A}$, Z$_{2B}$, Z$_{2C}$ and Z$_{2D}$ are each independently absent, an amino acid, a peptide having 2-20 amino acids, an alkyl, an alkynyl, an alkenyl, a cycloalkyl, an aryl, a heteroaryl, a heterocyclyl, —CR$_5$R$_6$—, —O—, —C(=O)—, —O—C(=O)—, —C(=O)—O—, —O—C(=O)—O—, —C(=O)—(CH$_x$)$_{p1}$, —C(=O)—O—(CH$_x$)$_{p1}$, —(CH$_x$)$_{p1}$—C(=O)—, —(CH$_x$)$_{p1}$—C(=O)—O—, —(O—(CH$_2$)$_{p2}$—)$_{p3}$—, —((CH$_2$)$_{p2}$—O—)$_{p3}$—, —C(=S)—, —C(=S)—S—, —C(=S)—NH—, —S—C(=S)—, —S—C(=S)—S—, —S—, —SO—, —SO$_2$—, —NR$_4$—, —N(R$_4$)—C(=O)—N(R$_8$)—, —N(R$_4$)—C(=O)O—, —N(R$_4$)—C(=O)—, —C(=O)—N(R$_4$)—, —C(=O)—N(R$_4$)—C(=O)—, —O—C(=O)—N(R$_4$)—, —O—C(=S)—N(R$_4$)—, —C(=S)—N(R$_4$)—, —N=C=S, —N=C=O,

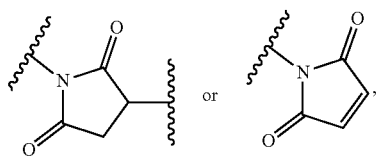 [SMILES: *C1CC(=O)N(*)C1=O ; *N1C(=O)C=CC1=O]

wherein alkyl, alkynyl, alkenyl, cycloalkyl, aryl, heteroaryl and heterocyclyl are optionally substituted and R$_4$, R$_5$, R$_6$ and R$_8$ are each independently H, or a substituted or unsubstituted: alkyl, alkenyl, alkynyl, aryl, heteroaryl, or heterocyclyl.

The present disclosure also relates to pharmaceutical composition comprising a therapeutically effective amount of a compound of formula (I) or a pharmaceutically acceptable salt thereof and one or more pharmaceutically acceptable carriers, diluents, or excipients.

The present disclosure also provides a method of reducing, retarding or stopping an abnormal cell growth comprising contacting the abnormal cell with a compound of formula (I), in an amount sufficient to retard, reduce or stop the abnormal cell growth, and wherein the abnormal cell growth is retarded, reduced or stopped.

The present disclosure also provides a method of killing a cell, comprising contacting the cell with a compound of formula (I), in an amount sufficient to kill the cell, and wherein the cell is killed.

The present disclosure also provides a method of treatment of a medical disorder in an individual suffering from the medical disorder, comprising administering to the individual an effective amount of a composition comprising a compound of formula (I).

The present disclosure also provides a method of reducing tumor size, stopping tumor size increase, reducing tumor proliferation, or preventing tumor proliferation in an individual in need thereof comprising administering to the individual an effective amount of a composition to reduce tumor size, stop tumor size increase, reduce tumor proliferation, or prevent tumor proliferation, wherein the composition comprises a compound of formula (I).

The present disclosure also relates to precursor Biologically Active Molecule-linker compounds as represented by formula (V). Compounds of formula (V) provide building blocks for conjugate compounds of formula (I). In addition, compounds of formula (V) may be provided as compositions, pharmaceutical compositions and pharmaceutically acceptable salts thereof.

The present disclosure further includes the use of any of the compositions comprising compounds of formula (I) and/or pharmaceutical formulations in the manufacture of a medicament for the treatment, prevention and/or amelioration of a medical disorder.

The present disclosure further includes the use of any of the compositions comprising compounds of formula (I) and/or pharmaceutical formulations in the manufacture of a medicament for the treatment, prevention and/or amelioration of a tumor.

BRIEF DESCRIPTION OF THE DRAWINGS

FIG. 1A shows the cell viability results of C4-2 cells (prostate cancer cell line) treated with compound 2, isotype control antibody conjugated to compound 3 ("Isotype Control-3"), anti-PSMA antibody conjugated to compound 3 ("PSMA-3"), and unconjugated anti-PSMA antibody ("PSMA").

FIG. 1B shows the cell viability results of C4-2 cells (prostate cancer cell line) treated with compound 6, isotype control antibody conjugated to compound 7 ("Isotype Control-7"), anti-PSMA antibody conjugated to compound 7 ("PSMA-7"), and unconjugated anti-PSMA antibody ("PSMA").

FIG. 1C shows the cell viability results of C4-2 cells (prostate cancer cell line) treated with compound 25, isotype control antibody conjugated to compound 21 ("Isotype Control-21"), anti-PSMA antibody conjugated to compound 21 ("PSMA-21"), and unconjugated anti-PSMA antibody ("PSMA").

FIG. 2 shows the cell viability results of PC3/hSTEAP1 cells (prostate cancer cell line expressing exogenous hSTEAP1) treated with compound 6, isotype control antibody conjugated to compound 7 ("Isotype Control-7"), anti-STEAP1 antibody conjugated to compound 7 ("STEAP1-7"), and unconjugated anti-STEAP1 antibody ("STEAP1").

FIG. 3 shows the cell viability results of T47D cells (breast cancer cell line) treated with compound 6, isotype control antibody conjugated to compound 7 ("Isotype Control-7"), anti-PRLR antibody conjugated to compound 7 ("PRLR-7"), and unconjugated anti-PRLR antibody ("PRLR").

FIG. 4 shows the cell viability results of HEK293/hEGFRvIII cells (HEK293 cells expressing exogenous hEGFRvIII) treated with compound 6, isotype control antibody conjugated to compound 7 ("Isotype Control-7"), anti-EGFRvIII antibody conjugated to compound 7 ("EGFRvIII-7"), and unconjugated anti-EGFRvIII antibody ("EGFRvIII").

FIG. 5 shows the cell viability results of MMT/hEGFRvIII cells (MMT cells expressing exogenous hEGFRvIII) treated with compound 6, isotype control antibody conjugated to compound 7 ("Isotype Control-7"), anti-EGFRvIII antibody conjugated to compound 7 ("EGFRvIII-7"), and unconjugated anti-EGFRvIII antibody ("EGFRvIII").

FIG. 6 shows the cell viability results of U251/hEGFRvIII cells (U251 cells expressing exogenous hEGFRvIII) treated with compound 6, isotype control antibody conjugated to compound 7 ("Isotype Control-7"), anti-EGFRvIII antibody conjugated to compound 7 ("EGFRvIII-7"), and unconjugated anti-EGFRvIII antibody ("EGFRvIII").

FIG. 7, panels A and B show the cell viability results of HEK293 and U87MG cells, respectively, treated with compounds 6, 27, 29, and 31 (all unconjugated).

FIG. 8, panels A-E show the cell viability results of HEK293, U251, C4-2, PC3 and MMT cells, respectively, treated with compounds 6, 9, 33 and 35 (all unconjugated).

DETAILED DESCRIPTION

Figure 1A:
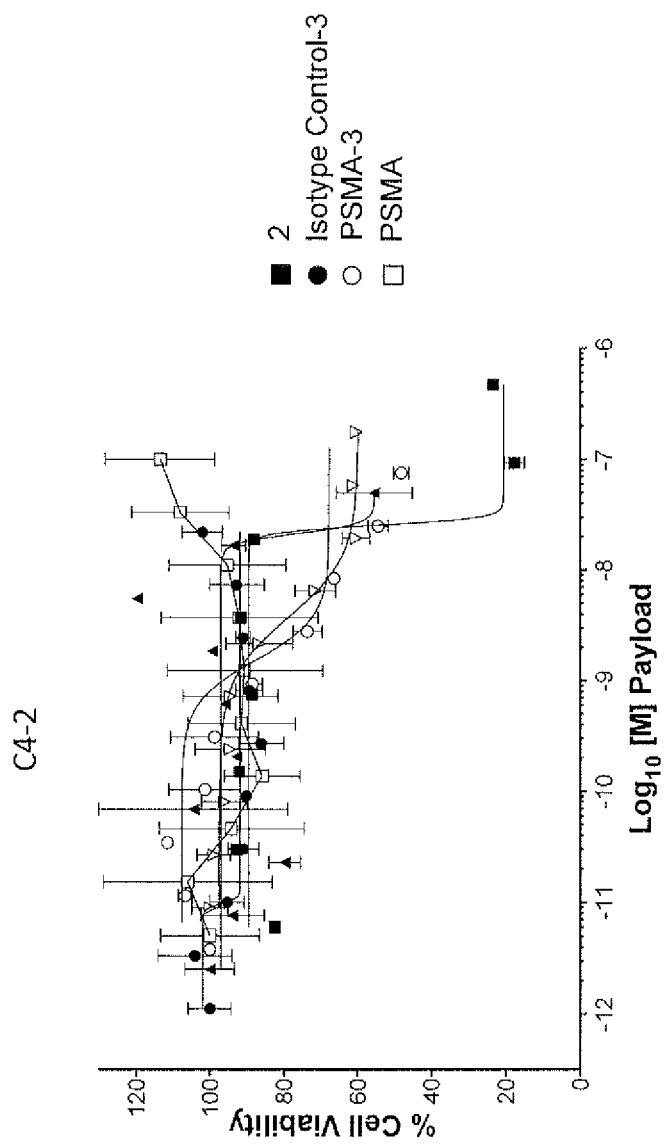
FIGS. 1A, 1B, 1C, and 2-8 depict the results of cell viability assays in which various cancer cell lines were grown in vitro and treated with serial dilutions of antibodies, free drug, or antibody-drug conjugates as shown. Percent viability was determined in accordance with the methods set forth in Example 14.

The references to certain embodiments made in the following description are considered illustrative only of the principles of the disclosure. Further, since numerous modifications and changes will readily be apparent to those skilled in the art, it is not intended to limit the disclosure to the exact construction and process shown as described herein. Accordingly, all suitable modifications and equivalents may be resorted to as falling within the scope of the disclosure and as defined by the claims that follow.

The words "comprise", "comprising", "include" and "including" when used in this specification and in the following claims are intended to specify the presence of the stated features, integers, components, or steps, but they do not preclude the presence or addition of one or more additional features, integers, components, or steps thereof.

General terms used in any of the embodiments herein can be defined as follows; however, the meaning stated should not be interpreted as limiting the scope of the term per se.

The term "conjugate" as used herein refers to compound having a Ligand, linker and Biologically Active Molecule. Illustrative examples include compounds of formula (I), (III) and (IV).

The term "spacer" as used herein refers to chemical building blocks of the linker used to spatially separate the Ligand from the Biologically Active Molecule and to allow for catabolism of the linker inside of cells. A spacer can be represented by $Z_1$ and $Z_2$.

The term "macrolide" as used herein refers to any Biologically Active Molecule having a macrolide ring.

The term "alkyl" as used herein refers to a hydrocarbon group having a general formula $C_nH_{2n+1}$. Examples of alkyl include: methyl, ethyl, 1-propyl, 2-propyl, 1-butyl, and the like. Typical alkyl have from one to ten carbon atoms, one to nine carbon atoms, one to eight carbon atoms, one to seven carbon atoms, one to six carbon atoms, one to five carbon atoms, one to four carbon atoms, one to three carbon atoms, one to two carbon atoms or one carbon atom.

The term "aryl" as used herein refers to a monovalent or polycyclic aromatic hydrocarbon typically having 6 to 18 carbon atoms. Example aryl include phenyl (like benzene), substituted benzenes, naphthalene, anthracene, indenyl, tetrahydronapthyl and the like.

The term "alkenyl" as used herein refers to an aliphatic linear or branched monovalent hydrocarbon radical of two or more carbon atoms with at least one site of unsaturation. Alkenyl have a general formula of $R_2C=CR_2$. Examples of alkenyl include: ethylenyl, vinyl, allyl, and the like.

The term "alkynyl" as used herein refers to a univalent aliphatic hydrocarbon radical containing a triple bond. Typical alkynyl are from two to twenty carbon atoms (and include at least one triple bond). Examples alkynyl include ethynyl, propynyl, 1-butynyl, 2-butynyl, 1-pentynyl, hexynyl and the like.

The term "cycloalkyl" as used herein, refers to a monovalent saturated carbocyclic ring radical. Typical cycloalkyl are 3 to 7 member monocyclic ring radicals. One example of a cycloalkyl is cyclohexyl.

The term "heteroaryl" as used herein, refers to a monovalent aromatic radical of 5 or 6 membered rings. Heteroaryl includes fused ring systems (at least one must be aromatic) that include up to 5 to 18 atoms, containing one or more heteroatoms independently selected from nitrogen, sulfur or oxygen. Illustrative heteroaryl are pyridinyl, triazolyl, furyl, pyrazinyl, thienyl, isoxazolyl, indazolyl, furazanyl, benzothiazolyl, quinazolinyl, and furopyridinyl.

The term "heterocyclyl" as used herein refers to saturated or partially saturated carbocyclic radical typically of 3 to 18 carbon atoms in which at least one ring atom is a heteroatom selected from nitrogen, oxygen, phosphorous, and sulfur. A heterocycyl may be a monocycle or a bicycle, for example. Example heterocyclyl are pyrolidinyl, tetrahydrofuranyl, dihydropyranyl, thioxanyl, 2H-pyranyl, dioxanyl, dithianyl, piperidino, and the like.

The phrase "pharmaceutically acceptable salt" as used herein refers to both organic and inorganic salts of the conjugate compounds described herein, e.g., compounds of formula (I), (III), (IV) and (V). The salts are pharmaceutically acceptable and include: sulfate, citrate, nitrate, phosphate, ascorbate, bromide, gluconate, benzoate, oxalate, pantothenate, and the like. Note that pharmaceutically acceptable salts herein may include more than one charged atom in its structure as well as one or more counter ion. Preparation of conjugate compounds herein as pharmaceutically acceptable salts is well known to one of skill in the art.

The term "human antibody" as used herein is intended to include antibodies having variable and constant regions derived from human immunoglobulin sequences. The human mAbs of the invention may include amino acid residues not encoded by human immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species have been grafted onto human FR sequences.

The term "therapeutically effective amount" as used herein refers to an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

Ligands and Binding Partners

The effectiveness of the conjugate compound embodiments described herein depend on the selectivity of the Ligand to bind its ligand binding partner.

In one embodiment, Ligands are any molecule capable of binding with some specificity to a given binding partner within a mammal where the interaction can result in a therapeutic use. In some aspects the Ligand is capable of binding to a cell or cell population.

Ligands for use herein include antibodies, lymphokines, hormones, growth factors, viral receptors, interleukins, or any other cell binding or peptide binding molecule or substance.

In one embodiment the Ligand is an antibody. As defined herein, antibody refers to monoclonal antibodies, polyclonal antibodies, antibody fragments (Fab, Fab', and F(ab)2, minibodies, diabodies, tribodies, and the like), and bispecific antibodies. Antibodies herein can be humanized using methods described in U.S. Pat. No. 6,596,541 and US Pulication No. 2012/0096572, each incorporated by reference in their entirety.

Where the Ligand is an antibody, it binds to an antigen binding partner that is a polypeptide and may be a transmembrane molecule (e.g., receptor) or a growth factor. Exemplary antigens include, but are not limited to, molecules such as renin; a growth hormone, including human growth hormone and bovine growth hormone; growth hormone releasing factor; parathyroid hormone; thyroid stimulating hormone; lipoproteins; alpha1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (M1P-I-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; 19E; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-$\beta$; platelet-derived growth factor (PDGF); fibroblast growth factor such as aFGF and bFGF; fibroblast growth factor receptor 2 (FGFR2), epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-l and -II (IGF-l and IGF-II); des(I-3)-IGF-l (brain IGF-l), insulin-like growth factor binding proteins, EpCAM, GD3, FLT3, PSMA, PSCA, MUCI, MUCI6, STEAP, CEA, TENB2, EphA receptors, EphB receptors, folate receptor, FOLRI, mesothelin, cripto, alphavbeta6, integrins, VEGF, VEGFR, EGFR, transferrin receptor, lRTAI, lRTA2, lRTA3, lRTA4, lRTA5; CD proteins such as CD2, CD3, CD4, CD5, CD6, CD8, CDII, CDI4, CDI9, CD20, CD21, CD22, CD25, CD26, CD28, CD30, CD33, CD36, CD37, CD38, CD40, CD44, CD52, CD55, CD56, CD59, CD70, CDI9, CD80. CD81, CD103, CD105, CD134, CD137, CD138, CDI52, or an antibody which binds to one or more tumor-associated antigens or cell-surface receptors disclosed in US Publication No. 2008/0171040 or US Publication No. 2008/0305044 and incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CDlla, CDllb, CDllc, CDI8, an ICAM, VLA-4 and VCAM; a tumor associated antigen such as AFP, ALK, B7H4, BAGE proteins, $\beta$-catenin, brc-abl, BRCA1, BORIS, CA9 (carbonic anhydrase IX), caspase-8, CD20, CD40, CD123, CDK4, CEA, CLEC12A, c-kit, cMET, CTLA4, cyclin-B1, CYP1B1, EGFR, EGFRvIII, endoglin, Epcam, EphA2, ErbB2/Her2, ErbB3/Her3, ErbB4/Her4, ETV6-AML, Fra-1, FOLR1, GAGE proteins (e.g., GAGE-1, -2), GD2, GD3, GloboH, glypican-3, GM3, gp100, Her2, HLA/B-raf, HLA/EBNA1, HLA/k-ras, HLA/MAGE-A3, hTERT, IGF1R, LGR5, LMP2, MAGE proteins (e.g., MAGE-1, -2, -3, -4, -6, and -12), MART-1, mesothelin, ML-IAP, Muc1, Muc16 (CA-125), MUM1, NA17, NGEP, NY-BR1, NY-BR62, NY-BR85, NY-ESO1, OX40, p15, p53, PAP, PAX3, PAX5, PCTA-1, PDGFR-$\alpha$, PDGFR-$\beta$, PDGF-A, PDGF-B, PDGF-C, PDGF-D, PLAC1, PRLR, PRAME, PSCA, PSGR, PSMA (FOLH1), RAGE proteins, Ras, RGS5, Rho, SART-1, SART-3, Steap-1, Steap-2, STn, survivin, TAG-72, TGF-$\beta$, TMPRSS2, Tn, TNFRSF17, TRP-1, TRP-2, tyrosinase, and uroplakin-3, and fragments of any of the above-listed polypeptides.

Ligands may also include ankyrin repeat proteins, interferons, lymphokines such as IL-2 or IL-3, hormones like insulin and glucocorticoids, growth factors such as EGF, transferrin, fibronectin type III, etc.

Embodiments herein are target specific for therapeutic use. In one embodiment, Ligands are prepared to interact with and bind to antigens defined as tumor antigens, which include antigens specific for a type of tumor or antigens that are shared, overexpressed or modified on a particular type of tumor. Examples include: alpha-actinin-4 with lung cancer, ARTC1 with melanoma, BCR-ABL fusion protein with chronic myeloid leukemia, B-RAF, CLPP or Cdc27 with melanoma, CASP-8 with squamous cell carcinoma, and hsp70-2 with renal cell carcinoma as well as the following shared tumor-specific antigens, for example: BAGE-1, GAGE, GnTV, KK-LC-1, MAGE-A2, NA88-A, TRP2-INT2.

Biologically Active Molecules

Biologically Active Molecules herein include any molecules that have a therapeutic use in a mammal. In typical embodiments the molecule is beneficially delivered to a target within the mammal and in particular is beneficially delivered to and then within a cell (e.g., endocytosis) as compared to molecules released into the vascular or lymphatic systems.

In one aspect, Biologically Active Molecules are compounds that result in the inhibition, retardation, reduction, and/or prevention of cell growth. Biologically Active Molecules can also result in cell death via necrosis or apoptosis. Illustrative Biologically Active Molecules for use in conjugate compounds described herein include: maytansinoids (e.g., DM1, DM4, etc.), auristatins (e.g., MMAE, MMAD, MMAF, etc.), duocarmycin (e.g., MGBA), dolastatin, toxoids, and other chemotherapeutically effective drugs.

Other specific examples of Biologically Active Molecules that can be used in the context of the present invention include, e.g., 1-dehydrotestosterone, 2-pyrrolinodoxorubicin, 5-fluorouracil, 6-mercaptopurine, 6-thioguanine, actinomycin D, anthracycline, anthramycin (AMC), bleomycin, busulfan, calicheamicins, carmustine cisplatin, colchicin, cyanomorpholino-doxorubicin, cyclophosphamide, cytarabine, cytochalasin B, dactinomycin, daunorubicin, decarbazine, dibromomannitol, dihydroxy anthracin dione, doxorubicin, emetine, epirubicin, ethidium bromide, etoposide, gramicidin D, glucocorticoids, lidocaine, lomustine (CCNU), mechlorethamine, melphalan, methotrexate, mithramycin, mitomycin, mitoxantrone, morpholino-doxorubicin, procaine, propranolol, puromycin, pyrrolobenzodiazapines, sibiromycin, streptozotocin, taxol, tenoposide, tetracaine, thioepa chlorambucil, trichothecenes, tubulysin, vincristine, and stereoisomers, isosteres, analogs or derivatives of any of the foregoing.

In one embodiment the Biologically Active Molecule is a maytansinoid or a maytansinoid analog. Exemplary maytansinoids for use herein are described in Widdison et al., J. Med. Chem., 2006, 49, 4392-4408, incorporated by reference herein for all purposes.

Linker Materials

The present disclosure includes a linker compound that is chemically capable of covalently linking two spaced chemical moieties. The linker spaces and links two moieties, for example, the linker can link a Ligand and a Biologically Active Molecule. In one aspect, the linker is self immolative wherein the linker connects two or more different chemical moieties and releases at least one of the said chemical moieties in the presence of an enzyme. In another aspect, the linker may be attached to other chemical moieties, including but not limited to, analytical agents, biomolecules, targeting agents, detectable labels, diagnostic agents, and the like. In one embodiment, the linker attaches a Biologically Active Molecule and a Ligand. In another embodiment, the linker attaches a biologically active macrolide and a Ligand. In yet another embodiment, the linker attaches a biologically active macrolide and an antibody or fragments thereof.

In one aspect, the linkers are useful to covalently link ligands with therapeutic agents and markers. In another aspect, the linkers improve chemical and/or systemic stability of the attached moieties. In another aspect, the linkers reduce in vivo toxicity of the attached moieties. In another aspect, the linkers improve pharmacokinetics, pharmacodynamics, and/or bioavailability of the attached moieties. In one aspect, the linkers cleave and release a Biologically Active Molecule at a site in or near a target cell or a cell population in a pharmacologically effective form. In one aspect, the cleavage is performed by enzymes. In one aspect, the cleavable groups on the linkers for the enzymatic cleavage include, but not limited to, peptide bonds, ester linkages, and disulfide linkages. In another aspect, the linker is cleaved through pH changes.

In one embodiment, the linker compounds is represented by formula (VI):

$$Z_2\text{-A-W-X—Y—}Z_1 \quad (VI)$$

wherein:

$Z_2$ and $Z_1$ are each independently absent or a spacer;

A is a natural or non-natural amino acid, or a peptide comprising 2-20 amino acids;

W is absent, —O—, —S—, —$CR_5R_6$—, —$NR_4$—;

X is absent, aryl, heteroaryl, cycloalkyl, heterocyclyl, wherein aryl, heteroaryl, cycloalkyl, and heterocyclyl are optionally substituted;

Y is absent,

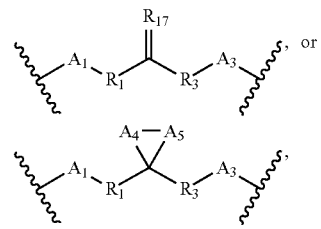

wherein $A_1$, $A_3$, $R_1$ and $R_3$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2})_{p3}$—, —(($CH_2)_{p2}$—O—$)_{p3}$, —C(=S)—, —C(=S)—S—, —C(=S)—NH—, —S—C(=S)—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, —C(=O)—$N(R_4)$—C(=O)—, —O—C(=O)—$NR_4$—, wherein alkyl, alkynyl, alkenyl, cycloalkyl, aryl, heteroaryl, and heterocyclyl are optionally substituted;

$A_4$ and $A_5$ are each independently —O—, —S—, —$NR_{18}$—, —$CR_5R_6$—;

$R_{17}$ is selected from the group consisting of O, S, $NR_{18}$, $CR_5R_6$;

$R_{18}$ is selected from the group consisting of H, alkyl, alkynyl, alkenyl, cycloalkyl, aryl, heteroaryl, heterocyclyl, and acyl, wherein alkyl, alkynyl, alkenyl, cycloalkyl, aryl, heteroaryl, heterocyclyl, and acyl are optionally substituted;

$R_4$, $R_8$, $R_6$ and $R_8$ are each independently H, or a substituted or unsubstituted: alkyl, alkenyl, alkynyl, aryl, heteroaryl, or heterocyclyl;

p1, p2 and p3 are each independently 0, or an integer from 1 to 100; and x is 0, 1 or 2.

In one aspect, the disclosure provides compounds of formula (VI), wherein $Z_2$ is represented by the following structural formula:

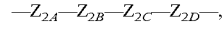

wherein:

$Z_{2A}$, $Z_{2B}$, $Z_{2C}$ and $Z_{2D}$ are each independently absent, an amino acid, a peptide having 2-20 amino acids, an alkyl, an alkynyl, an alkenyl, a cycloalkyl, an aryl, a heteroaryl, a heterocyclyl, —CR$_5$R$_6$—, —O—, —C(═O)—, —O—C(═O)—, —C(═O)—O—, —O—C(═O)—O—, —C(═O)—(CH$_x$)$_{p1}$, —C(═O)—O—(CH$_x$)$_{p1}$, —(CH$_x$)$_{p1}$—C(═O)—, —(CH$_x$)$_{p1}$—C(═O)—O—, —(O—(CH$_2$)$_{p2}$—)$_{p3}$—, —((CH$_2$)$_{p2}$—O—)$_{p3}$—, —C(═S)—, —C(═S)—S—, —C(═S)—NH—, —S—C(═S)—, —S—C(═S)—S—, —S—, —SO—, —SO$_2$—, —NR$_4$—, —N(R$_4$)—C(═O)—N(R$_8$)—, —N(R$_4$)—C(═O)O—, —N(R$_4$)—C(═O)—, —C(═O)—N(R$_4$)—, —C(═O)—N(R$_4$)—C(═O)—, —O—C(═O)—N(R$_4$), —O—C(═S)—N(R$_4$)—, —C(═S)—N(R$_4$)—, —N═C═S, —N═C═O,

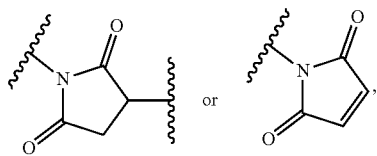 [SMILES: *C1CC(=O)N(*)C1=O ; *N1C(=O)C=CC1=O]

wherein alkyl, alkynyl, alkenyl, cycloalkyl, aryl, heteroaryl, and heterocyclyl are optionally substituted and R$_4$, R$_5$, R$_6$ and R$_8$ are each independently H, or a substituted or unsubstituted: alkyl, alkenyl, alkynyl, aryl, heteroaryl, or heterocyclyl.

In one aspect, the disclosure provides compounds of formula (VI), wherein Z$_1$ is represented by the following structural formula:

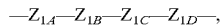

wherein:

Z$_{1A}$, Z$_{1B}$, Z$_{1C}$ and Z$_{1D}$ are each independently absent, an amino acid, a peptide having 2-20 amino acids, an alkyl, an alkynyl, an alkenyl, a cycloalkyl, an aryl, a heteroaryl, a heterocyclyl, —CR$_5$R$_6$—, —O—, —C(═O)—, —O—C(═O)—, —C(═O)—O—, —O—C(═O)—O—, —C(═O)—(CH$_x$)$_{p1}$, —C(═O)—O—(CH$_x$)$_{p1}$, —(CH$_x$)$_{p1}$—C(═O)—, —(CH$_x$)$_{p1}$—C(═O)—O—, —(O—(CH$_2$)$_{p2}$—)$_{p3}$—, —((CH$_2$)$_{p2}$—O—)$_{p3}$—, —C(═S)—, —C(═S)—S—, —C(═S)—NH—, —S—C(═S)—, —S—C(═S)—S—, —S—, —SO—, —SO$_2$—, —NR$_4$—, —N(R$_4$)—C(═O)—N(R$_8$)—, —N(R$_4$)—C(═O)O—, —N(R$_4$)—C(═O)—, —C(═O)—N(R$_4$)—, C(═O)—N(R$_4$)—C(═O)—, —O—C(═O)—N(R$_4$), —O—C(═S)—N(R$_4$)—, —C(═S)—N(R$_4$)—, —N═C═S, —N═C═O,

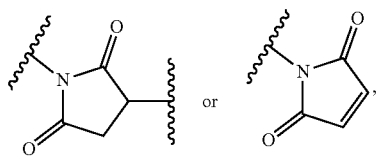 [SMILES: *C1CC(=O)N(*)C1=O ; *N1C(=O)C=CC1=O]

wherein alkyl, alkynyl, alkenyl, cycloalkyl, aryl, heteroaryl, and heterocyclyl are optionally substituted and R$_4$, R$_5$, R$_6$ and R$_8$ are each independently H, or a substituted or unsubstituted: alkyl, alkenyl, alkynyl, aryl, heteroaryl, or heterocyclyl.

In one aspect, the disclosure provides compounds of formula (VI), wherein A is an amino acid selected from the group consisting of alanine, aspartic acid, glutamic acid, phenylalanine, glycine, histidine, isoleucine, lysine, leucine, methionine, asparagine, proline, glutamine, arginine, serine, threonine, valine, tryptophan, tyrosine, cysteine, and citrulline.

In another one aspect, the disclosure provides compounds of formula (VI), wherein A is a peptide selected from the group consisting of valine-citrulline, citrulline-valine, lysine-phenylalanine, phenylalanine-lysine, valine-asparagine, asparagine-valine, threonine-asparagine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, asparagine-alanine.

In one aspect, the disclosure provides compounds of formula (VI), wherein X is an aryl selected from the group consisting of

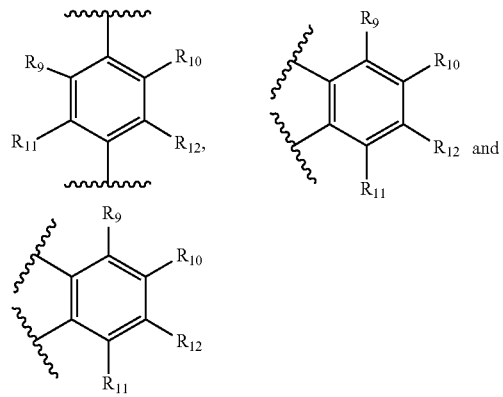

wherein R$_9$, R$_{10}$, R$_{11}$, and R$_{12}$ are each independently H, an alkyl, cycloalkyl, aryl, heteroaryl, heterocyclyl, halogen, NR$_{13}$R$_{14}$, nitro, cyano, —OH, —O—C(═O)—R$_{15}$, —C(═O)—R$_{15}$, —C(═O)—O—R$_{15}$, —C(═O)—NR$_{13}$R$_{14}$; and further wherein, alkyl, cycloalkyl, aryl, heteroaryl, and heterocyclyl are optionally substituted;

R$_{13}$ and R$_{14}$ are each independently H or an optionally substituted alkyl; and R$_{15}$ is an optionally substituted alkyl.

According to certain embodiments, the linkers, the biologically active molecules, and other compounds of the present disclosure can be connected to an antibody or antigen-binding molecule through an attachment at a particular amino acid within the antibody or antigen-binding molecule. Exemplary amino acid attachments that can be used in the context of the disclosure include, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA*, 2008, 105:12451-12456), formyl glycine (see, e.g., Carrico et al., *Nat. Chem. Biol.*, 2007, 3:321-322; Agarwal et al., *Proc. Natl. Acad. Sci., USA*, 2013, 110:46-51, and Rabuka et al., *Nat. Protocols*, 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, and Ryan et al., Food & Agriculture Immunol., 2001, 13:127-130) and disulfide linkers (see, e.g., WO 2013/085925, WO 2010/010324, WO 2011/018611, and Shaunak et al., Nat. Chem. Biol., 2006, 2:312-313).

According to certain other embodiments, the linkers, the biologically active molecules such as drugs can be connected to an antibody or antigen-binding molecule through an attachment at a particular amino acid within the antibody or antigen-binding molecule forming an antibody-drug conjugate (ADC).

Compounds

In one aspect, the present disclosure provides Biologically Active Molecules and Ligand conjugates represented by the following structural formula (I):

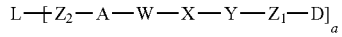

wherein:
L is absent or a Ligand;
further wherein:
when L is a Ligand, L is capable of binding to a cell or cell population;
a is an integer from 1 to 10;
$Z_2$ and $Z_1$ are each independently absent or a spacer;
D is a Biologically Active Molecule;
A is a natural or non-natural amino acid, or a peptide comprising 2-20 amino acids;
W is absent, —O—, —S—, —$CR_5R_6$—, —$NR_4$—;
X is absent, aryl, heteroaryl, cycloalkyl, heterocyclyl, wherein aryl, heteroaryl, cycloalkyl, and heterocyclyl are optionally substituted;
Y is absent,

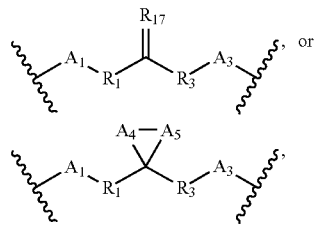

wherein $A_1$, $A_3$, $R_1$ and $R_3$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—$)_{p3}$—, —($(CH_2)_{p2}$—O—$)_{p3}$—, —C(=S)—, —C(=S)—S—, —C(=S)—NH—, —S—C(=S)—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, —C(=O)—$N(R_4)$—C(=O)—, —O—C(=O)—

$NR_4$—, wherein alkyl, alkynyl, alkenyl, cycloalkyl, aryl, heteroaryl, and heterocyclyl are optionally substituted;
$A_4$ and $A_5$ are each independently —O—, —S—, —$NR_{18}$—, —$CR_5R_6$—;
$R_{17}$ is selected from the group consisting of O, S, $NR_{18}$, $CR_5R_6$;
$R_{18}$ is selected from the group consisting of H, alkyl, alkynyl, alkenyl, cycloalkyl, aryl, heteroaryl, heterocyclyl, and acyl, wherein alkyl, alkynyl, alkenyl, cycloalkyl, aryl, heteroaryl, heterocyclyl, and acyl are optionally substituted;
$R_4$, $R_5$, $R_6$ and $R_8$ are each independently H, or a substituted or unsubstituted: alkyl, alkenyl, alkynyl, aryl, heteroaryl, or heterocyclyl;
p1, p2 and p3 are each independently 0, or an integer from 1 to 100; and
x is 0, 1 or 2.

In another aspect, the present disclosure relates to compounds where the Biologically Active Molecule is a cytotoxic biologically active macrolide.

In yet another aspect, the present disclosure provides maytansinoids as represented by formula (II) as biologically active macrolides:

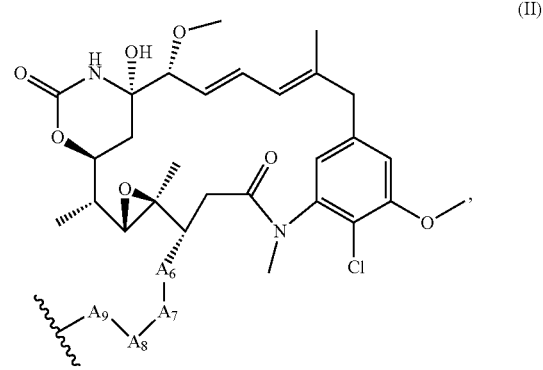

wherein $A_6$, $A_7$, $A_8$, $A_9$ are each independently absent, an amino acid, N-alkyl amino acid, a peptide having 2-20 amino acids, an alkyl, an alkenyl, an alkynyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—$)_{p3}$—, —($(CH_2)_{p2}$—O—$)_{p3}$—, —C(=S)—, —C(=S)—NH—, —C(=S)—S—, —S—C(=S)—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, —C(=O)—$N(R_4)$—C(=O)—, —O—C(=O)—$NR_4$—, further wherein alkyl, alkynyl, alkenyl, cycloalkyl, aryl, heteroaryl, and heterocyclyl are optionally substituted; and $R_4$, $R_5$, $R_6$ and $R_8$ are each independently H, or a substituted or unsubstituted: alkyl, alkenyl, alkynyl, aryl, heteroaryl, or heterocyclyl.

In another embodiment, the maytansinoid is represented by the following structural formula (II)(a):

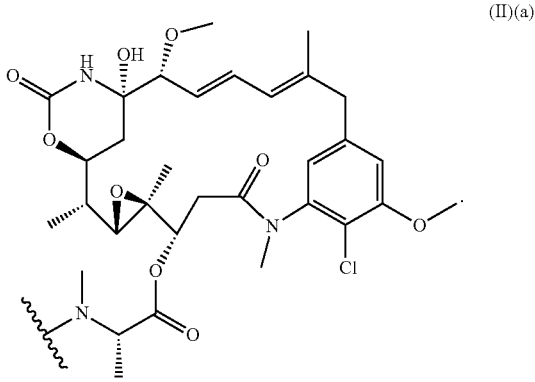 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

(II)(a)

In one aspect, the disclosure provides a compound of formula (I), wherein the Ligand (L) is capable of binding to a specifically targeted cell population.

In another aspect, the disclosure provides a compound of formula (I), wherein the Ligand (L) is selected from the group consisting of proteins, antibodies, fragments of antibodies, nucleic acids, antigen binding scaffolds, and carbohydrates.

In one embodiment, the disclosure provides a compound of formula (I), wherein the Ligand (L) is an antibody or a fragment thereof.

In one embodiment, the disclosure provides a compound of formula (I), wherein Ligand (L) is an antibody or fragment thereof that specifically binds a tumor associated antigen.

In one embodiment, the disclosure provides a compound of formula (I), wherein the antibody or a fragment thereof comprises a sulfur group that is covalently attached with $Z_2$.

In one aspect, the disclosure provides compounds of formula (I), wherein $Z_2$ is represented by the following structural formula:

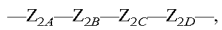

wherein:

$Z_{2A}$, $Z_{2B}$, $Z_{2C}$ and $Z_{2D}$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$, —C(=O)—O—$(CH_x)_{p1}$, —$(CH_x)_{p1}$—C(=O)—, —$(CH_x)_{p1}$—C(=O)—O—, —(O—$(CH_2)_{p2}$—$)_{p3}$—, —($(CH_2)_{p2}$—O—$)_{p3}$—, —C(=S)—, —C(=S)—S—, —C(=S)—NH—, —S—C(=S)—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, —C(=O)—$N(R_4)$—C(=O)—, —O—C(=O)—$N(R_4)$, —O—C(=S)—$N(R_4)$—, —C(=S)—$N(R_4)$—, —N=C=S, —N=C=O,

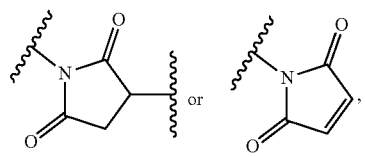 [SMILES: *C1CC(=O)N(*)C1=O ; *N1C(=O)C=CC1=O]

wherein alkyl, alkynyl, alkenyl, cycloalkyl, aryl, heteroaryl, and heterocyclyl are optionally substituted and $R_4$, $R_5$, $R_6$ and $R_8$ are each independently H, or a substituted or unsubstituted: alkyl, alkenyl, alkynyl, aryl, heteroaryl, or heterocyclyl.

In one embodiment, the disclosure provides compounds of formula (I), wherein the antibody or a fragment thereof comprises a sulfur group that is covalently attached with $Z_{2A}$.

In one aspect, the disclosure provides compounds of formula (I), wherein $Z_1$ is represented by the following structural formula:

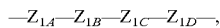

wherein:

$Z_{1A}$, $Z_{1B}$, $Z_{1C}$ and $Z_{1D}$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$, —C(=O)—O—$(CH_x)_{p1}$, —$(CH_x)_{p1}$—C(=O)—, —$(CH_x)_{p1}$—C(=O)—O—, —(O—$(CH_2)_{p2}$—$)_{p3}$—, —($(CH_2)_{p2}$—O—$)_{p3}$—, —C(=S)—, —C(=S)—S—, —C(=S)—NH—, —S—C(=S)—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, C(=O)—$N(R_4)$—C(=O)—, —O—C(=O)—$N(R_4)$, —O—C(=S)—$N(R_4)$—, —C(=S)—$N(R_4)$—, —N=C=S, —N=C=O,

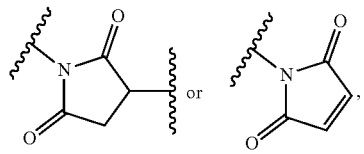 [SMILES: *C1CC(=O)N(*)C1=O ; *N1C(=O)C=CC1=O]

wherein alkyl, alkynyl, alkenyl, cycloalkyl, aryl, heteroaryl, and heterocyclyl are optionally substituted and $R_4$, $R_5$, $R_6$ and $R_8$ are each independently H, or a substituted or unsubstituted: alkyl, alkenyl, alkynyl, aryl, heteroaryl, or heterocyclyl.

In one embodiment, the disclosure provides compounds of formula (I), wherein the Biologically Active Molecule (D) is covalently attached with $Z_1$.

In one aspect, the disclosure provides compounds of formula (I), wherein A is an amino acid selected from the group consisting of alanine, aspartic acid, glutamic acid, phenylalanine, glycine, histidine, isoleucine, lysine, leucine, methionine, asparagine, proline, glutamine, arginine, serine, threonine, valine, tryptophan, tyrosine, cysteine, and citrulline.

In another aspect, the disclosure provides compounds of formula (I), wherein A is a peptide selected from the group consisting of valine-citrulline, citrulline-valine, lysine-phenylalanine, phenylalanine-lysine, valine-asparagine, asparagine-valine, threonine-asparagine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, asparagine-alanine.

In one aspect, the disclosure provides compounds of formula (I), wherein X is an aryl selected from the group consisting of

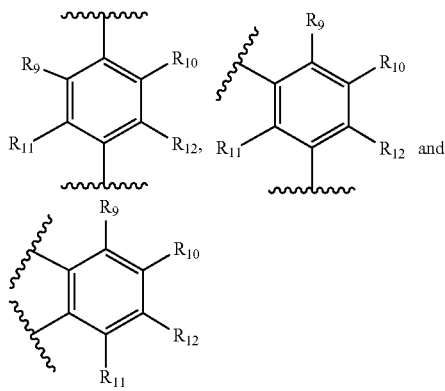

wherein $R_9 R_{10}$, $R_{11}$, and $R_{11}$ are each independently H, an alkyl, cycloalkyl, aryl, heteroaryl, heterocyclyl, halogen, $NR_{13}R_{14}$, nitro, cyano, —OH, —O—C(=O)—$R_{15}$, —C(=O)—$R_{18}$, —C(=O)—O—$R_{15}$, —C(=O)—$NR_{13}R_{14}$; and further wherein, alkyl, cycloalkyl, aryl, heteroaryl, and heterocyclyl are optionally substituted;

$R_{13}$ and $R_{14}$ are each independently H or an optionally substituted alkyl; and $R_{15}$ is an optionally substituted alkyl.

In another one aspect, the disclosure provides compounds of formula (III):

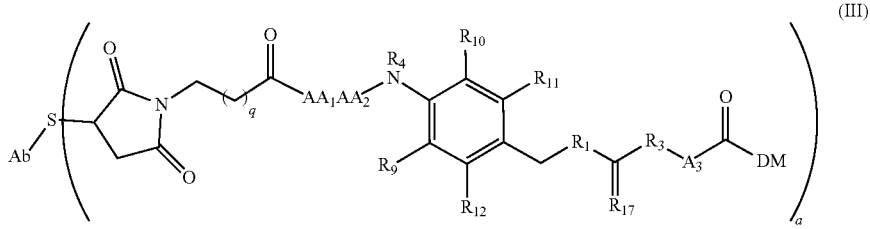

wherein:
Ab is an antibody or a fragment thereof;
$AA_1$-$AA_2$ is a peptide selected from the group consisting of valine-citrulline, citrulline-valine, lysine-phenylalanine, phenylalanine-lysine, valine-asparagine, asparagine-valine, threonine-asparagine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, asparagine-alanine;
a is an integer from 1 to 10;
q is 0 or an integer from 1 to 5;
$A_3$, $R_1$ and $R_3$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—$)_{p3}$—, —($(CH_2)_{p2}$—O—$)_{p3}$—, —C(=S)—, —C(=S)—S—, —C(=S)—NH—, —S—C(=S)—, —S—C(=S)—S—, —S—, —SO—, —$SO_2$—, —$NR_4$—, —$N(R_4)$—C(=O)—N$(R_8)$—, —$N(R_4)$—C(=O)O—, —$N(R_4)$—C(=O)—, —C(=O)—$N(R_4)$—, —C(=O)—$N(R_4)$—C(=O)—, —O—C(=O)—$NR_4$—, wherein alkyl, alkynyl, alkenyl, cycloalkyl, aryl, heteroaryl, and heterocyclyl are optionally substituted;

$R_{17}$ is selected from the group consisting of O, S, $NR_{18}$, $CR_5R_6$;

$R_4$, $R_5$, $R_6$ and $R_8$ are each independently H, or a substituted or unsubstituted: alkyl, alkenyl, alkynyl, aryl, heteroaryl, and heterocyclyl;

$R_9$, $R_{10}$, $R_{11}$, and $R_{12}$ are each independently H, halogen, $NR_{13}R_{14}$, nitro, cyano, —OH, —O—C(=O)—$R_{15}$, —C(=O)—$R_{15}$, —C(=O)—O—$R_{15}$, —C(=O)—$NR_{13}R_{14}$, substituted or unsubstituted: alkyl, cycloalkyl, aryl, heteroaryl, and heterocyclyl;

$R_{13}$ and $R_{14}$ are each independently H or an optionally substituted alkyl; and $R_{15}$ is an optionally substituted alkyl;

p1, p2 and p3 are each independently 0, or an integer from 1 to 100;

x is 0, 1 or 2; and DM is represented by the following structure (e.g., compound of formula (II)(a)):

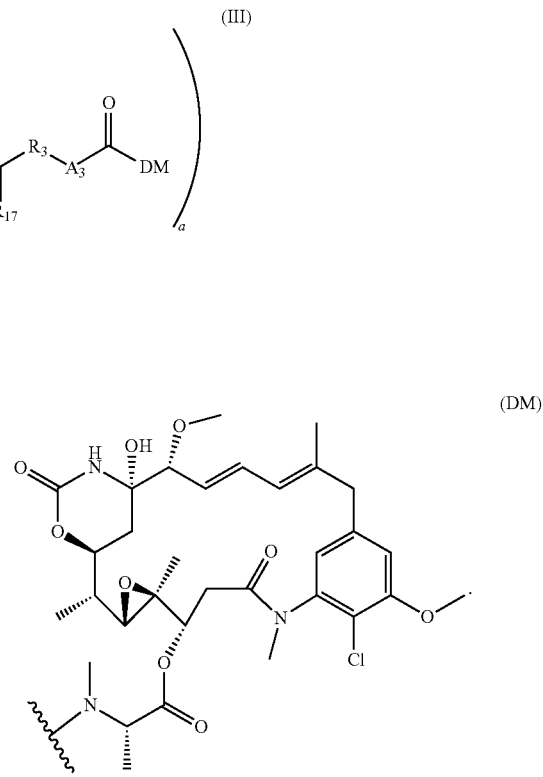

(DM)

In one embodiment, the disclosure provides the compounds of formula (III)

wherein:

q is 4;

$R_1$ and $R_3$ are each independently —O—, —S—, $NR_4$, —$CR_5R_6$—;

$R_{17}$ is selected from the group consisting of O, S, $NR_{18}$, $CR_5R_6$;

$R_{18}$ is selected from the group consisting of H, alkyl, alkynyl, alkenyl, cycloalkyl, aryl, heteroaryl, heterocyclyl, and acyl, wherein alkyl, alkynyl, alkenyl, cycloalkyl, aryl, heteroaryl, heterocyclyl, and acyl are optionally substituted;

$R_4$, $R_5$, $R_6$, $R_9$, $R_{10}$, $R_{11}$, $R_{12}$ are each independently H or alkyl; and $A_3$ is an alkyl.

In one embodiment, the disclosure provides the compounds of formula (III) represented by the following structures (III)(a) and (III)(b):

nine, phenylalanine-lysine, valine-asparagine, asparagine-valine, threonine-asparagine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, asparagine-alanine;

a is an integer from 1 to 10;

q is 0 or an integer from 1 to 5;

$R_1$ is absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, (III)(a)

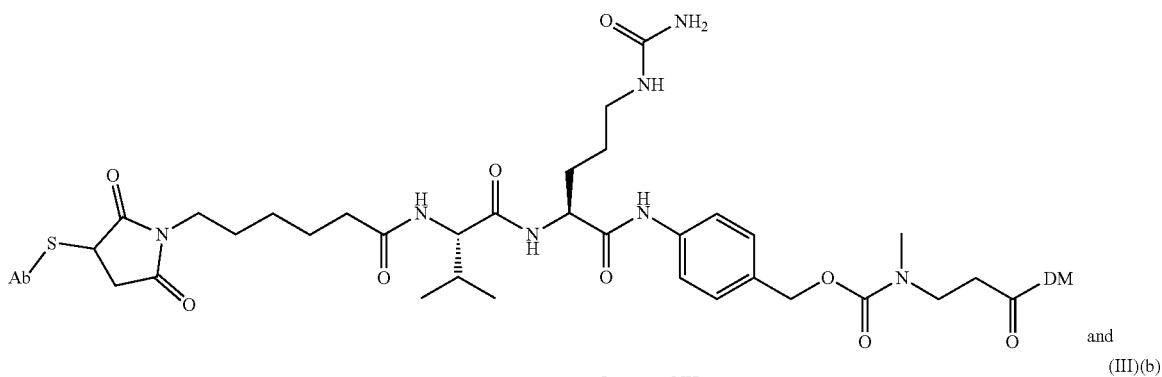

and (III)(b)

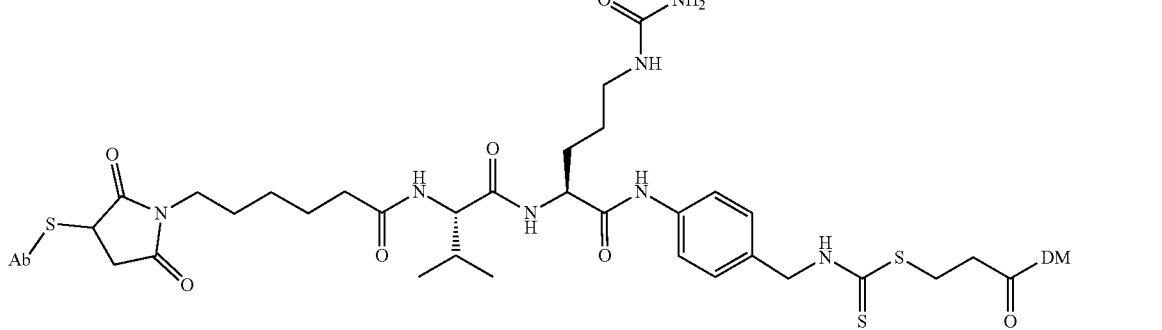

wherein Ab is an antibody or a fragment thereof.

In one aspect, the disclosure provides the compounds of formula (IV):

(IV)

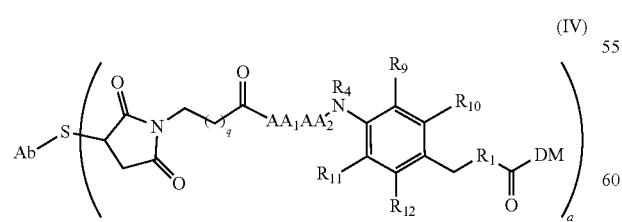

wherein:

Ab is an antibody or a fragment thereof;

$AA_1$-$AA_2$ is a peptide selected from the group consisting of valine-citrulline, citrulline-valine, lysine-phenylala- —$(CH_x)_{p1}$—C(=O)—O—, —(O—$(CH_2)_{p2}$—$)_{p3}$—, —$((CH_2)_{p2}$—O—$)_{p3}$—, —C(=S)—, —C(=S)—S—, —C(=S)—NH—, —S—C(=S)—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, —C(=O)—$N(R_4)$—C(=O)—, —O—C(=O)—$NR_4$—, wherein alkyl, alkynyl, alkenyl, cycloalkyl, aryl, heteroaryl, and heterocyclyl are optionally substituted;

$R_4$, is H, or a substituted or unsubstituted: alkyl, alkenyl, alkynyl, aryl, heteroaryl, and heterocyclyl;

$R_9$, $R_{10}$, $R_{11}$, and $R_{12}$ are each independently H, halogen, $NR_{13}R_{14}$, nitro, cyano, —OH, —O—C(=O)—$R_{15}$, —C(=O)—$R_{15}$, —C(=O)—O—$R_{15}$, —C(=O)—$NR_{13}R_{14}$, substituted or unsubstituted: alkyl, cycloalkyl, aryl, heteroaryl, and heterocyclyl; and DM is represented by the following structure:

(DM)

[Structure of DM]

In one embodiment, the disclosure provides the compounds of formula (IV)
wherein:
q is 4; and
$R_1$ is selected from the group consisting of —O—, —S—, $NR_4$—, and —$CR_5R_6$—; and further wherein $R_4$, $R_5$, and $R_6$ are each independently H or alkyl.

In one embodiment, the disclosure provides the compounds of formula (IV) represented by the following structure (IV)(a):

(IV)(a)

[Structure of IV(a)]

wherein Ab is an antibody or a fragment thereof.
In one aspect, the disclosure provides a compound of Formula (V)

$$Z_2\text{-A-W-X—Y—}Z_1\text{-D} \quad (V)$$

wherein:
$Z_2$ and $Z_1$ are each independently absent or a spacer;
D is a Biologically Active Molecule;
A is a natural or non-natural amino acid, or a peptide comprising 2-20 amino acids;
W is absent, —O—, —S—, —$CR_5R_6$—, or —$NR_4$—;
X is absent, or a substituted or unsubstituted: aryl, heteroaryl, cycloalkyl, heterocyclyl;
Y is absent,

[Structure with $R_{17}$, $A_1$, $R_1$, $A_3$, $R_3$], or

-continued

[Structure with $A_4$—$A_5$, $A_1$, $R_1$, $R_3$, $A_3$], wherein $A_1$, $A_3$, $R_1$ and $R_3$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—$(CH_x)_{p1}$—, —C(=O)—O—$(CH_x)_{p1}$—, —$(CH_x)_{p1}$—C(=O)—, —$(CH_x)_{p1}$—C(=O)—O—, —(O—$(CH_2)_{p2}$—$)_{p3}$—, —$((CH_2)_{p2}$—O—$)_{p3}$—, —C(=S)—, —C(=S)—S—, —C(=S)—NH—, —S—C(=S)—, —S—C(=S)—S—, —S—, —SO—, —$SO_2$—, —$NR_4$—, —$N(R_4)$—C(=O)—$N(R_8)$—, —$N(R_4)$—C(=O)O—, —$N(R_4)$—C(=O)—, —C(=O)—$N(R_4)$—, —C(=O)—$N(R_4)$—C(=O)—, —O—C(=O)—$NR_4$—, wherein alkyl, alkynyl, alkenyl, cycloalkyl, aryl, heteroaryl, and heterocyclyl are optionally substituted;
$A_4$ and $A_5$ are each independently —O—, —S—, —$NR_{18}$—, —$CR_5R_6$—;
$R_{17}$ is selected from the group consisting of O, S, $NR_{18}$, $CR_5R_6$;
$R_{18}$ is selected from the group consisting of H, alkyl, alkynyl, alkenyl, cycloalkyl, aryl, heteroaryl, heterocyclyl, and acyl, wherein alkyl, alkynyl, alkenyl, cycloalkyl, aryl, heteroaryl, heterocyclyl, and acyl are optionally substituted;
$R_4$, $R_5$, $R_6$ and $R_8$ are each independently H, or a substituted or unsubstituted: alkyl, alkenyl, alkynyl, aryl, heteroaryl, heterocyclyl;
p1, p2 and p3 are each independently 0, or an integer from 1 to 100; and
x is 0, 1 or 2.

In one embodiment, the disclosure provides the compound of formula (V),
wherein:
$Z_2$ is represented by Formula (VII):

$$-Z_{2A}-Z_{2B}-Z_{2C}-Z_{2D}- \quad (VII),$$

further wherein:
$Z_{2A}$, $Z_{2B}$, $Z_{2C}$ and $Z_{2D}$ are each independently absent, an amino acid, a peptide having 2-20 amino acids, an alkyl, an alkynyl, an alkenyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—(CH$_x$)$_{p1}$, —C(=O)—O—(CH$_x$)$_{p1}$, —(CH$_x$)$_{p1}$—C(=O)—, —(CH$_x$)$_{p1}$—C(=O)—O—, —(O—(CH$_2$)$_{p2}$—)$_{p3}$—, —((CH$_2$)$_{p2}$—O—)$_{p3}$—, —C(=S)—, —C(=S)—S—, —C(=S)—NH—, —S—C(=S)—, —S—C(=S)—S—, —S—, —SO—, —SO$_2$—, —NR$_4$—, —N(R$_4$)—C(=O)—N(R$_8$)—, —N(R$_4$)—C(=O)O—, —N(R$_4$)—C(=O)—, —C(=O)—N(R$_4$)—, —C(=O)—N(R$_4$)—C(=O)—, —O—C(=O)—N(R$_4$), —O—C(=S)—N(R$_4$)—, —C(=S)—N(R$_4$)—, —N=C=S, —N=C=O,

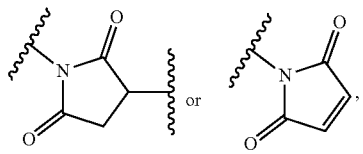 [SMILES: *C1CC(=O)N(*)C1=O ; *N1C(=O)C=CC1=O]
or wherein alkyl, alkynyl, alkenyl, cycloalkyl, aryl, heteroaryl, and heterocyclyl are optionally substituted and R$_4$, R$_5$, R$_6$ and R$_8$ are each independently H, or a substituted or unsubstituted: alkyl, alkenyl, alkynyl, aryl, heteroaryl, heterocyclyl;

Z$_1$ is represented by Formula (VIII):

$$-Z_{1A}-Z_{1B}-Z_{1C}-Z_{1D}- \quad (VIII),$$

wherein:
Z$_{1A}$, Z$_{1B}$, Z$_{1C}$ and Z$_{1D}$ are each independently absent, an amino acid, a peptide having 2-20 amino acids, an alkyl, an alkynyl, an alkenyl, a cycloalkyl, an aryl, a heteroaryl, a heterocyclyl, —CR$_5$R$_6$—, —O—, —C(=O)—, —O—C(=O)—, —C(=O)—O—, —O—C(=O)—O—, —C(=O)—(CH$_x$)$_{p1}$, —C(=O)—O—(CH$_x$)$_{p1}$, —(CH$_x$)$_{p1}$—C(=O)—, —(CH$_x$)$_{p1}$—C(=O)—O—, —(O—(CH$_2$)$_{p2}$—)$_{p3}$—, —((CH$_2$)$_{p2}$—O—)$_{p3}$—, —C(=S)—, —C(=S)—S—, —C(=S)—NH—, —S—C(=S)—, —S—C(=S)—S—, —S—, —SO—, —SO$_2$—, —NR$_4$—, —N(R$_4$)—C(=O)—N(R$_8$)—, —N(R$_4$)—C(=O)O—, —N(R$_4$)—C(=O)—, —C(=O)—N(R$_4$)—, —C(=O)—N(R$_4$)—C(=O)—, —O—C(=O)—NR$_4$—, —N=C=S, —N=C=O,

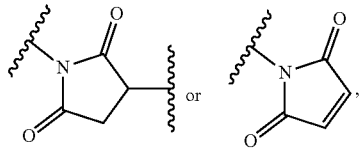 [SMILES: *C1CC(=O)N(*)C1=O ; *N1C(=O)C=CC1=O]
or wherein alkyl, alkynyl, alkenyl, cycloalkyl, aryl, heteroaryl, and heterocyclyl are optionally substituted and R$_4$, R$_5$, R$_6$, R$_8$ are each independently H, or a substituted or unsubstituted: alkyl, alkenyl, alkynyl, aryl, heteroaryl, heterocyclyl;

A is a peptide selected from the group consisting of valine-citrulline, citrulline-valine, lysine-phenylalanine, phenylalanine-lysine, valine-asparagine, asparagine-valine, threonine-asparagine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, asparagine-alanine; and X is an aryl selected from the group consisting of

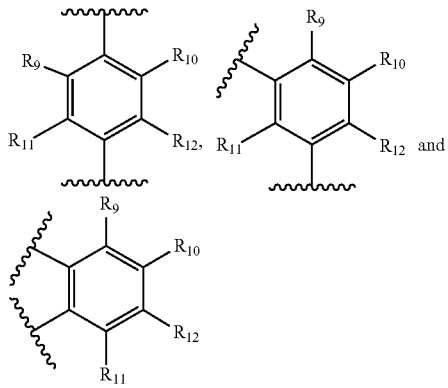

wherein R$_9$, R$_{10}$, R$_{11}$, and R$_{12}$ are each independently H, an alkyl, cycloalkyl, aryl, heteroaryl, heterocyclyl, halogen, NR$_{13}$R$_{14}$, nitro, cyano, —OH, —O—C(=O—R$_{15}$, —C(=O)—R$_{15}$, —C(=O)—O—R$_{15}$, —C(=O)—NR$_{13}$ R$_{14}$, further wherein, alkyl, cycloalkyl, aryl, heteroaryl, and heterocyclyl are optionally substituted;

R$_{13}$ and R$_{14}$ are each independently H or an optionally substituted alkyl; and R$_{15}$ is an optionally substituted alkyl.

The Biologically Active Molecules (D) can optionally be a substituted maytansinoid of Formula II:

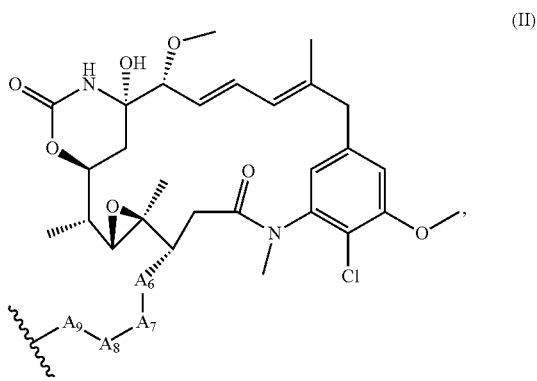

(II)

wherein:
A$_6$, A$_7$, A$_8$, A$_9$ are each independently absent, an amino acid, N-alkyl amino acid, a peptide having 2-20 amino acids, an alkyl, an alkenyl, an alkynyl, a cycloalkyl, an aryl, a heteroaryl, a heterocyclyl, —CR$_5$R$_6$—, —O—, —C(=O)—, —O—C(=O)—, —C(=O)—O—, —O—C(=O)—O—, —C(=O)—(CH$_x$)$_{p1}$, —C(=O)—O—(CH$_x$)$_{p1}$, —(CH$_x$)$_{p1}$—C(=O)—, —(CH$_x$)$_{p1}$—C(=O)—O—, —(O—(CH$_2$)$_{p2}$—)$_{p3}$—, —((CH$_2$)$_{p2}$—O—)$_{p3}$—, —C(=S)—, —C(=S)—S—, —C(=S)—NH—, —S—C(=S)—, —S—C(=S)—S—, —S—, —SO—, —SO$_2$—, —NR$_4$—, —N(R$_4$)—C(=O)—N(R$_8$)—, —N(R$_4$)—C(=O)O—, —N(R$_4$)—C(=O)—, —C(=O)—N(R$_4$)—, C(=O)—N(R$_4$)—C(=O)—, O—C(=O)—NR$_4$, further wherein alkyl, alkynyl, alkenyl, cycloalkyl, aryl, heteroaryl, and heterocyclyl are optionally substituted, and $R_4$, $R_5$, $R_6$ and $R_8$ are each independently H, or a substituted or unsubstituted: alkyl, alkenyl, alkynyl, aryl, heteroaryl, heterocyclyl.

In another embodiment, the disclosure provides compounds of formula (V), wherein the biologically active molecule is a optionally substituted maytansinoid represented by the following structural formula:

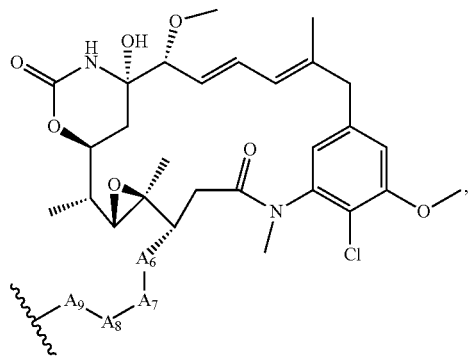

(II)

wherein:
$A_6$, $A_7$, $A_8$, $A_9$ are each independently absent, an amino acid, N-alkyl amino acid, a peptide having 2-20 amino acids, an alkyl, an alkenyl, an alkynyl, a cycloalkyl, an aryl, a heteroaryl, a heterocyclyl, —$CR_5R_6$—, —O—, —C(=O)—, —O—C(=O)—, —C(=O)—O—, —O—C(=O)—O—, —C(=O)—(CH$_x$)$_{p1}$, —C(=O)—O—(CH$_x$)$_{p1}$, —(CH$_x$)$_{p1}$—C(=O)—, —(CH$_x$)$_{p1}$—C(=O)—O—, —(O—CH$_2$)$_{p2}$—)$_{p3}$, —((CH$_2$)$_{p2}$—O—)$_{p3}$—, —C(=S)—, —C(=S)—S—, —C(=S)—NH—, —S—C(=S)—, —S—C(=S)—S—, —S—, —SO—, —SO$_2$—, —NR$_4$—, —N(R$_4$)—C(=O)—N(R$_8$)—, —N(R$_4$)—C(=O)O—, —N(R$_4$)—C(=O)—, —C(=O)—N(R$_4$)—, C(=O)—N(R$_4$)—C(=O)—, O—C(=O)—NR$_4$, further wherein alkyl, alkynyl, alkenyl, cycloalkyl, aryl, heteroaryl, and heterocyclyl are optionally substituted, and $R_4$, $R_5$, $R_6$ and $R_8$ are each independently H, or a substituted or unsubstituted: alkyl, alkenyl, alkynyl, aryl, heteroaryl, heterocyclyl.

In yet another embodiment, the disclosure provides compounds of formula (V), wherein the biologically active molecule is a maytansinoid represented by the following structural formula:

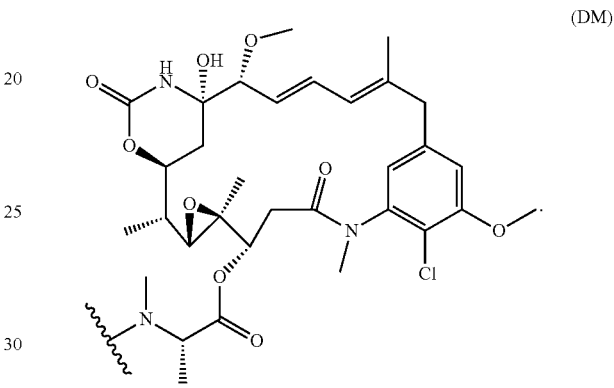

(DM)

In one embodiment, the disclosure provides compounds of formula (V) represented by the following structures: (V)(a), (V)(b), (V)(c), (V)(d), and (V)(e):

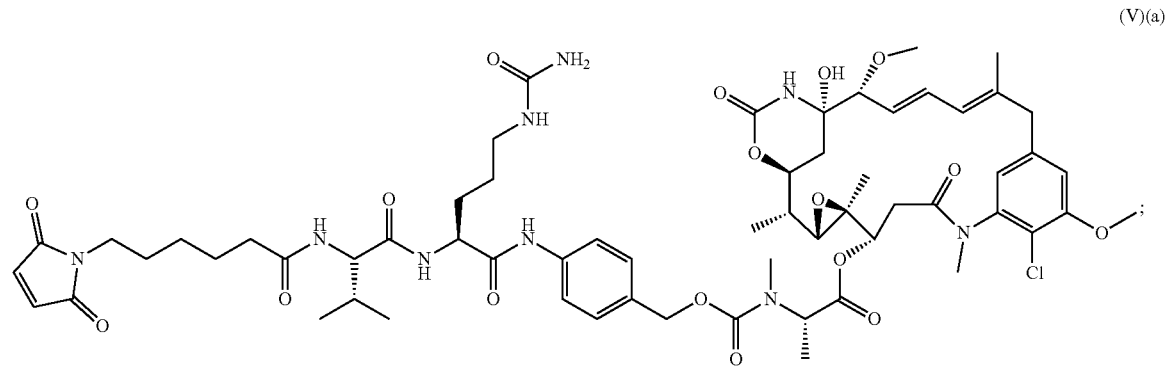

(V)(a)

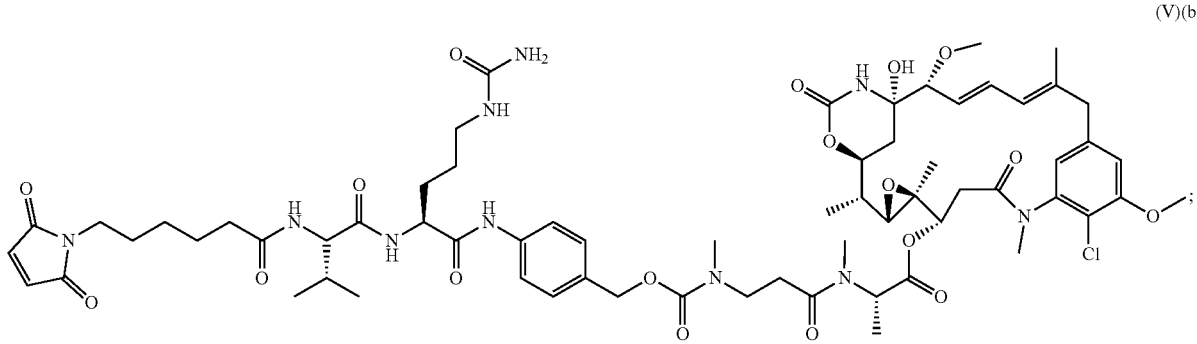

(V)(b)

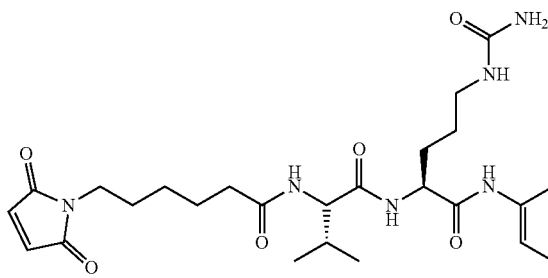
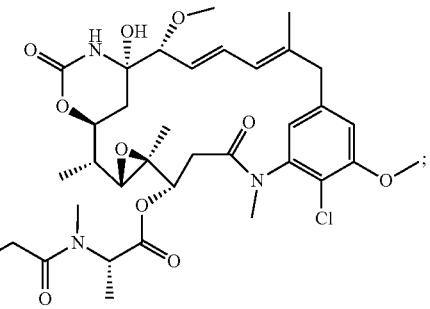

(V)(c)

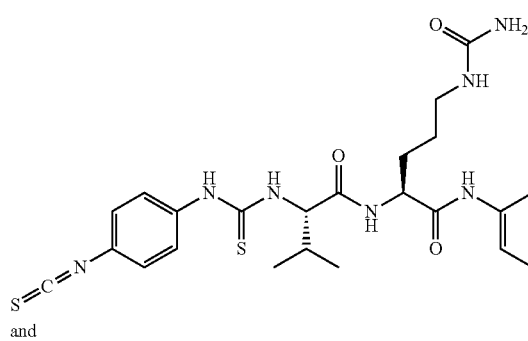
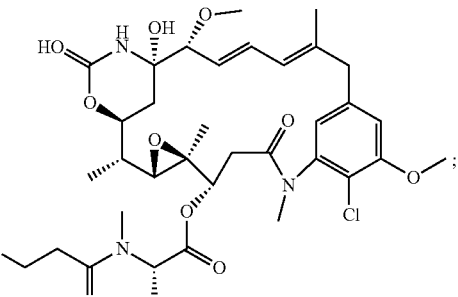

(V)(d)

and

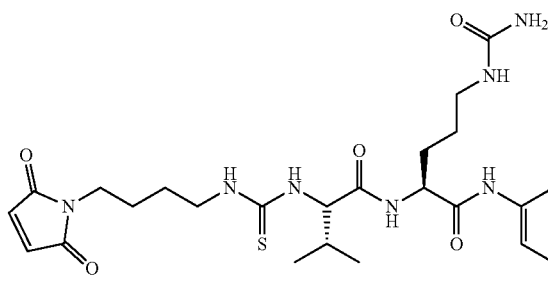
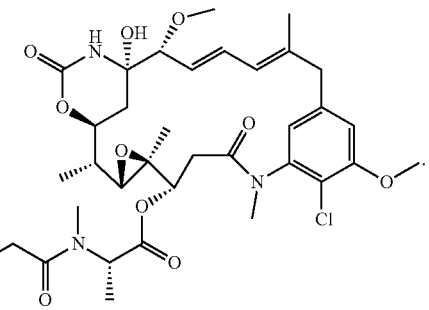

(V)(e)

In one aspect, the disclosure provides the compounds of formula (IX):

Y₁—Z₁-D    (IX)

wherein:
D is a Biologically Active Molecule;
Y₁ is

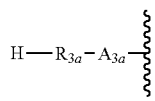

wherein $R_{3a}$ and $A_{3a}$ are each independently absent, an amino acid, a peptide having 2-20 amino acids, an alkyl, an alkynyl, an alkenyl, a cycloalkyl, an aryl, a heteroaryl, a heterocyclyl, —CR₅R₆—, —O—, —C(=O)—, —O—C(=O)—, —C(=O)—O—, —O—C(=O)—O—, —C(=O)—(CH$_x$)$_{p1}$—, —C(=O)—O—(CH$_x$)$_{p1}$—, —(CH$_x$)$_{p1}$—C(=O)—, —(CH$_x$)$_{p1}$—C(=O)—O—, —(O—(CH₂)$_{p2}$—)$_{p3}$—, —((CH₂)$_{p2}$—O—)$_{p3}$—, —C(=S)—, —C(=S)—S—, —C(=S)—NH—, —S—C(=S)—, —S—C(=S)—S—, —S—, —SO—, —SO₂—, —NR₄—, —N(R₄)—C(=O)—N(R₈)—, —N(R₄)—C(=O)—, —C(=O)—N(R₄)—, —C(=O)—N(R₄)—C(=O)—, —O—C(=O)—NR₄—, wherein alkyl, alkynyl, alkenyl, cycloalkyl, aryl, heteroaryl, and heterocyclyl are optionally substituted; and Z₁ is represented by following structural formula:

—Z$_{1A}$—Z$_{1B}$—Z$_{1C}$—Z$_{1D}$—, wherein:
Z$_{1A}$, Z$_{1B}$, Z$_{1C}$ and Z$_{1D}$ are each independently absent, an amino acid, a peptide having 2-20 amino acids, an alkyl, an alkynyl, an alkenyl, a cycloalkyl, an aryl, a heteroaryl, a heterocyclyl, —CR₅R₆—, —O—, —C(=O)—, —O—C(=O)—, —C(=O)—O—, —O—C(=O)—O—, —C(=O)—(CH$_x$)$_{p1}$, —C(=O)—O—(CH$_x$)$_{p1}$, —(CH$_x$)$_{p1}$—C(=O)—, —(CH$_x$)$_{p1}$—C(=O)—O—, —(O—(CH₂)$_{p2}$—)$_{p3}$—, —((CH₂)$_{p2}$—O—)$_{p3}$—, —C(=S)—, —C(=S)—S—, —C(=S)—NH—, —S—C(=S)—, —S—C(=S)—S—, —S—, —SO—, —SO₂—, —N(R₄)—C(=O)—

—N(R$_8$)—, —N(R$_4$)—C(=O)O—, —N(R$_4$)—C(=O)—, —C(=O)—N(R$_4$)—, C(=O)—N(R$_4$)—C(=O)—, —O—C(=O)—N(R$_4$), —O—C(=S)—N(R$_4$)—, —C(=S)—N(R$_4$)—, —N=C=S, —N=C=O,

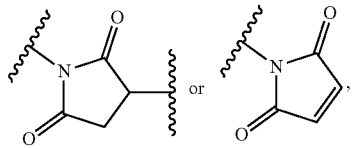 [SMILES: *C1CC(=O)N(*)C1=O ; *N1C(=O)C=CC1=O]

wherein alkyl, alkynyl, alkenyl, cycloalkyl, aryl, heteroaryl, and heterocyclyl are optionally substituted and R$_4$, R$_5$, R$_6$ and R$_8$ are each independently H, or a substituted or unsubstituted: alkyl, alkenyl, alkynyl, aryl, heteroaryl, or heterocyclyl.

In another aspect, the disclosure provides compound of formula (IX) wherein the Biologically Active Molecule is a cytotoxic biologically active macrolide. In yet another aspect, the disclosure provides compound of formula (IX) wherein the biologically active macrolide is a maytansinoid. In a further aspect, the disclosure provides compound of formula (IX) wherein the maytansinoid is represented by formula (II). In another aspect, the disclosure provides compound of formula (IX) wherein the maytansinoid is represented by formula (II)(a).

In an aspect, the disclosure provides a compound of formula (IX) wherein IC$_{50}$ of the compound is greater than about 10 nM.

In an aspect, the disclosure provides a compound of formula (IX) wherein the compound is about 10 fold less cytotoxic than the corresponding compound of formula (I).

In another one aspect, the disclosure provides compounds of formula (X):

$$\text{Ab}-\overset{H}{N}-(Z_2-A-W-X-Y-Z_1-DM)_a \quad (X)$$

wherein:

Ab is an antibody or a fragment thereof;

a is an integer from 1 to 10;

Z$_2$ and Z$_1$ are each independently absent or a spacer;

A is a natural or non-natural amino acid, or a peptide comprising 2-20 amino acids;

W is absent, —O—, —S—, —CR$_5$R$_6$—, —NR$_4$—;

X is absent, aryl, heteroaryl, cycloalkyl, heterocyclyl, wherein aryl, heteroaryl, cycloalkyl, and heterocyclyl are optionally substituted;

Y is absent,

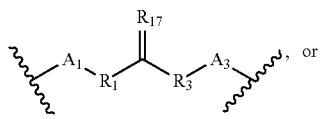, or

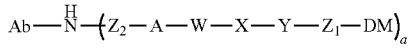, wherein A$_1$, A$_3$, R$_1$ and R$_3$ are each independently absent, an amino acid, a peptide having 2-20 amino acids, an alkyl, an alkynyl, an alkenyl, a cycloalkyl, an aryl, a heteroaryl, a heterocyclyl, —CR$_5$R$_6$—, —O—, —C(=O)—, —O—C(=O)—, —C(=O)—O—, —O—C(=O)—O—, —C(=O)—(CH$_x$)$_{p1}$—, —C(=O)—O—(CH$_x$)$_{p1}$—, —(CH$_x$)$_{p1}$—C(=O)—, —(CH$_x$)$_{p1}$—C(=O)—O—, —(O—(CH$_2$)$_{p2}$—)$_{p3}$—, —((CH$_2$)$_{p2}$—O—)$_{p3}$—, —C(=S)—, —C(=S)—S—, —C(=S)—NH—, —S—C(=S)—, —S—C(=S)—S—, —S—, —SO—, —SO$_2$—, —NR$_4$—, —N(R$_4$)—C(=O)—N(R$_8$)—, —N(R$_4$)—C(=O)O—, —N(R$_4$)—C(=O)—, —C(=O)—N(R$_4$)—, —C(=O)—N(R$_4$)—C(=O)—, —O—C(=O)—NR$_4$—, wherein alkyl, alkynyl, alkenyl, cycloalkyl, aryl, heteroaryl, and heterocyclyl are optionally substituted;

A$_4$ and A$_5$ are each independently —O—, —S—, —NR$_{18}$—, —CR$_5$R$_6$—;

R$_{17}$ is selected from the group consisting of O, S, NR$_{18}$, CR$_5$R$_6$;

R$_{18}$ is selected from the group consisting of H, alkyl, alkynyl, alkenyl, cycloalkyl, aryl, heteroaryl, heterocyclyl, and acyl, wherein alkyl, alkynyl, alkenyl, cycloalkyl, aryl, heteroaryl, heterocyclyl, and acyl are optionally substituted;

R$_4$, R$_5$, R$_6$ and R$_8$ are each independently H, or a substituted or unsubstituted: alkyl, alkenyl, alkynyl, aryl, heteroaryl, or heterocyclyl;

p1, p2 and p3 are each independently 0, or an integer from 1 to 100;

x is 0, 1 or 2; and

DM is represented by the following structure:

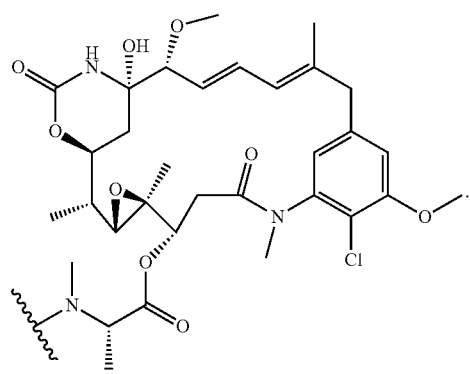 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In one embodiment, the disclosure provides the compound of formula (X) represented by the following structure (X)(a):

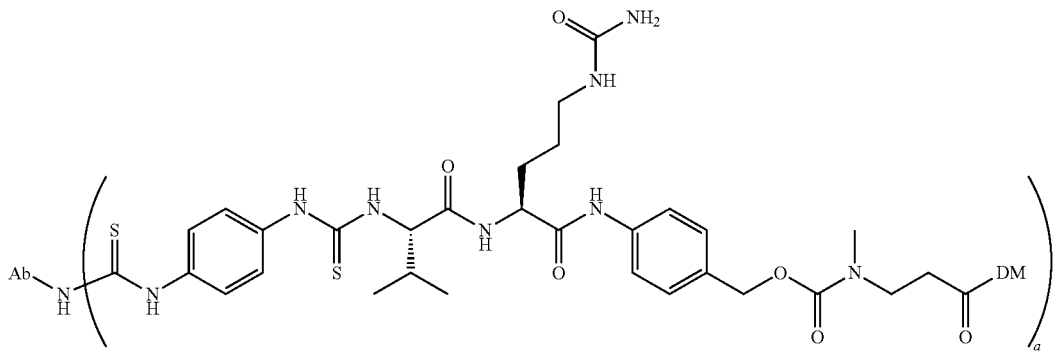

wherein a is an integer from 1 to 10.
In another aspect, the disclosure provides the compound of formula (XI):

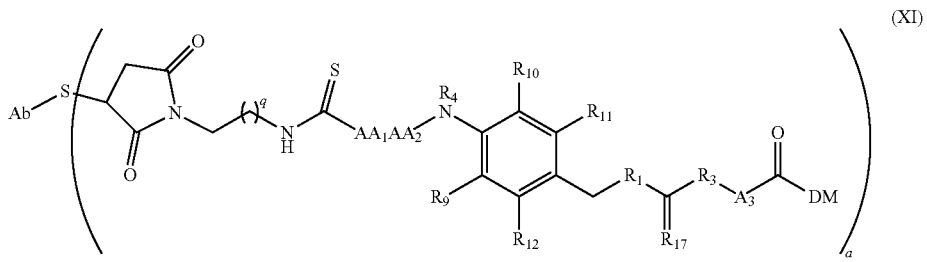

wherein:
Ab is an antibody or a fragment thereof;
AA$_1$-AA$_2$ is a peptide selected from the group consisting of valine-citrulline, citrulline-valine, lysine-phenylalanine, phenylalanine-lysine, valine-asparagine, asparagine-valine, threonine-asparagine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, asparagine-alanine;
a is an integer from 1 to 10;
q is 0 or an integer from 1 to 5;
A$_3$, R$_1$ and R$_3$ are each independently absent, an amino acid, a peptide having 2-20 amino acids, an alkyl, an alkynyl, an alkenyl, a cycloalkyl, an aryl, a heteroaryl, a heterocyclyl, —CR$_5$R$_6$—, —O—, —C(=O)—, —O—C(=O)—, —C(=O)—O—, —O—C(=O)—O—, —C(=O)—(CH$_x$)$_{p1}$—, —C(=O)—O—(CH$_x$)$_{p1}$—, —(CH$_x$)$_{p1}$—C(=O)—, —(CH$_x$)$_{p1}$—C(=O)—O—, —(O—(CH$_2$)$_{p2}$—)$_{p3}$—, —((CH$_2$)$_{p2}$—O—)$_{p3}$—, —C(=S)—, —C(=S)—S—, —C(=S)—NH—, —S—C(=S)—, —S—C(=S)—S—, —S—, —SO—, —SO$_2$—, —NR$_4$—, —N(R$_4$)—C(=O)—N(R$_8$)—, —N(R$_4$)—C(=O)O—, —N(R$_4$)—C(=O)—, —C(=O)—N(R$_4$)—, —C(=O)—N(R$_4$)—C(=O)—, —O—C(=O)—NR$_4$—, wherein alkyl, alkynyl, alkenyl, cycloalkyl, aryl, heteroaryl, and heterocyclyl are optionally substituted;
R$_{17}$ is selected from the group consisting of O, S, NR$_{18}$, CR$_5$R$_6$;

R$_4$, R$_5$, R$_6$ and R$_8$ are each independently H, or a substituted or unsubstituted: alkyl, alkenyl, alkynyl, aryl, heteroaryl, and heterocyclyl;

R$_9$, R$_{10}$, R$_{11}$, and R$_{12}$ are each independently H, halogen, NR$_{13}$R$_{14}$, nitro, cyano, —OH, —O—C(=O)—R$_{15}$, —C(=O)—R$_{15}$, —C(=O)—O—R$_{15}$, —C(=O)—NR$_{13}$R$_{14}$, substituted or unsubstituted: alkyl, cycloalkyl, aryl, heteroaryl, and heterocyclyl;
R$_{13}$ and R$_{14}$ are each independently H or an optionally substituted alkyl; and R$_{15}$ is an optionally substituted alkyl;
p1, p2 and p3 are each independently 0, or an integer from 1 to 100;
x is 0, 1 or 2; and
DM is represented by the following structure:

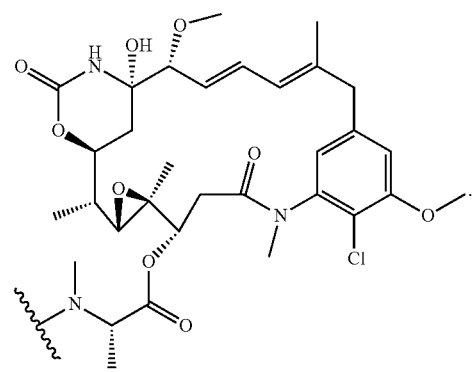 [SMILES: *N(C)[C@@H](C)C(=O)O[C@H]1CC(=O)N(C)c2cc(cc(OC)c2Cl)C/C(C)=C/C=C/[C@@H](OC)[C@@]2(O)C[C@H](OC(=O)N2)[C@@H](C)[C@@H]2O[C@@]12C]

In one embodiment, the disclosure provides the compound of formula (XI) represented by the following structure (XI)(a):

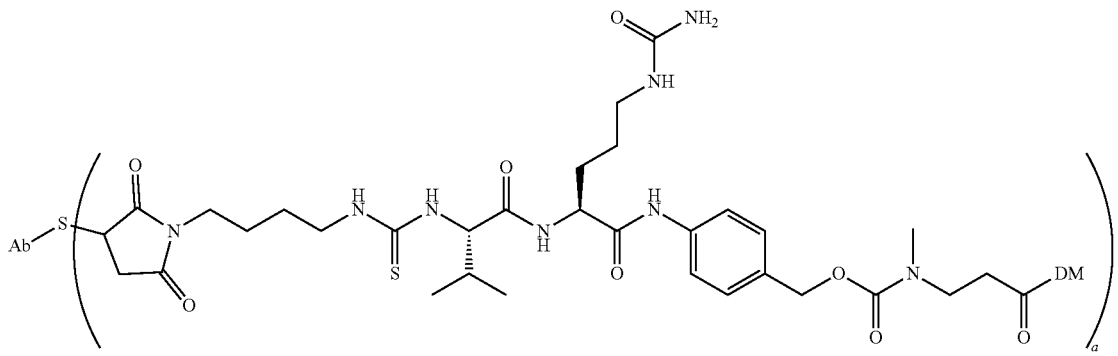

(XI)(a)

wherein a is an integer from 1 to 10.

In one aspect, the disclosure provides the compounds of formula (I), (III), (IV) (V), and (X), wherein A is a peptide cleavable by a protease.

In one aspect, the disclosure provides the compound of formula (XI) wherein the peptide is cleavable by a protease.

In one aspect, the disclosure provides the compounds of formula (I), (III), (IV) (V), and (X) wherein A is a peptide cleavable by a protease expressed in tumor tissue.

In one aspect, the disclosure provides the compound of formula (XI) wherein the peptide is cleavable by a protease expressed in tumor tissue.

In an embodiment, the disclosure provides the compounds of formula (I), (III), (IV) (V), (X) wherein A is a peptide cleavable by a protease further wherein the protease is a cathepsin or a plasmin.

In an embodiment, the disclosure provides the compound of formula (XI) wherein the peptide is cleavable by a protease further wherein the protease is a cathepsin or a plasmin.

Compositions

Embodiments herein include compositions comprising conjugate compounds of formula (I), (III), (IV), (V), (X), or (XI) as well as mixtures thereof. In some aspects the compound is further represented by a compound of formula (III)(a), (III)(b), (IV)(a), (V)(a), (V)(b), (V)(c), (V)(d) (V)(e), (X)(a), or (XI)(a).

Embodiments herein include compositions comprising compounds of formula (I), (III), (IV), (V), (IX), (X), or (XI) as well as mixtures thereof.

Compositions may be pharmaceutical compositions that further include one or more pharmaceutically acceptable carriers, diluents, and/or excipients. In some aspects the pharmaceutical composition is the pharmaceutically acceptable salt of compounds of formula (I), (III), (IV), (V), (IX), (X), or (XI) or mixtures thereof. In some other aspects the pharmaceutical composition is the pharmaceutically acceptable salt of compounds of formula (I), (III), (IV), (V), (IX), (X), or (XI) or mixtures thereof.

Suitable pharmaceutical acceptable carriers, diluents and excipients are well known in the art and can be determined by one of ordinary skill in the art as the clinical situation warrants. Examples of suitable carriers, diluents and excipients include: buffers for maintenance of proper composition pH (e.g., citrate buffers, succinate buffers, acetate buffers, phosphate buffers, lactate buffers, oxalate buffers and the like), carrier proteins (e.g., human serum albumin), saline, polyols (e.g., trehalose, sucrose, xylitol, sorbitol, and the like), surfactants (e.g., polysorbate 20, polysorbate 80, polyoxolate, and the like), antimicrobials, and antioxidants.

If so desired, the pharmaceutical compositions herein may include a second or more therapeutic agent (e.g., an adjuvant to the conjugate compounds of formula (I), (III), (IV), (X), and/or (XI), anti-tumor agents, antibiotics, anti-inflammatories, and the like). The second therapeutic agent can be included in the same composition as the compounds of formula (I), (III), (IV), (V), (IX), (X), and/or (XI), or can be administered separately from the compounds of formula (I), (III), (IV), (V), (IX), (X), and/or (XI) (by time, or type and location of administration).

One of skill in the art of Biologically Active Molecules will understand that each of the compounds of formula (I), (III), (IV), (V), (IX), (X), and/or (XI) can be modified in such a manner that the resulting compound still retains specificity and/or activity similar to the starting compound. In this light, the Biologically Active Molecule (D) of compounds of formula (I), (III), (IV), (V), (IX), (X), and/or (XI) can include any and all of the Biologically Active Molecules' analogues and derivatives. In one embodiment the Biologically Active Molecules is a macrolide and further is maytansine or an analogue of maytansine as described in Widdison et al., J. Med. Chem., 2006, 49 (14), 4392-4408.

In one aspect, the disclosure provides the pharmaceutical composition comprising a therapeutically effective amount of a compound of formula (I), (III), (IV), (X), (XI) including (III)(a), (III)(b) (IV)(a), (X)(a), and (XI)(a), or a pharmaceutically acceptable salt thereof and one or more pharmaceutically acceptable carriers, diluents, or excipients.

In one aspect, the disclosure provides the pharmaceutical composition comprising a therapeutically effective amount of a compound of formula (I), (III), (IV), (V), (IX), (X), (XI) including (III)(a), (III)(b) (IV)(a), (V)(a), (V)(b), (V)(c), (V)(d), and (V)(e), (X)(a), and (XI)(a), or a pharmaceutically acceptable salt thereof and one or more pharmaceutically acceptable carriers, diluents, or excipients.

In another aspect, the disclosure provides pharmaceutical composition comprising a therapeutically effective amount of a compound of formula (V) including (V)(a), (V)(b), (V)(c), (V)(d), and (V)(e), or a pharmaceutically acceptable salt thereof and one or more pharmaceutically acceptable carriers, diluents, or excipients.

In another aspect, the disclosure provides pharmaceutical composition comprising a therapeutically effective amount of a compound of formula (IX), or a pharmaceutically acceptable salt thereof and one or more pharmaceutically acceptable carriers, diluents, or excipients.

In another aspect, the disclosure provides pharmaceutical composition comprising a therapeutically effective amount of a compound of formula (V) and (IX) including (V)(a), (V)(b), (V)(c), (V)(d), and (V)(e), or a pharmaceutically acceptable salt thereof and one or more pharmaceutically acceptable carriers, diluents, or excipients.

Method of Use

As described above, conjugate compounds of formula (I), (III), (IV), (X), and (XI) can be produced with various functional groups such that attachment of the Ligand (L) to the linker and thereby a Biologically Active Molecule form a covalent conjugate. The Ligand specially targets the conjugate compound to the Ligand binding partner, typically a polypeptide or other like antigen. In typical embodiment, the conjugate is designed to include a Ligand having a binding partner found on cells undergoing abnormal cell growth or cells involved in a proliferative disorder. Surprisingly, conjugate compounds of formula (I), (III), (IV), (X), and (XI) have been designed such that each compound's linker is catabolized inside the cell bound by the conjugate. As such, delivery of a Biologically Active Molecule through the conjugate embodiments herein allows for delivery of Biologically Active Molecules that would normally be too toxic to administer conventionally. The embodiments herein allow for highly selective and specific delivery of these molecules to cells undergoing abnormal cell growth or cells involved in proliferative disorders (as compared to catabolism outside the cell, thereby releasing the biologically active compound into the blood or lymphatic system, for example).

As can be envisioned by one of skill in the art, the covalent conjugate compounds described herein can also be used to deliver any type of useful Biologically Active Molecule and can be selectively targeted to any type of cell population, for example, the conjugate may be used to deliver anti-proliferative drugs to cells undergoing abnormal growth or anti-viral drugs to cells infected with a virus, as long as the selected Ligand recognizes a proper cell binding partner.

In this light, methods of use are provided for the conjugate compound embodiments described herein.

The pharmaceutical compositions described herein are useful in inhibiting, retarding and/or preventing abnormal cell growth or in the treatment of various proliferative disorders or disease states in mammals. In typical embodiments the mammal is a human (embodiments herein will be described in relation to humans). Other mammals include any mammal that can suffer from a detectable proliferative disorder, including primates, dogs, cats, horses, goats, sheep, cattle, camels, and the like. In addition, it is understood that the conjugate compounds of the pharmaceutical compositions are designed for selective targeting to the cells undergoing abnormal cell growth or for the treatment of the various proliferative disorders or disease states described herein.

As such, embodiments herein include methods of inhibiting abnormal cell growth or treatment of a proliferative disorder in a human comprising administering to the human a therapeutically effective amount of a pharmaceutical composition described herein.

Administration of a therapeutically effective amount of a pharmaceutical composition described herein may be effected in different ways, e.g., by intravenous, intraperitoneal, subcutaneous, intramuscular, topical, intradermal, intranasal, or intrabronchial administration. The pharmaceutical compositions herein may also be administered directly to an abnormal cell growth site (directly or indirectly contacting the abnormal cell growth) by, for example, biolistic delivery (biolistic delivery of the pharmaceutical compositions herein to a lung or brain tumor, for example). Dosage regiments for administration of the pharmaceutical compositions herein will be determined by the attending health care professional or other person of skill in the art as well as based on the particular clinical situation. As is well known in the pharmaceutical arts, dosages for any one human, i.e., patient, depends on a number of factors, including patient size, patient's body surface area, patient's age and general health, patient's sex, the time and route of administration, and presence of a second therapeutic agent. In some instances the conjugate compounds of formula (I), (III), (IV), (X), and/or (XI) may be present in amounts between 1 µg and 100 mg/kg body weight per dose (note that where continuous infusion is considered as an administration route, as little as 1 pg/kg body weight per minute may be considered). Pharmaceutical compositions can be administered one or more times a day and over a period of days, weeks, months, or years.

Treatment of proliferative disorder or disease, for example a tumor, includes methods of reducing a tumor size, causing necrosis or apoptosis in a tumor, killing a tumor, stopping a tumor from increasing in size and/or preventing invasiveness or metastasis of a tumor.

Examples of medical conditions that can be treated according to methods of inhibiting abnormal cell growth, or treating proliferative disorders include: malignancy of any type, e.g., cancer of the lung, colon, prostate, kidney, pancreas, liver, ovary, skin, lymphoma, leukemia and the like; autoimmune diseases, e.g., systemic lupus, rheumatoid arthritis, multiple sclerosis; viral infections, e.g., CMV infection, HIV infection, AIDS, Hepatitis, HPV infection; pain; mental disorders; and inflammatory diseases.

As noted above, pharmaceutical compositions described herein are also useful in the prevention or treatment of viral infections, pain, inflammatory diseases, autoimmune diseases, and the like in a mammal.

In one aspect, the disclosure provides a method of reducing, retarding or stopping an abnormal cell growth comprising contacting the abnormal cell with a compound of formula (I), (III) (IV), (X), and/or (XI) in an amount sufficient to retard, reduce or stop the abnormal cell growth, and wherein the abnormal cell growth is retarded, reduced or stopped.

In one aspect, the disclosure provides a method of killing a cell, comprising contacting the cell with a compound of formula (I), (III), (IV), (X), and/or (XI) in an amount sufficient to kill the cell, and wherein the cell is killed.

In one embodiment, the disclosure provides a method of killing a cell, comprising contacting the cell with a compound of formula (I), (III), (IV), (X), and/or (XI) in an amount sufficient to kill the cell, and wherein the cell is killed and further wherein the cell is a tumor cell.

In one aspect, the disclosure provides a method of treatment of a medical disorder in an individual suffering from the medical disorder, comprising administering to the individual an effective amount of a composition comprising a compound of formula (I), (III), (IV), (X), and/or (XI).

In one other aspect, the disclosure provides a method of treatment of a medical disorder in an individual suffering from the medical disorder, comprising administering to the individual an effective amount of a composition comprising a compound of formula (I), (III), (IV), (V), (IX), (X), and/or (XI).

In one embodiment, the disclosure provides a method of treatment of a medical disorder in an individual suffering from the medical disorder comprising administering to the individual an effective amount of a composition comprising a compound of formula (I), (III), (IV), (X), and/or (XI) and further comprising administering sequentially or consecutively an additional therapy.

In one embodiment, the disclosure provides methods, wherein additional therapy is radiation therapy, chemotherapy, or a combination of both.

In one embodiment, the disclosure provides a method of treatment of a medical disorder in an individual suffering from the medical disorder comprising administering to the individual an effective amount of a composition comprising a compound of formula (I), (III), (IV), (X), and/or (XI) and further comprising administering sequentially or consecutively an additional therapy and administering at least one additional therapeutic agent.

In one embodiment, the disclosure provides a method of treatment of a medical disorder in an individual suffering from the medical disorder comprising administering to the individual an effective amount of a composition comprising a compound of formula (I), (III), (IV), (X), and/or (XI) and further comprising administering sequentially or consecutively an additional therapy or administering at least one additional therapeutic agent.

In one aspect, the medical disorder treated is selected from tumors, cancers, infectious diseases, neurodegenerative diseases, bone disorders, and cardiovascular diseases.

Embodiments herein also provide methods of preparing compounds of formula (I) from precursor or building block compounds of formula (V). In some aspects the compounds of formula (V) can also be used in therapeutic application where the compound of formula (V) is a pharmaceutical composition. In some aspects compounds of formula (V) can be included in any of the compositions or pharmaceutical compositions of compound (I), (III), (IV), (IX), (X), and/or (XI).

Finally, embodiments herein may include mixtures of compounds as represented by formula (I), (III), (IV), (V), (IX), (X), and/or (XI).

Production of Conjugates

The Ligand-Biologically Active Molecule conjugate compounds can be generated by any technique known to the skilled artisan. The Ligand-Biologically Active Molecule conjugate compounds comprise a Ligand unit, a Biologically Active Molecule, and optionally a Linker that joins the Biologically Active Molecule and the Ligand. The covalent attachment of Biologically Active Molecules and/or Linkers to the Ligand can be accomplished using variety of reactions using the amino acid residues of the Ligand, e.g., antibody, including the amine groups of lysine, the free carboxylic acid groups of glutamic and aspartic acid, the sulfhydryl groups of cysteine and the various moieties of the aromatic amino acids.

Further, conjugates in accordance with various embodiments described herein can be prepared by any known method in the art. An illustrative protocol for producing conjugates is provided in the Examples below. However, other known methods can be used, including, for example, protocols described in WO 2009/134977, U.S. Pat. Nos. 7,811,572 and 6,441,163, as long as the protocols are used to prepare the compounds as described herein. These references are incorporated by reference for their intended purpose.

In one embodiment, the conjugates can be prepared by i) reacting a Ligand with Linker to form a modified Ligand-Linker compound; ii) optionally purifying the Ligand-Linker compound; iii) conjugating a Biologically Active Molecule, e.g., a macrolide, to the Ligand-Linker to form a conjugate of formula (I), (III), (IV), (X), or (XI); and iv) purifying the conjugate.

In an alternative embodiment, the conjugates can be prepared by reacting a Biologically Active Molecule with a first component of the Linker ($Z_1$), followed by successive reactions to build out the Linker, including addition of Y, X, W, A and $Z_2$, or any combination thereof.

In an alternative embodiment, the conjugates are prepared by reacting a Ligand, Linker and biologically active macrolide in a single reaction. Once the conjugates in accordance with the invention are prepared they can be purified.

Identifying Cytotoxicity of Conjugate Compounds

In one embodiment, the conjugate compounds described herein can be evaluated for their ability to suppress proliferation of various cancer cell lines in vitro. The in vitro cytotoxicity assays can be conducted using methods known in the art (see Widdison et al., J. Med. Chem., 2006, 49(14), 4392-408) and as illustrated in Example 7 herein. For example, conjugate compounds can be applied to in vitro plated cancer cells for a predetermined number of days and surviving cells measured in assays by known methods. Proper controls can be utilized to ensure validity of results as can $IC_{50}$ values. Examples of in vitro potency of conjugate compounds herein can be seen in FIGS. 1 and 2. Additional in vivo efficacy can be used to confirm proposed conjugate compound potency—for example using a nude mouse model.

The above specification, examples and data provide a complete description of the manufacture and use of the composition of the invention. Since many embodiments of the invention can be made without departing from the spirit and scope of the invention, the invention resides in the claims hereinafter appended.

All references cited herein and in the Examples that follow are expressly incorporated by reference in their entireties.

The description and Examples presented infra are provided to illustrate the subject invention. One of skill in the art will recognize these Examples are provided by way of illustration only and are not included for the purpose of limiting the invention.

EXAMPLES

Experimental Details

Proton NMR spectra (for compounds that could not be detected by UV) were acquired on a Varian Inova 300 MHz instrument, while mass spectra were collected on an Agilent 1100 series LC/MSD with electrospray ionization source and triple-quad ion trap analyzer. Appropriate conjugates were analyzed using a Bruker ultraFleXtreme MALDI-TOF-TOF mass spectrometer. All starting materials and solvents were purchased commercially and used without purification, unless otherwise noted.

Example 1

Step 1: Maytansin-3-N-methyl-L-alanine (2)

The title compound was prepared as a gold solid from maytansinol (1) using the methods described in U.S. Patent Application 2007/0037972 A1. MS (ESI, pos.): calc'd for $C_{32}H_{44}ClN_3O_9$, 649.3; found 650.6 (M+H).

Step 2: Maytansin-3-N-methyl-L-(S)-alanine-N-[4-(amino-citrulline-valine-hexanamide-6-maleimidyl) benzyl]carbamate (3)

The product of the preceding step (2, 0.020 g, 0.031 mmol) and p-NO$_2$-Ph-carbonato-Bn-Cit-Val-maleimide (MA-VC-PAB-PNP, 0.027 g, 0.037 mmol; Concortis Biosystems) were dissolved in N,N-dimethylformamide (DMF, ca. 0.25 mL) in a conical vial, treated with Brockmann I basic alumina (0.10 g), the vial purged with argon, and the reaction stirred at ambient temperature for 4 days. The mixture was then filtered, the solids washed with acetonitrile/water, and filtrate purified directly on a 5u, 30×150 mm Phenomenex Gemini C18 column via HPLC (30-90% acetonitrile in water, 0.1% TFA in both, over 25 min, 15 mL/min). Lyophilization of the purest fractions overnight gave the title compound as a pale yellow solid (0.021 g, 55%). MS (ESI, pos.): calc'd for $C_{61}H_{82}ClN_9O_{10}7$, 1247.6; found 1248.8 (M+H), 1270.7 (M+Na), 1231.5 (M–H$_2$O+H).

Step 2: Maytansin-3-N-methyl-L-(S)-alanine-Boc-β-Ala (5)

The product of the preceding step (4, 0.45 g, 1.51 mmol) and maytansin-3-N-methyl-L-alanine (2, 0.30 g, 0.23 mmol) were dissolved in 3:1 acetonitrile:water (8 mL), treated with 1M aqueous NaHCO$_3$ (0.5 mL), and stirred at ambient temperature for 18 h. When the reaction was complete by TLC, it was then stirred with brine for 10 min and extracted thrice with ethyl acetate (EtOAc). The combined organic layers were then dried over Na$_2$SO$_4$, filtered, and the filtrate concentrated and dried in vacuo to a gold syrup that was purified by flash column chromatography on a 20 g silica gel cartridge (0-10% MeOH in EtOAc over 15 min) giving the title compound as a white solid (0.084 g, 43%). MS (ESI, pos.): calc'd for $C_{41}H_{59}ClN_4O_{12}$, 834.4; found 835.2 (M+H), 857.2 (M+Na), 817.4 (M–H$_2$O+H).

Step 3: Maytansin-3-N-methyl-L-(S)-alanine-β-Ala (6)

The product of the preceding step (5, 0.080 g, 0.095 mmol) was dissolved in a 3:1:1 mixture of acetonitrile/

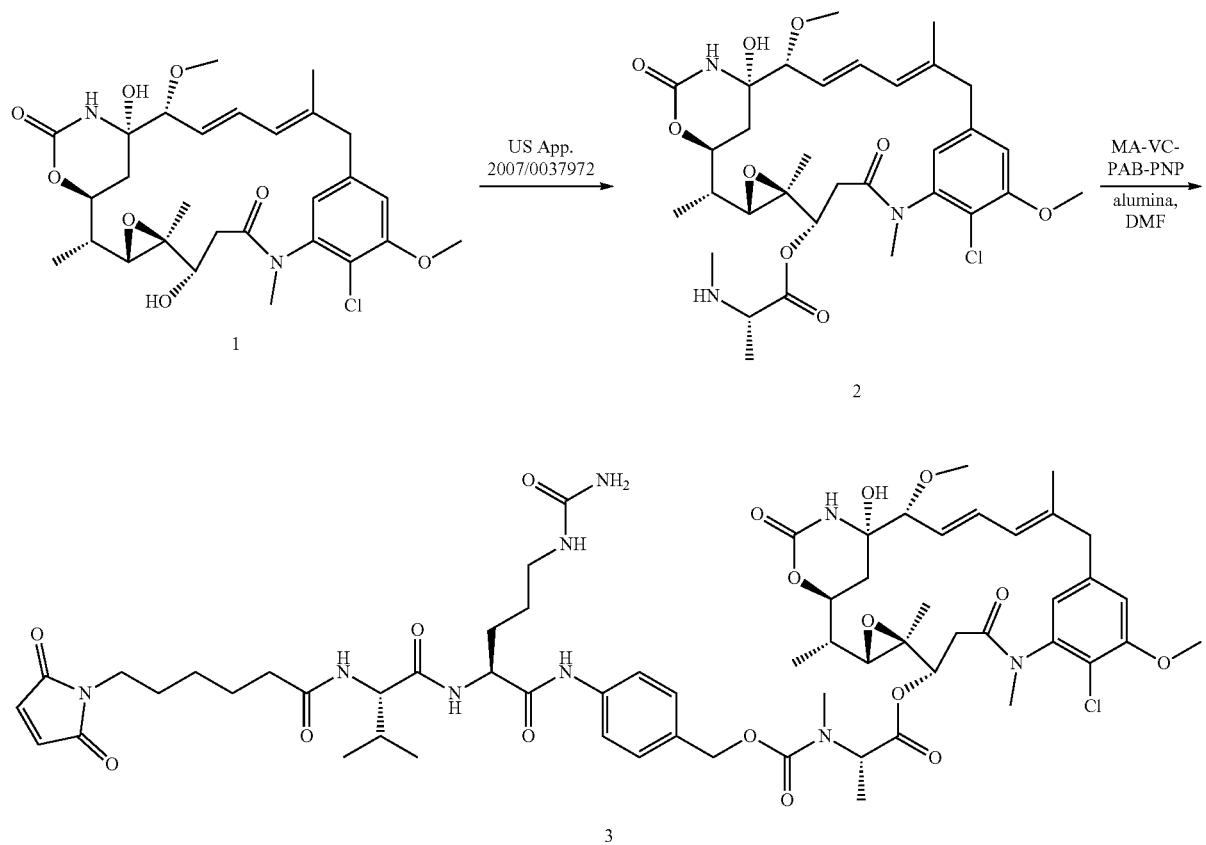

Example 2

Step 1: N-tert-Butoxycarbonyl-beta-alanine succinate ester (4)

The title compound was prepared from commercial Boc-β-alanine by a method well known in the art (cf.—Widdison et al., J. Med. Chem., 2006, 49 (14), 4401). $^1$H NMR (300 MHz, CDCl$_3$): δ 3.62 (bm, 2H), 2.88 (m, 9H), 1.47 (s, 9H).

water/trifluoroacetic acid (4 mL) and stirred at ambient temperature for 26 hours. The crude reaction mixture was injected directly onto a 40 g C18 silica gel column and eluted via ISCO CombiFlash (10-90% acetonitrile in water, 0.1% TFA in each solvent, over 18 min, 40 mL/min), and the combined pure fractions were lyophilized to give the title compound as a pale yellow solid (0.025 g, 31%). MS (ESI, pos.): calc'd for $C_{36}H_{51}ClN_4O_{10}$, 734.3; found 735.5 (M+H).

Step 4: Maytansin-3-N-methyl-L-(S)-alanine-pro-panamidyl-3-N-methyl-N-[4-(amino-citrulline-valine-hexanamide-6-maleimidyl)benzyl]carbamate (7)

The product of the preceding step (6, 0.014 g, 0.019 mmol) and MA-VC-PAB-PNP (0.020 g, 0.027 mmol; Concortis Biosystems) were dissolved in 4:1 acetonitrile/water (2.5 mL), treated with 0.1M aqueous NaHCO3 (0.5 mL), and stirred at ambient temperature for 18 h. The reaction was purified directly by reverse-phase chromatography on C18 silica (using 0.1% TFA in acetonitrile/water gradients). Lyophilization of the final column fractions gave the title compound as a white solid (0.002 g, 8%). MS (ESI, pos.): calc'd for $C_{65}H_{89}ClN_{10}O_{18}$, 1332.6; found 1333.9 (M+H), 1316.5 (M−H2O+H), 1355.9 (M+Na).

Example 3

Step 1: 3-Methyldithio-propionic acid succinate ester (8)

The title compound was prepared as a white solid from 3-mercaptopropionic acid using the methods of Widdison et al. J. Med. Chem., 2006, 49 (14), 4392-4408. $^1$H NMR (300 MHz, CDCl$_3$) δ 3.09 (m, 2H), 3.01 (m, 2H), 2.86 (s, 4H), 2.44 (s, 3H).

Step 2: Maytansin-3-N-methyl-L-(S)-alanine-propanamidyl-3-methyldisulfide (9)

The product of the preceding step (8, 2.96 g, 11.9 mmol) and maytansin-3-N-methyl-L-alanine (2, 1.54 g, 2.37 mmol)

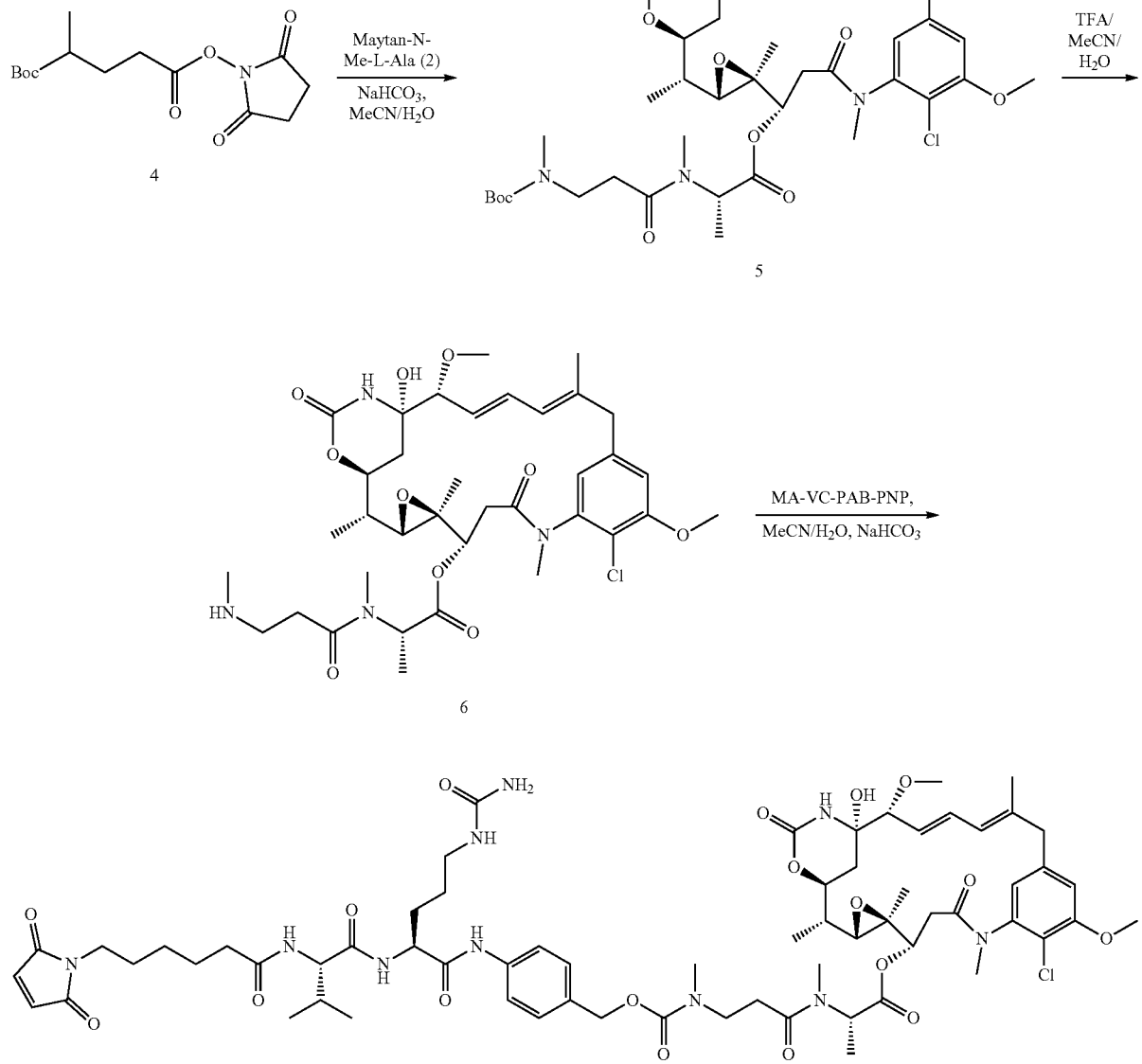

were dissolved in 4:1 acetonitrile/water (25 mL), treated with saturated aqueous $NaHCO_3$ (2 mL), and stirred at ambient temperature for 24 hours. The reaction mixture was treated with brine, extracted thrice with EtOAc, the aqueous layer saturated with NaCl, extracted again with EtOAc, and the combined organic layers dried over $Na_2SO_4$, and filtered. The filtrate was concentrated in vacuo to a gold syrup (ca. 4.5 g) that was purified by flash column chromatography on a 80 g silica gel cartridge (0-100% EtOAc in hexanes over 30 min) giving the title compound as a white solid (1.14 g, 61%). MS (ESI, pos.): calc'd for $C_{36}H_{50}ClN_3O_{10}S_2$, 783.3; found 784.3 (M+H), 766.6 (M−$H_2O$+H).

Step 3: Maytansin-3-N-methyl-L-(S)-alanine-propanamide-3-thiol (10)

The title compound was prepared using a modified version of the method described by Whitesides et al. (J. Org. Chem., 1991, 56, 2648-2650). The product of the preceding step (9, 2.42 g, 3.09 mmol) was dissolved in acetonitrile (30 mL), treated with a solution of tris(2-carboxyethyl)phosphine hydrochloride (8.23 g, 28.7 mmol) in water (30 mL), the pH raised to 3 with the addition of saturated aqueous $NaHCO_3$ (5 mL), the flask purged with Ar, and the reaction stirred at ambient temperature under a rubber septum (vented due to effervescence). After 2 hours, the reaction was treated with brine (ca. 100 mL), bubbled with Ar for 5 min (to remove the free methylmercaptan), and the phases separated. The aqueous phase was extracted twice with EtOAc, saturated with NaCl, and extracted twice more with EtOAc. The combined organic layers were then dried over $Na_2SO_4$, filtered, and the filtrate concentrated and dried in vacuo to give the title compound as a white solid (2.24 g, 98%). MS (ESI, pos.): calc'd for $C_{35}H_{48}ClN_3O_{10}S$, 737.3; found 738.3 (M+H), 720.3 (M−$H_2O$+H).

Step 4: 4-Amino-(N-benzyloxycarbonyl)benzylamine (14)

4-Aminobenzylamine (1.00 g, 8.18 mmol) and triethylamine (1.20 mL, 8.61 mmol) were dissolved in anhydrous tetrahydrofuran (THF, 10 mL) under $N_2$, cooled in a brine/ice bath with stirring, and treated dropwise over 20 min with a solution of benzyl chloroformate (1.20 mL, 8.41 mmol) in anhydrous THF (10 mL). After the addition was complete, the ice bath was removed and the reaction was stirred at ambient temperature for 20 hours, then filtered over a sintered glass funnel to remove insolubles. The solids were washed with EtOAc, the filtrate evaporated in vacuo, and the residue purified by flash column chromatography on a 40 g silica gel column (0-100% EtOAc in hexanes, over 20 min, 40 mL/min). Evaporation of the pure mid-running fractions in vacuo gave the title compound as a light yellow solid (1.47 g, 70%). MS (ESI, pos.): calc'd for $C_{15}H_{16}N_2O_2$, 256.1; found 256.9 (M+H), 278.9 (M+Na).

Step 5: 6-Maleimidylhexanoic acid succinate ester (20)

The title compound was prepared as a colorless gum from commercial 6-aminocaproic acid by a method similar to that of Marnett et al. (J. Med. Chem., 1996, 39, 1692-1703). $^1$H NMR (300 MHz, $CDCl_3$) δ 6.72 (s, 2H), 3.56 (t, 2H, J=7 Hz), 2.86 (s, 4H), 2.64 (t, 2H, J=7 Hz), 1.81 (pentet, 2H, J=8 Hz), 1.66 (m, 2H), 1.45 (m, 2H).

Step 6: Boc-valine-succinate (11)

The title compound was prepared as a white solid from Boc-Val-OH by a method well known in the art (cf.—Widdison et al., J. Med. Chem., 2006, 49 (14), 4401). $^1$H NMR (300 MHz, $CDCl_3$) δ 5.03 (d, 1H, J=10 Hz), 4.60 (dd, 1H, J=9 Hz, 5 Hz), 2.85 (s, 4H), 2.32 (m, 1H), 1.47 (s, 9H), 1.05 (m, 6H).

Step 7: Boc-valine-citrulline (12)

The product of the preceding step (11, 4.23 g, 13.5 mmol) was dissolved in acetonitrile (70 mL), treated with a solution of L-citrulline (3.20 g, 18.3 mmol) in water (30 mL) and a saturated solution of $NaHCO_3$ (18 mL), flask purged with $N_2$, and reaction stirred at ambient temperature for 24 hours. The mixture was concentrated in vacuo to remove the acetonitrile, washed once with EtOAc to remove nonpolar impurities, and the aqueous layer saturated with NaCl and acidified to pH 3 with 10% HCl. The resulting cloudy mixture was extracted four times with 10% isopropanol in EtOAc, the combined organic layers dried over $Na_2SO_4$, and filtered. Concentration and drying of the filtrate in vacuo gave the title compound as a white solid (4.53 g, 90%). MS (ESI, neg.): calc'd for $C_{16}H_{30}N_4O_6$, 374.2; found 373.0 (M−H).

Step 8: Boc-valine-citrulline-amino-4-benzylamino-N-benzyloxycarbamate (15)

The product of the preceding step (12, 3.08 g, 8.23 mmol) was dissolved in N,N-dimethylformamide (DMF, 30 mL, dried over molecular sieves), treated with dicyclohexylcarbodiimide (DCC, 2.31 g, 11.2 mmol) and 1-hydroxybenzotriazole hydrate (HOBt, 1.51 g, 11.2 mmol), the flask purged with $N_2$ and stirred at ambient temperature for 1 hour. A solution of 4-amino-(N-benzyloxycarbonyl)benzylamine (14, 2.30 g, 8.97 mmol) in DMF (15 mL) was then added, the reaction stirred another 3 days, filtered over a sintered glass funnel, and solids washed with ethyl acetate. The filtrate was washed with 1:1 water/saturated $NaHCO_3$ (100 mL), the aqueous layer extracted thrice with 10% isopropanol/EtOAc, and the combined organic layers washed with brine, dried over $Na_2SO_4$, and filtered. During filtration an insoluble gel formed that was dissolved with methanol/EtOAc. Concentration of the filtrate in vacuo gave a gummy gold gel that was treated with diethyl ether (50 mL), sonication, filtered, and suction-dried to a pale yellow solid. This was purified by flash column chromatography on a 330 g silica gel column (0-10% methanol in dichloromethane, 100 mL/min) giving the title compound as a pale yellow solid (4.07 g, 81%). MS (ESI, pos.): calc'd for $C_{31}H_{44}N_6O_7$, 612.3; found 613.4 (M+H)

Step 9: Boc-valine-citrulline-amino-4-benzylamine (16)

The product of the preceding step (15, 3.04 g, 4.96 mmol) and 10% palladium (0) on activated charcoal (0.286 g, 0.269 mmol) were treated under $N_2$ stream with methanol (50 mL) and glacial acetic acid (0.57 mL, 9.95 mmol), the reaction bubbled a few minutes each with $N_2$ then hydrogen, and stirred vigorously under a hydrogen balloon at ambient temperature and pressure for 1 hour. When the reaction was complete by TLC, the balloon was removed, the suspension bubbled several minutes with $N_2$, and filtered over Celite 521. The Celite was washed with methanol, the filtrate evaporated to dryness in vacuo, and the residue triturated once with diethyl ether and dried under high vacuum giving the title compound as a white solid (2.95 g, 99%). MS (ESI, pos.): calc'd for $C_{23}H_{38}N_6O_5$, 478.3; found 479.2 (M+H).

Step 10:
Boc-valine-citrulline-amino-4-benzylisothiocyanate (17)

The product of the preceding step (16, 0.586 g, 0.979 mmol) was dissolved in dry tetrahydrofuran (20 mL) and dry N,N-dimethylformamide (5 mL) under $N_2$, treated with triethylamine (0.40 mL, 2.87 mmol), cooled in an ice bath, and treated dropwise with carbon disulfide (0.10 mL, 1.66 mmol) over 5 min. The reaction was warmed to ambient temperature and stirred for 2 hours, cooled again in ice, and treated with p-toluenesulfonyl chloride (0.281 g, 1.47 mmol). After warming to ambient temperature and stirring for 18 hours, the reaction was washed with 1:1 water/brine, extracted twice with ethyl acetate, the aqueous layer saturated with NaCl, extracted twice more with EtOAc, and the combined organic layers washed with brine, dried over $Na_2SO_4$, and filtered. The evaporated filtrate was purified by flash column chromatography on a 20 g silica gel column (0-100% acetonitrile in EtOAc, 35 mL/min) giving the title compound as a gold solid (0.391 g, 77%) after azeotroping with dichloromethane and drying under high vacuum. MS (ESI, pos.): calc'd for $C_{24}H_{36}N_6O_5S$, 520.3; found 521.1 (M+H).

Step 11: Maytansin-3-N-methyl-L-(S)-alanine-propanamidyl-3-N-[4-(amino-citrulline-Boc-valine)-benzyl]-dithiocarbamate (18)

The product of the preceding step (17, 0.068 g, 0.131 mmol) and maytansin-3-N-methyl-L-(S)-alanine-propanamide-3-thiol (10, 0.048 g, 0.065 mmol) were dissolved in dry THF (3 mL) under Ar, treated with triethylamine (0.050 mL, 0.359 mmol) via syringe, and stirred at ambient temperature under rubber septum for 18 hours. The reaction was concentrated in vacuo, dissolved in 10% isopropanol/ethyl acetate, and washed with 0.5N aq. HCl. The aqueous layer was extracted thrice with 10% IPA/EtOAc, combined organic layers washed with brine, dried over $Na_2SO_4$, and filtered. The evaporated filtrate was purified by flash column chromatography on a 12 g silica gel column (0-20% methanol in EtOAc, 30 mL/min) giving the title compound as a white solid (0.042 g, 51%). MS (ESI, pos.): calc'd for $C_{59}H_{84}ClN_9O_{15}S_2$, 1257.5; found 1258.8 (M+H), 1241.5 (M−H2O+H), 1280.6 (M+Na).

Step 12: Maytansin-3-N-methyl-L-(S)-alanine-propanamidyl-3-N-[4-(amino-citrulline-valine)-benzyl]-dithiocarbamate (19)

The title compound was prepared as a gold solid (0.016 g, 100%) from the product of the preceding step (18, 0.014 g, 0.011 mmol) by the method of Example 2, Step 3 (compound 6). The compound was used without further purification. MS (ESI, pos.): calc'd for $C_{54}H_{76}ClN_9O_{13}S_2$, 1157.5; found 1159.4 (M+H).

Step 13: Maytansin-3-N-methyl-L-(S)-alanine-propanamidyl-3-N-[4-(amino-citrulline-valine-hexanamide-6-maleimidyl)benzyl]-dithiocarbamate (21)

The product of the preceding step (19, 0.055 g, 0.032 mmol) was dissolved in 1:1 acetonitrile/water (4 mL), treated with 1N aq. NaHCO3 (0.5 mL) and a solution of 6-maleimidylhexanoic acid succinate ester (20, 0.070 g, 2.27 mmol) in acetonitrile (6 mL), and the flask purged with Ar under rubber septum. After the reaction stirred at ambient temperature for 5 hours, it was stored at −20° C. for 3 days before warming again to ambient temperature and diluting with brine. The mixture was extracted thrice with ethyl acetate, combined organic layers dried over $Na_2SO_4$, and filtered. The evaporated filtrate was purified by flash column chromatography on a 12 g silica gel column (0-20% methanol in EtOAc over 18 min, 25 mL/min) giving the title compound as a pale yellow solid (0.011 g, 26%). MS (ESI, pos.): calc'd for $C_{64}H_{87}ClN_{10}O_{16}S_2$, 1350.5; found 1352.0 (M+H), 1334.5 (M−H$_2$O+H), 1373.5 (M+Na).

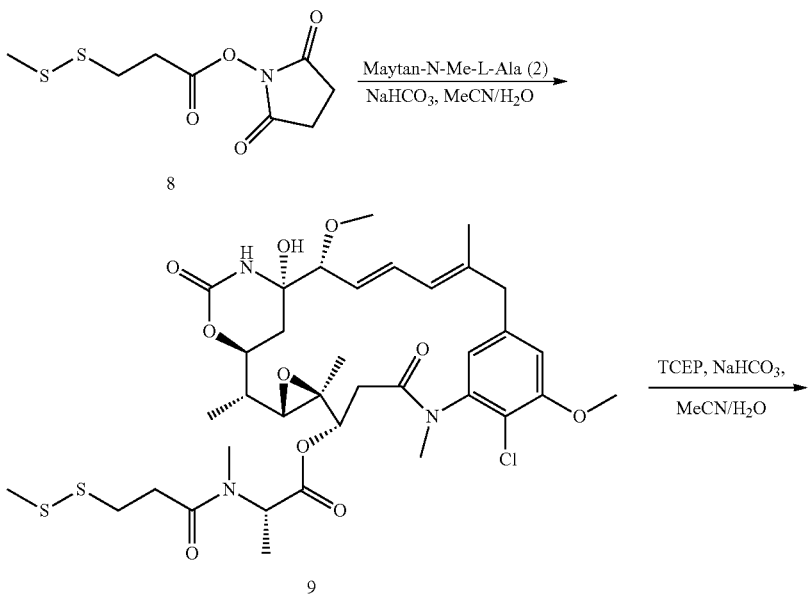

-continued
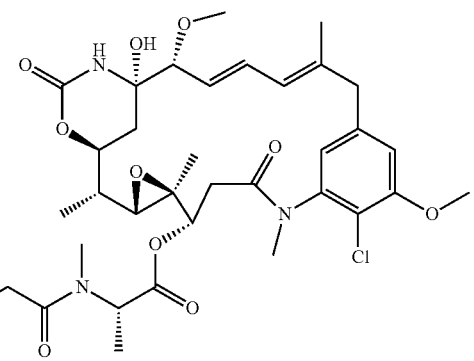
10
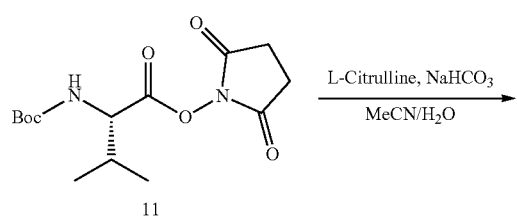
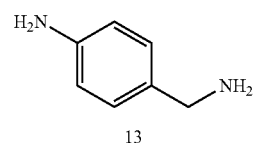
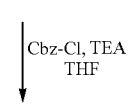
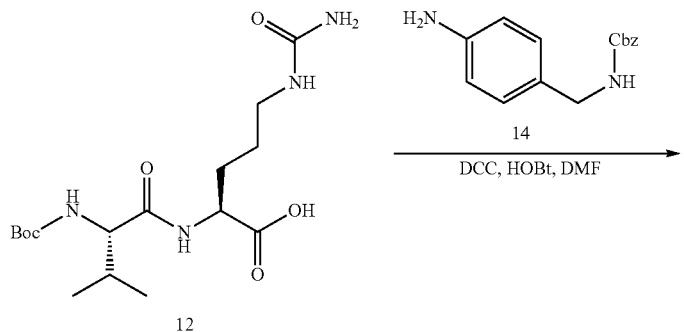
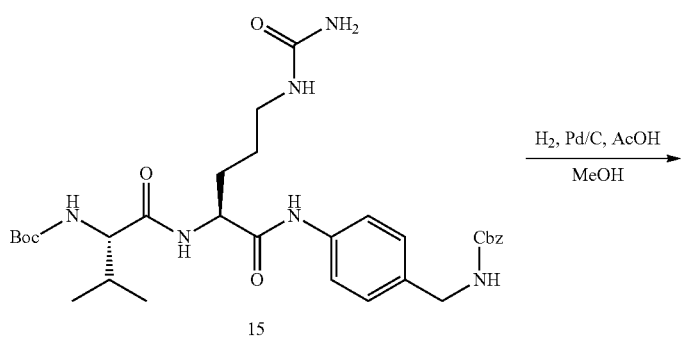

-continued
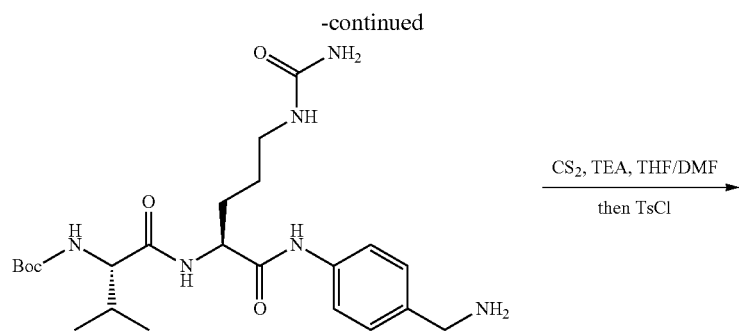
16
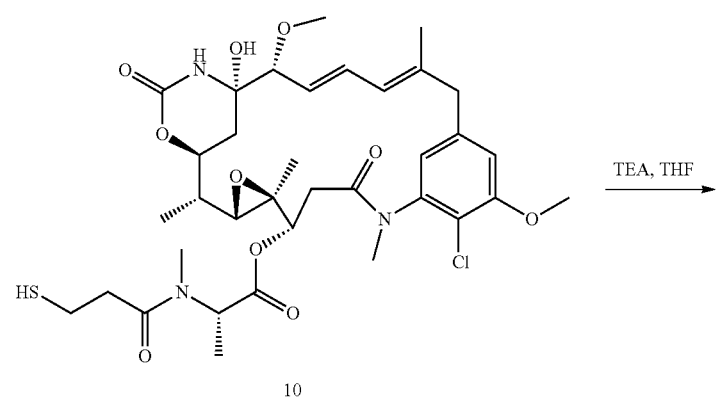
17
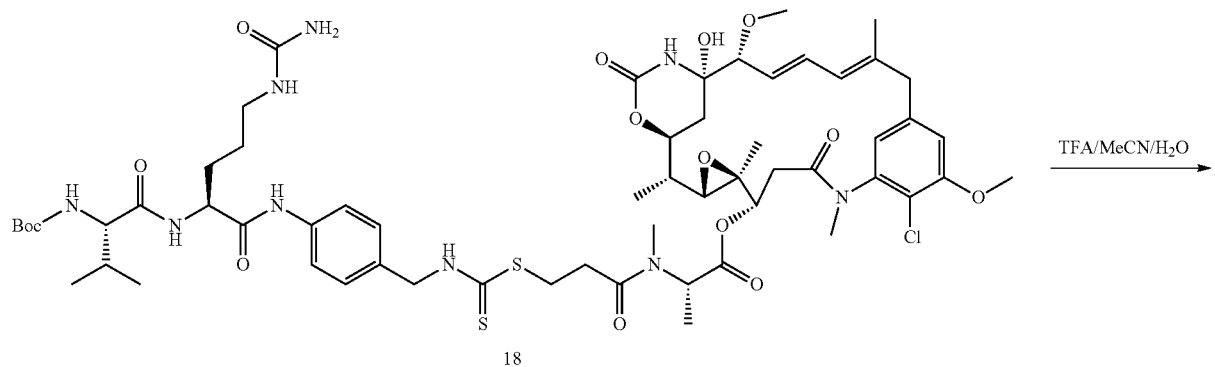
18

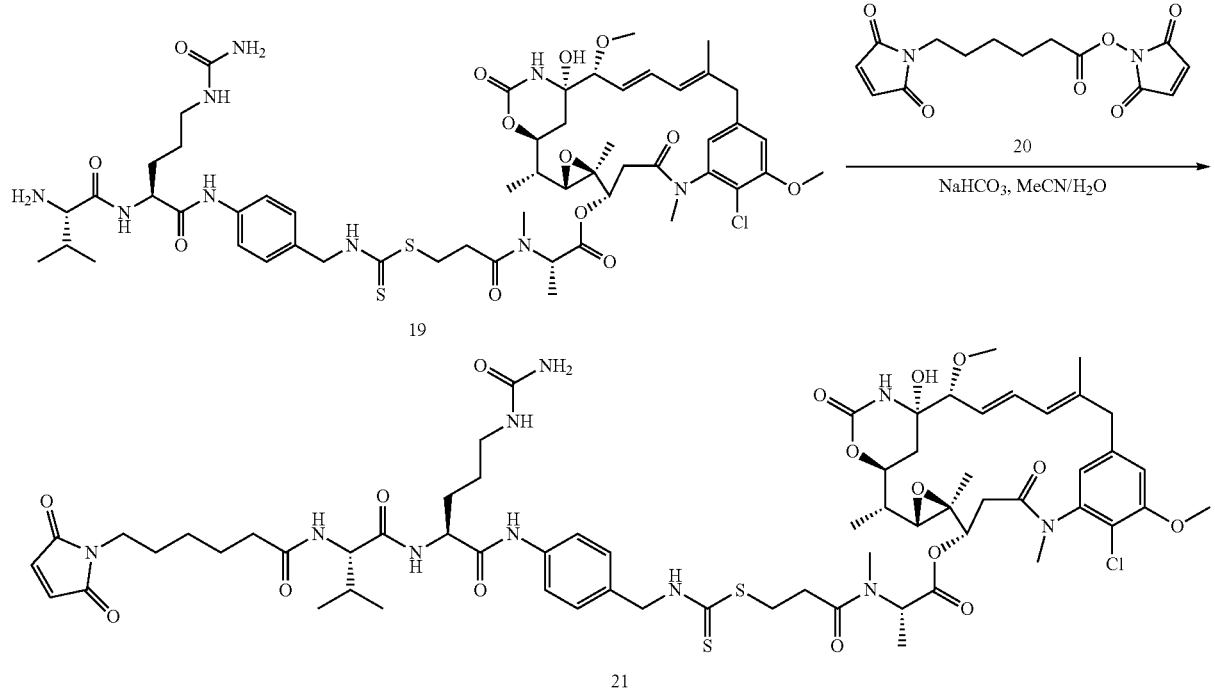

Example 4

Step 1: N-(4-Aminomethyl-phenyl)-acetamide hydrochloride (23)

The title compound was prepared as a light yellow solid from 4-aminobenzylamine by the method of King et al. (J. Am. Chem. Soc., 1992, 114(8), 3033). $^1$H NMR (300 MHz, DMSO-$d_6$): δ 10.18 (s, 1H), 8.36 (br s, 3H), 7.63 (d, 2H, J=8.7 Hz), 7.41 (d, 2H, J=8.7 Hz), 3.95 (s, 2H), 2.06 (s, 3H).

Step 2: N-(4-Isothiocyanatomethyl-phenyl)-acetamide (24)

The product of the preceding step (23, 0.277 g, 1.38 mmol) was dissolved in THF (4.5 mL) and DMF (2.0 mL), cooled in ice under N2, treated with triethylamine (0.66 mL, 4.73 mmol), then treated dropwise with carbon disulfide (0.125 mL, 2.07 mmol). The reaction was warmed to ambient temperature, stirred for 3 hours, then cooled again in ice. After treating with p-toluenesulfonyl chloride (0.274 g, 1.45 mmol), the reaction slowly warmed to ambient temperature while stirring for 18 hours. The mixture was diluted with water, acidified to pH 2 with 10% aq. HCl, and extracted thrice with EtOAc. The combined organic layers were washed with brine, dried over Na$_2$SO$_4$, and filtered. The evaporated filtrate was purified by flash column chromatography on a 20 g silica gel column (0-50% acetonitrile in EtOAc over 20 min, 30 mL/min) giving the title compound as a cream-colored solid (0.157 g, 55%). $^1$H NMR (300 MHz, CDCl$_3$) δ 7.55 (d, 2H, J=8.7 Hz), 7.29 (m, 3H), 4.70 (s, 2H), 2.23 (s, 3H).

Step 3: Maytansin-3-N-methyl-L-(S)-alanine-propanamidyl-3-N-[4-(acetamidyl)benzyl]-dithio-carbamate (25)

The product of the preceding step (24, 0.093 g, 0.45 mmol) and the product of Example 3, Step 3 (10, 0.070 g, 0.095 mmol) were dissolved in acetonitrile (MeCN, 2 mL) and dry DMF (1 mL), and treated with basic alumina (activated, Brockmann I, 0.357 g). After purging the flask with argon, the reaction was stirred at ambient temperature for 2 days, filtered, and the solids washed with methanol/acetonitrile. The evaporated filtrate was purified by flash column chromatography on a 12 g silica gel column (0-50% acetonitrile in EtOAc over 15 min, 25 mL/min) and the slower product fractions concentrated in vacuo to an impure pale yellow gum. This was purified by RP-HPLC (Phenomenex Gemini C18, 30×150 mm column, 30-90% acetonitrile in water, 0.1% TFA in both) and the pure fractions were lyophilized giving the title compound as a white solid (0.016 g, 18%). MS (ESI, pos.): calc'd for C$_{45}$H$_{58}$ClN$_5$O$_{11}$S$_2$, 943.3; found 944.7 (M+H), 927.1 (M-H2O+H), 966.6 (M+Na).

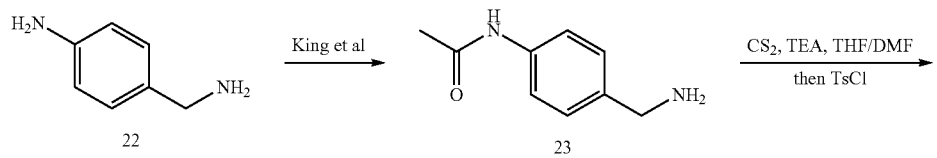

-continued
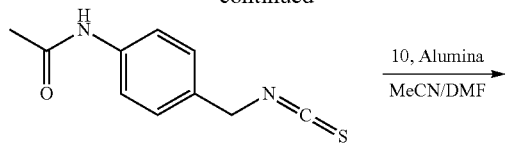
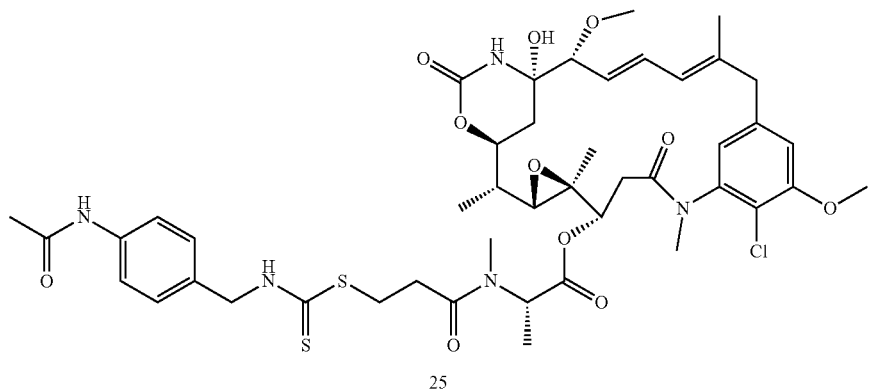
Example 5
Maytansin-3-N-methyl-L-(S)-alanine-β-alanine (27)
The title compound was prepared as a pale yellow solid from 2,5-dioxopyrrolidin-1-yl 3-((tert-butoxycarbonyl)amino)propanoate (26) by the method of Example 2, Steps 1-3. MS (ESI, pos.): calc'd for C35H49ClN4O10, 720.3; found 721.4 (M+H).
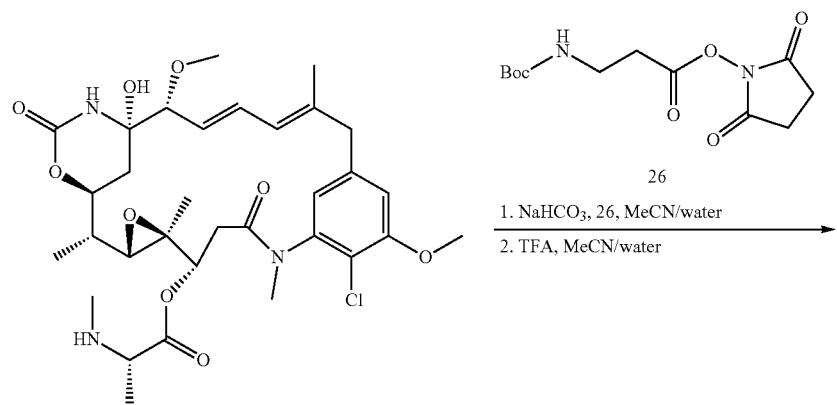

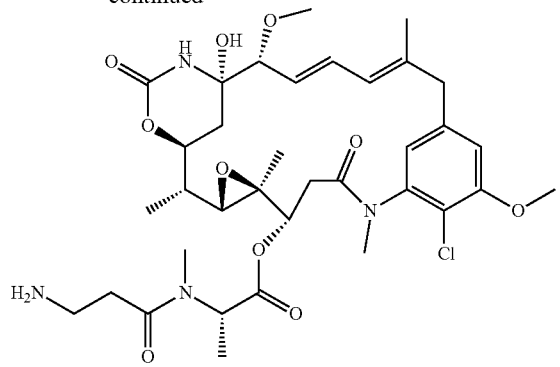

27

Example 6

Maytansin-3-N-methyl-L-(S)-alanine-γ-aminobutyramide (29)

The title compound was prepared as a pale yellow solid from N-Boc-GABA-OH (28) by the method of Example 2, Steps 1-3. MS (ESI, pos.): calc'd for $C_{36}H_{51}ClN_4O_{10}$, 734.3; found 735.5 (M+H).

Example 7

Maytansin-3-N-methyl-L-(S)-alanine-N-Me-γ-aminobutyramide (31)

The title compound was prepared as a pale yellow solid from N-Boc-N-Me GABA-OH (30) by the method of Example 2, Steps 1-3. MS (ESI, pos.): calc'd for C37H53ClN4O10, 748.4; found 749.5 (M+H).

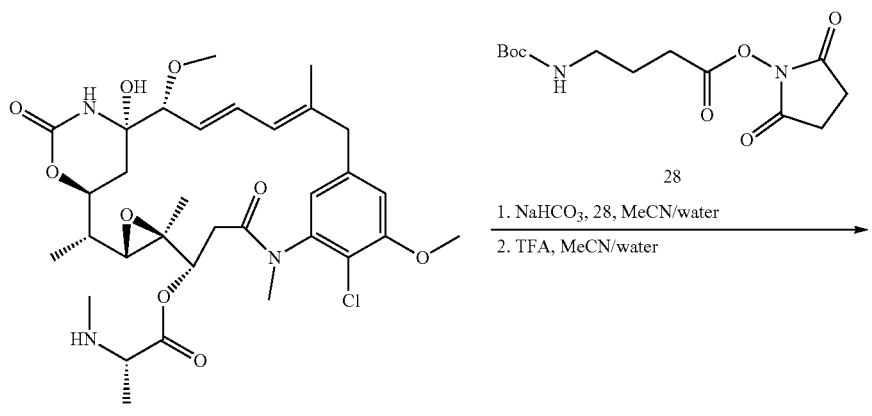

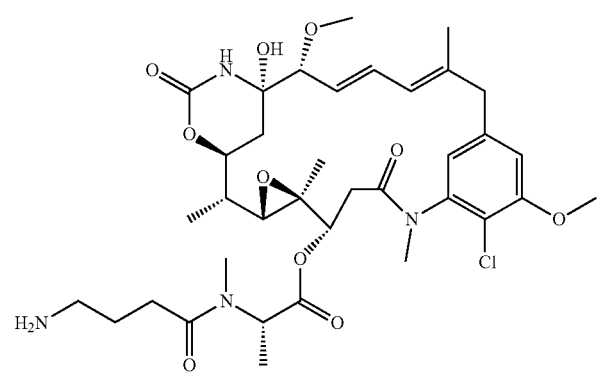

29

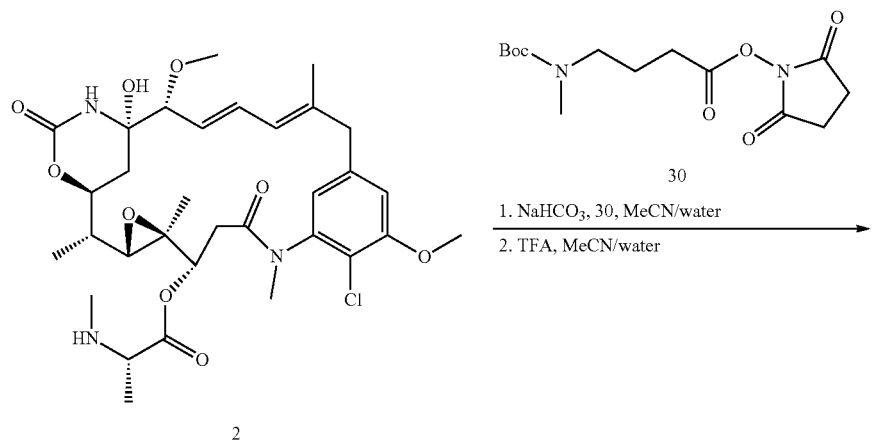

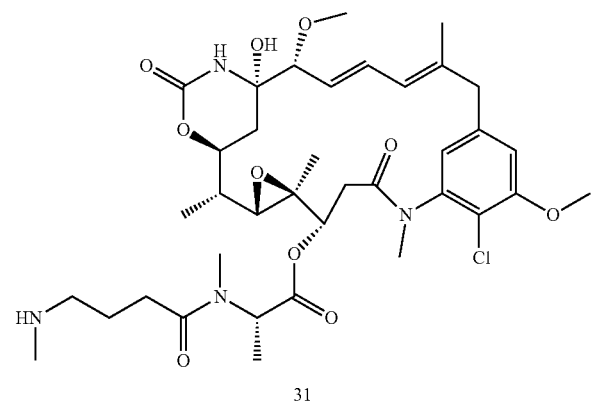

Example 8

Step 1: Maytansin-3-N-methyl-L-(S)-alanine-N-carboxy-6-[3,4-dihydro-2-(tert-butoxycarbonyl)-1H-isoquinoline]

Maytan-3-N-methyl-L-(S)-alanine (2, 0.034 g, 0.052 mmol), commercial N-Boc-1,2,3,4-tetrahydroisoquinoline-6-carboxylic acid (32, 0.019 g, 0.069 mmol), and 1-(3-Dimethylaminopropyl)-3-ethylcarbodiimide hydrochloride (EDC, 0.024 g, 0.125 mmol) were weighed into a round-bottom flask with stir bar, dissolved in dichloromethane (3 mL), the flask purged with Ar and sealed with a rubber septum, and the reaction stirred at ambient temperature. After 2 days, the reaction was diluted with EtOAc and washed with dilute aq. NaHCO3, and the aqueous layer was extracted twice with EtOAc. The combined organic layers were washed with brine, dried over $Na_2SO_4$, and filtered. The evaporated filtrate was then purified on a 12 g RediSep Gold silica gel column via ISCO system (EtOAc—5:5:1 EtOAc/DCM/MeOH over 12 mins, 30 mL/min), and the combined TLC-pure fractions evaporated and dried in vacuo giving the title compound as a pale solid (0.026 g, 55%). MS (ESI, pos.): calc'd for $C_{47}H_{61}ClN_4O_{12}$, 908.4; found 909.2 (M+H), 891.2 (M–H2O+H).

Step 2: Maytansin-3-N-methyl-L-(S)-alanine-N-carboxy-6-(1,2,3,4-tetrahydroisoquinoline) (33)

The title compound was prepared as a white solid (0.013 g, 52%) from the product of the preceding step (0.025 g, 0.027 mmol) by the method of Example 2, Step 3 (compound 6). MS (ESI, pos.): calc'd for $C_{42}H_{53}ClN_4O_{10}$, 808.3; found 809.2 (M+H).

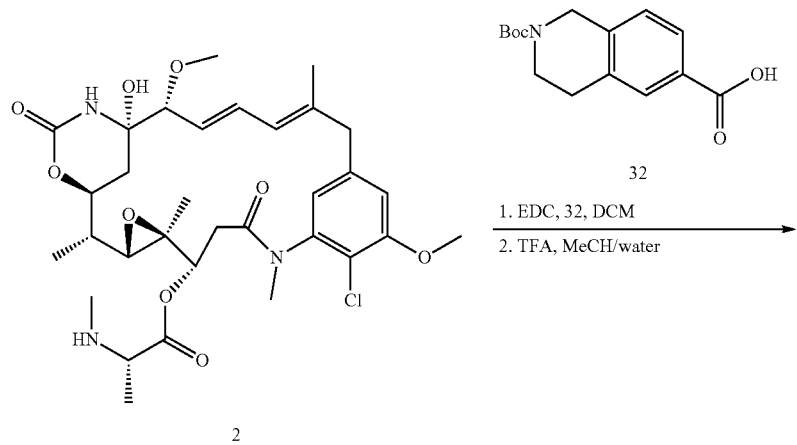

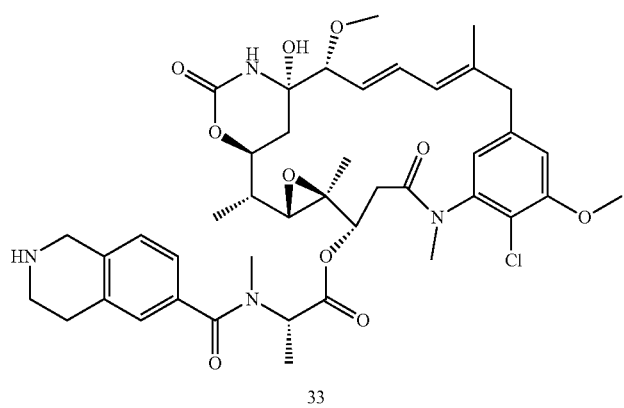

Example 9

Step 1: Maytansin-3-N-methyl-L-(S)-alanine-N-carboxy-4-[1-(tert-butoxycarbonyl)-piperidine]

The title compound was prepared as a white solid (0.027 g, 46%) from maytan-3-N-methyl-L-(S)-alanine (2, 0.045 g, 0.069 mmol) and commercial 1-t-butoxycarbonylpiperidine-4-carboxylic acid (34, 0.024 g, 0.105 mmol) by the method of Example 8, Step 1. MS (ESI, pos.): calc'd for $C_{43}H_{61}ClN_4O_{12}$, 860.4; found 861.2 (M+H), 843.2 (M–H$_2$O+H).

Step 2: Maytansin-3-N-methyl-L-(S)-alanine-N-carboxy-4-piperidine (35)

The title compound was prepared as a white solid (0.012 g, 50%) from the product of the preceding step (0.025 g, 0.029 mmol) by the method of Example 2, Step 3 (compound 6). The compound purified on a C18 column using a different gradient and modifier (20-80% MeCN in water, 0.05% acetic acid in both). Lyophilization of the pure fractions gave the title compound (0.008 g, 35%). MS (ESI, pos.): calc'd for $C_{38}H_{53}ClN_4O_{10}$, 760.3; found 761.2 (M+H).

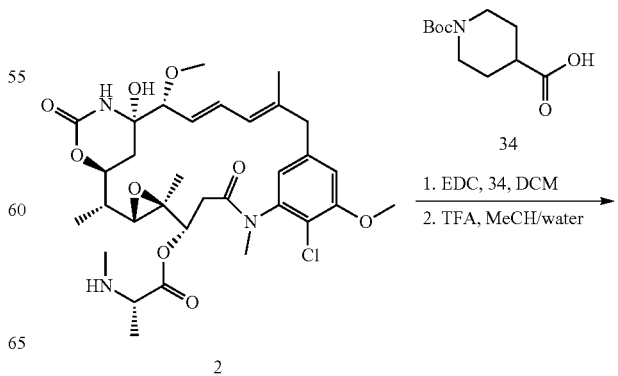

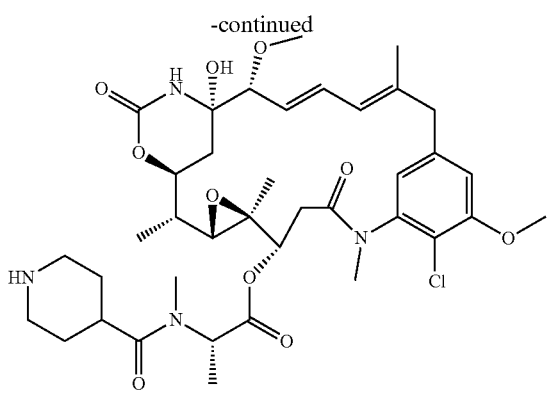

35

Example 10

Step 1: Maytansin-3-N-methyl-L-(S)-alanine-N-methyl-beta-alanine-N-[4-(tert-butoxycarbonyl-valine-citrulline-amino)benzyloxy]-carbamate The Boc-valine-citrulline-p-aminobenzyloxy-(p-nitrophenyloxy)-carbonate (36), prepared according to WO 2005112919, (0.092 g, 0.143 mmol), the product of Example 2, Step 3 (6, 0.110 g, 0.130 mmol), and 1-Hydroxy-7-azabenzotriazole (HOAT, 0.037 g, 0.272 mmol) were dissolved in DMF (7 mL), treated with triethylamine (0.100 mL, 0.717 mmol), and stirred at ambient temperature in a stoppered flask. After 18 hours, the reaction mixture was concentrated to an oil in vacuo, dissolved in dichloromethane, and purified on a 24 g RediSep Gold column via ISCO Combiflash (0-20% methanol in ethyl acetate). Evaporation of the product fractions in vacuo then gave the title compound as a pale yellow solid (0.129 g, 80%). MS (ESI, pos.): calc'd for $C_{60}H_{86}ClN_9O_{17}$, 1239.6; found 1240.8 (M+H).

Step 2: Maytansin-3-N-methyl-L-(S)-alanine-N-methyl-beta-alanine-N-[4-(valine-citrulline-amino)benzyloxy]-carbamate (37)

The title compound was prepared as a white solid (0.074 g, 63%) from the product of the preceding step (0.128 g, 0.103 mmol) by the method of Example 2, Step 3 (compound 6). MS (ESI, pos.): calc'd for $C_{55}H_{78}ClN_9O_{15}$, 1139.5; found 1141.4 (M+H).

Step 3: Maytansin-3-N-methyl-L-(S)-alanine-N-methyl-beta-alanine-N-[4-(4-{isothiocyanato-phenyl}-thioureido-valine-citrulline-amino)benzyloxy]-carbamate (39)

The product of the preceding step (37, 0.037 g, 0.029 mmol) was dissolved in tetrahydrofuran (THF, 5 mL) in a vial, treated with triethylamine (0.020 mL, 0.143 mmol), and the resulting solution added dropwise to a flask containing a stirred solution of 1,4-phenylenediisothiocyanate (38, 0.055 g, 0.286 mmol) in THF (10 mL) over 15 min. The vial was rinsed with THF (2 mL) and the solution added to the reaction flask, which was sealed with a rubber septum. After stirring at ambient temperature for 24 hours, the reaction was concentrated in vacuo to dryness, the crude product dissolve in acetonitrile, and filtered over a 0.45 um PTFE membrane. The filtrate was then purified on a 30 g C18 RediSep Gold column via ISCO (20-80% MeCN in water, 0.05% HOAc in both solvents) and the purest fractions (by LC) combined, frozen at −78° C., and lyophilized giving the title compound as white solid (0.023 g, 59%). MS (ESI, pos.): calc'd for $C_{63}H_{82}ClN_{11}O_{15}S_2$, 1331.5; found 1332.0 (M+H).

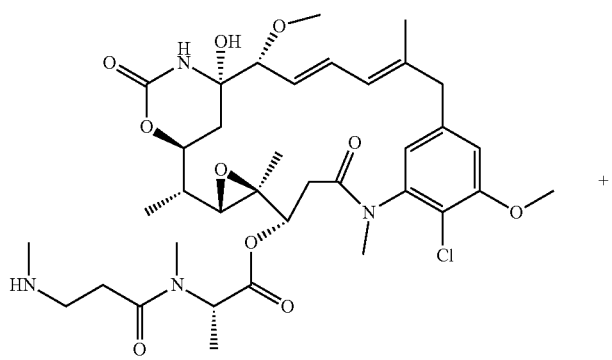

6

+

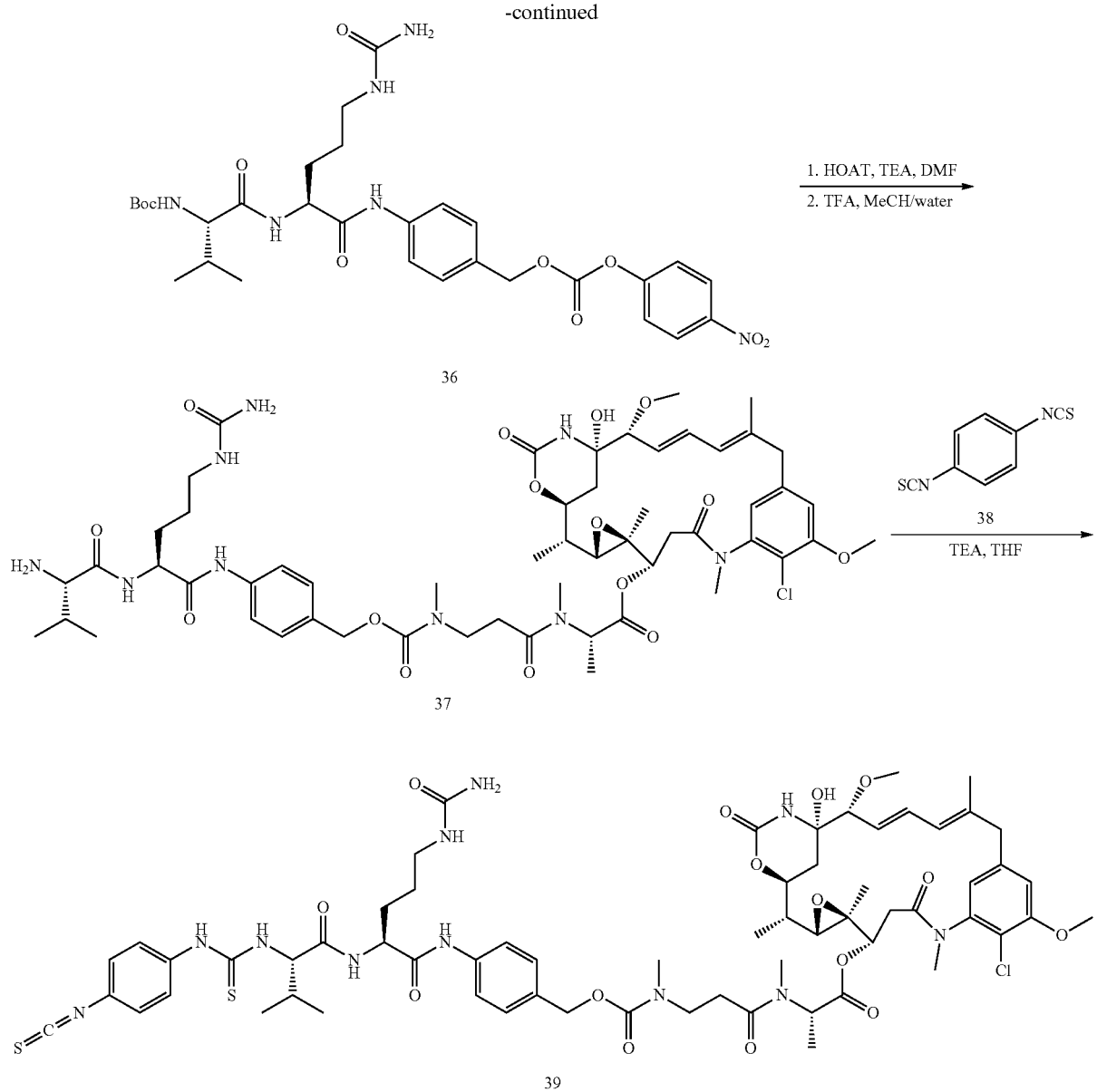

Example 11

Step 1: 1-(4-Amino-butyl)-maleimide

A solution of commercial Boc-1-aminobutyl-4-maleimide (0.304 g, 1.13 mmol) in dichloromethane (10 mL) was treated with trifluoroacetic acid (1.00 mL, 13.1 mmol), the flask purged with Ar, sealed with a rubber septum and bubbler vent, and stirred at ambient temperature. The reaction was complete by TLC after 18 hours, so it was concentrated in vacuo, triturated twice with diethyl ether, and dried in vacuo to a gum. This was triturated twice more with ether (while scraping with a spatula), decanted, and dried again in vacuo giving the title compound as a white solid (0.321 g, 100%). MS (ESI, pos.): calc'd for $C_8H_{12}N_2O_2$, 168.1; found 169.0 (M+H).

Step 2: 1-(4-Isothiocyanato-butyl)-maleimide (41)

The product of the preceding step was dissolved in acetonitrile (MeCN, 3×40 mL) and concentrated in vacuo at 60° C. via rotary evaporator. The dried product (0.650 g, 2.45 mmol) was dissolved in MeCN (75 mL) and chloroform (30 mL) in a flask, treated with triethylamine (1.0 mL, 7.35 mmol), and the resulting solution added dropwise to a flask containing 1,1'-thiocarbonyldi-2,2'-pyridone (0.68 g, 2.94 mmol) in chloroform (25 mL) under nitrogen over 10 min. The reaction was stirred at ambient temperature for 18 hours, the reaction was concentrated in vacuo to dryness, the crude product was dissolved in dichloromethane (DCM) and purified on a 120 g silica gel RediSep Gold column via flash column chromatography (0-10% MeOH in DCM). The cleanest fractions (by LC) were combined and concentrated to dryness giving the title compound as white solid (0.26 g, 50%). MS (ESI, pos.): calc'd for $C_9H_{10}N_2O_2S$, 210.0; found 211.2 (M+H).

Step 3: Maytansin-3-N-methyl-L-(S)-alanine-N-methyl-beta-alanine-N-[4-(4-{maleimidylbutyl}-thioureido-valine-citrulline-amino)benzyloxy]-carbamate (42)

The product of Example 10, Step 2 (37, 0.029 g, 0.023 mmol) was dissolved in dry DMF (2 mL), treated with diisopropylethylamine (0.020 mL, 0.115 mmol) via dry syringe, then with a solution of product of the preceding step (41, 0.026 g, 0.124 mmol) in dry DMF (2 mL). The reaction flask was purged with Ar, sealed with a rubber septum, and the reaction stirred at ambient temperature. After 18 hours the reaction appeared to be 80% complete by LCMS, so it was evaporated to an oil in vacuo, dissolved in MeCN/water, and purified on a 30 g C18 RediSep Gold column via flash column chromatography (20-80% MeCN in water, 0.05% HOAc in both solvents). The cleanest fractions by LCMS were combined, briefly rotavapped, frozen on dry ice, and lyophilized overnight giving the title compound as a white solid (0.020 g, 65%). MS (ESI, pos.): calc'd for $C_{64}H_{88}N_{11}O_{17}SCl$, 1349.6; found 1351.1 (M+H), 1372.9 (M+Na), 1333.6 (M–$H_2O$+H).

Conjugation Method for Compounds 3, 7, 21 and 42

The antibody (10 mg/ml) in 50 mM HEPES, 150 mM NaCl, pH 7.5, was treated with 1 mM dithiothreitol at 37° C. for 30 min. After gel filtration (G-25, pH 4.5 sodium acetate), the maleimido linker payload derivative (1.2 equivalents/SH group) in DMSO (10 mg/ml) was added to the reduced antibody and the mixture adjusted to pH 7.0 with 1 M HEPES (pH 7.4). After 1 h the reaction was quenched with excess N-ethyl maleimide. The conjugates were purified by size exclusion chromatography and sterile filtered. Protein and linker payload concentrations were determined by UV spectral analysis. Size-exclusion HPLC established that all conjugates used were >95% monomeric, and RP-HPLC established that there was <0.5% unconjugated linker payload. Yields are reported in Table 1 based on protein. All conjugated antibodies were analyzed by UV for linker payload loading values according to Hamblen et al, Cancer Res., 2004 10 7063. The results are summarized in Table 1.

Conjugation Method for Compound 39

To the antibody (2-5 mg/ml) in 50 mM carbonate, 150 mM NaCl, pH 9.0, was added 15% by volume dimethyl

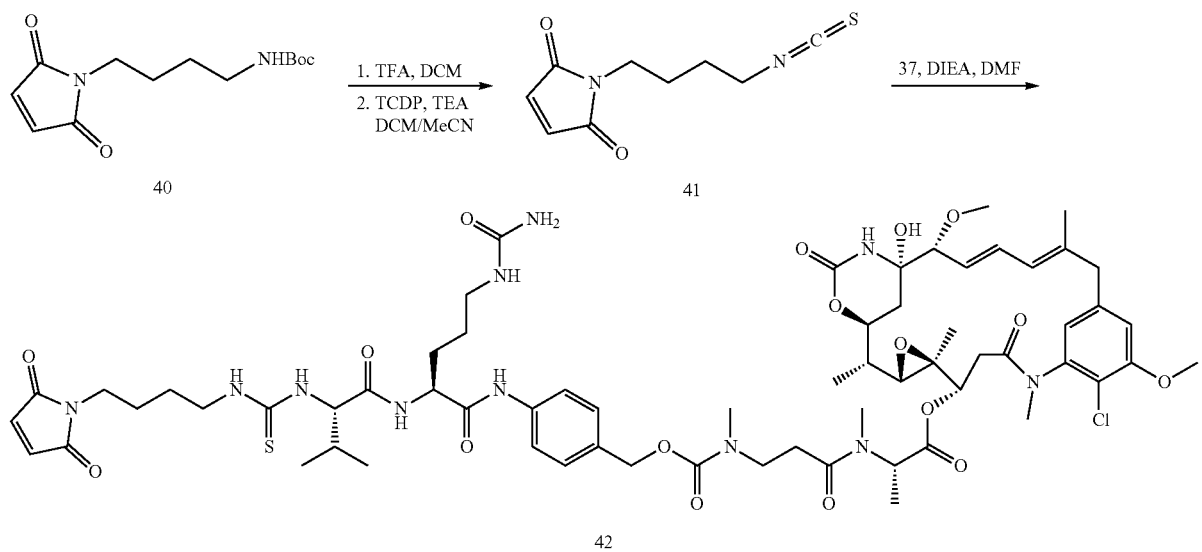

Example 12

Conjugate Preparation and Characterization

For the initial set of experiments, four antibodies were conjugated to various linker-drug compounds of the disclosure using the procedure below. The four antibodies used in these experiments were: (1) a PSMA antibody having the heavy and light chain variable domains of clone AB-PG1-XG1-006 as set forth in WO 2007002222$A_2$, (2) a STEAP1 antibody having the heavy and light chain variable domains of clone mu120, expressed as a hIgG1, as set forth in WO 2008052187$A_2$, (3) an EGFRvIII antibody having the heavy and light chain variable domains of clone 131 as set forth in WO2013075048$A_1$, and (4) a PRLR having the heavy and light chain variable domains of clone H1H6953N as set forth in U.S. Application Ser. No. 61/868,185; filed on Aug. 21, 2013 (the disclosure of which is hereby incorporated by reference in its entirety). All the monoclonal antibodies were expressed in CHO cells and purified by Protein A. A non-binding control derived from an immunological antigen having no relation to oncology was also used.

acetamide. The linker payload derivative 39 (5-10 equivalents) in DMSO (10 mg/ml) was added to the antibody and the mixture incubated at 37° C. for 4-12 hours. The conjugates were purified by size exclusion chromatography and sterile filtered. Protein and linker payload concentrations were determined by UV spectral analysis. Size-exclusion HPLC established that all conjugates used were >95% monomeric, and RP-HPLC established that there was <0.5% unconjugated linker payload. For these conjugates, the payload to antibody ratio was determined by MALDI-TOF (Table 1).

TABLE 1

| Compound | ε252 nm (cm$^{-1}$ M$^{-1}$) | ε280 nm (cm$^{-1}$ M$^{-1}$) |
| --- | --- | --- |
| 3 | 32000 | 8500 |
| 7 | 50600 | 8100 |
| 21 | 44190 | 9460 |
| 39 | | |

TABLE 1-continued

| Antibody | ε252 nm (cm$^{-1}$ M$^{-1}$) | ε280 nm (cm$^{-1}$ M$^{-1}$) |
|---|---|---|
| STEAP1 | 87939 | 244276 |
| PSMA | 77652 | 224320 |
| PRLR | 80673 | 220420 |
| EGFRvIII | 79579 | 209420 |
| Isotype Control | 75113 | 218360 |

| Antibody Conjugate | Payload:Antibody (UV) | Yield % |
|---|---|---|
| STEAP1-7 | 1.4 | 36 |
| PSMA-3 | 3.5 | 44 |
| PSMA-7 | 3.4 | 60 |
| PSMA-21 | 0.9 | 45 |
| PRLR-7 | 3.0 | 70 |
| EGFRvIII-7 | 3.4 | 64 |
| EGFRvIII-39 | 1.3 (MALDI) | 40 |
| Isotype Control-3 | 3.0 | 48 |
| Isotype Control-7 | 2.3 | 51 |
| Isotype Control-21 | 2.3 | 45 |
| Isotype Control-39 | 1.1 (MALDI) | 40 |

Example 13

In Vitro Antibody-Drug Conjugate (ADC) Cell-Free Enzymatic Assays
Cathepsin B Incubation In vitro cell-free enzymatic assay procedure was adopted from Dubowchik, et al., Bioconjugate Chem. 2002 13 855. The DAR corrected PRLR-7 and Isotype Control-7 concentration was set to 7.00 uM in 25 mM sodium acetate buffer, 1 mM EDTA, pH 5.0 and pre-incubated at 37° C. Cathepsin B (Sigma #C8571) was activated at room temperature for 15 minutes with 1 equivalent of 30 mM DTT, 15 mM EDTA to 2 equivalents of cathepsin B stock. The activated cathepsin B solution was added to the ADC solutions at a 1:750 molar ratio. Samples were incubated at 37° C. over a 24 hour period and aliquoted for either HPLC (HISEP)-UV detection or LC-MS detection vide infra.

LC-MS Detection

At designated time points, a small aliquot was removed and combined with 2 equivalents by volume of cold methanol. Supernatant was recovered and analyzed by liquid chromatography-mass spectrometry (LCMS) for cathepsin B linker payload cleavage yielding compound 6 using a Merck Chromolith FastGradient RP-18e, 2×50 mm column, 10 to 90% MeCN over 5 mins, in H$_2$O with 0.05% HOAc in both solvents and a flow rate of 1 mL. The elution profile was monitored at 254 nm. All of the aliquots incubated at 37° C. with cathepsin B contained compound 6 eluting at 5.1 minute with a mass of 735 M+H (calc'd for C36H51ClN4O10, 734.3) and none of the aliquots without cathepsin B contained any 6. This was also confirmed by injection of pure compound 6 from Example 2, step 3.

HPLC (HISEP)-UV Detection

Solutions were injected "as is" at designated time points. The following gradient method was utilized: buffer A 100% 100 mM NH4OAc, pH 7.0 and buffer B 100% acetonitrile, flow rate 0.4 mL/min, from 5 to 70% buffer B, over a Supelco LC-HISEP; 150 mm×4.6 mm, column. The elution profile was monitored at 280 nm and 252 nm. All aliquots of the cathepsin B incubated ADCs contained a species which elutes at 19.4 minute. Pure compound 6 elutes at the identical retention time under the same gradient conditions. The 19.4 minute species was not present in the aliquot without cathepsin B.

The results of this Example are significant in part because cathepsin B proteolysis of 6 should only occur after internalization of the ADC in the cell where the enzyme exists. Off target effects should be reduced since the antibody delivers the cytotoxic payload directly to targeted cells.

Example 14

In Vitro Cytotoxicity Assays

In this Example, the ability of various antibody-drug conjugates to kill antigen-expressing tumor cells in vitro was assessed.

Cells were seeded in PDL-coated 96 well plates at 375 (MMT/hEGFRvIII), 1500 (U251/hEGFRvIII), 2000 (HEK293/hEGFRvIII), or 3000 (C4-2, PC3/hSTEAP1, T47D, and U87-MG) cells per well in complete growth media and grown overnight. For cell viability curves, serially diluted conjugates or free representative payloads were added to the cells at final concentrations ranging from 500 nM to 1 pM and incubated for 3 days. To measure viability in MMT/hEGFRvIII, U251/hEGFRvIII, HEK293/hEGFRvIII, C4-2, PC3/hSTEAP1, and U87-MG, cells were incubated with CCK8 (Dojindo) for the final 1-3 hours and the absorbance at 450 nm (0D450) was determined on a Flexstation3 (Molecular Devices). To measure viability in T47D, cells were incubated on ice for 30 min in 4% formaldehye+3 ug/ml Hoechst. Images of Hoechst stained nuclei were acquired on the ImageXpress Micro XL (Molecular Devices) and nuclear counts were determined with the Columbus analysis software (PerkinElmer). Background OD450 levels (CCK8) or nuclear counts from digitonin (40 nM) treated cells were subtracted from all wells and viability is expressed as a percentage of the untreated controls. IC$_{50}$ values were determined from a four-parameter logistic equation over a 10-point response curve (GraphPad Prism). All curves and IC$_{50}$ values are corrected for payload equivalents.

Figure 1B:
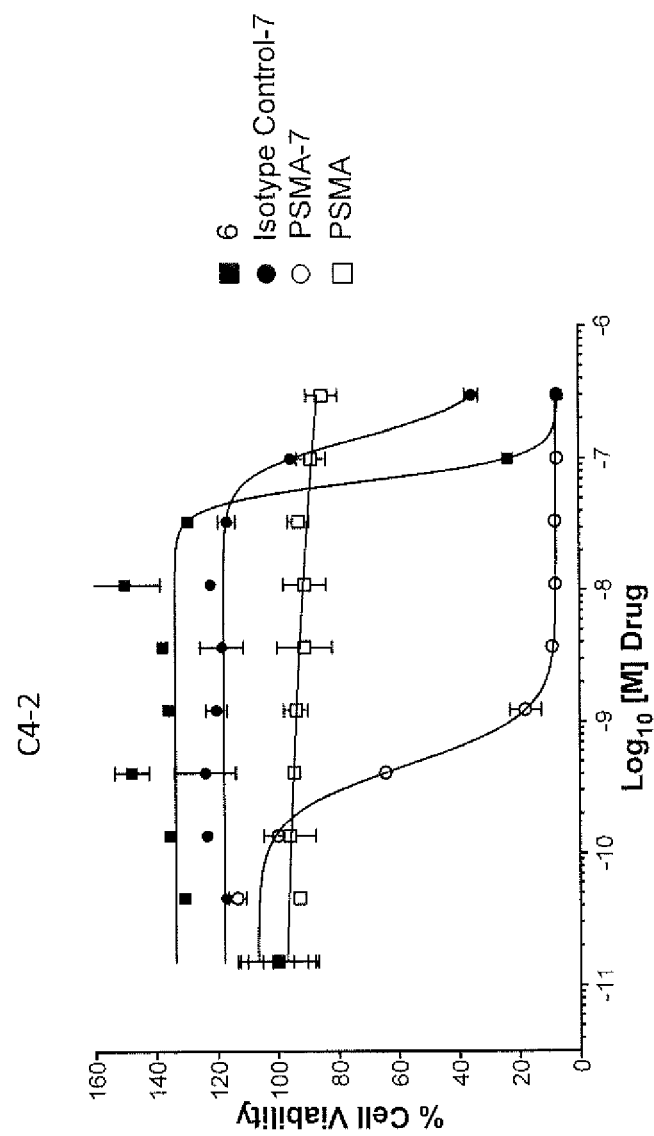
Figure 1C:
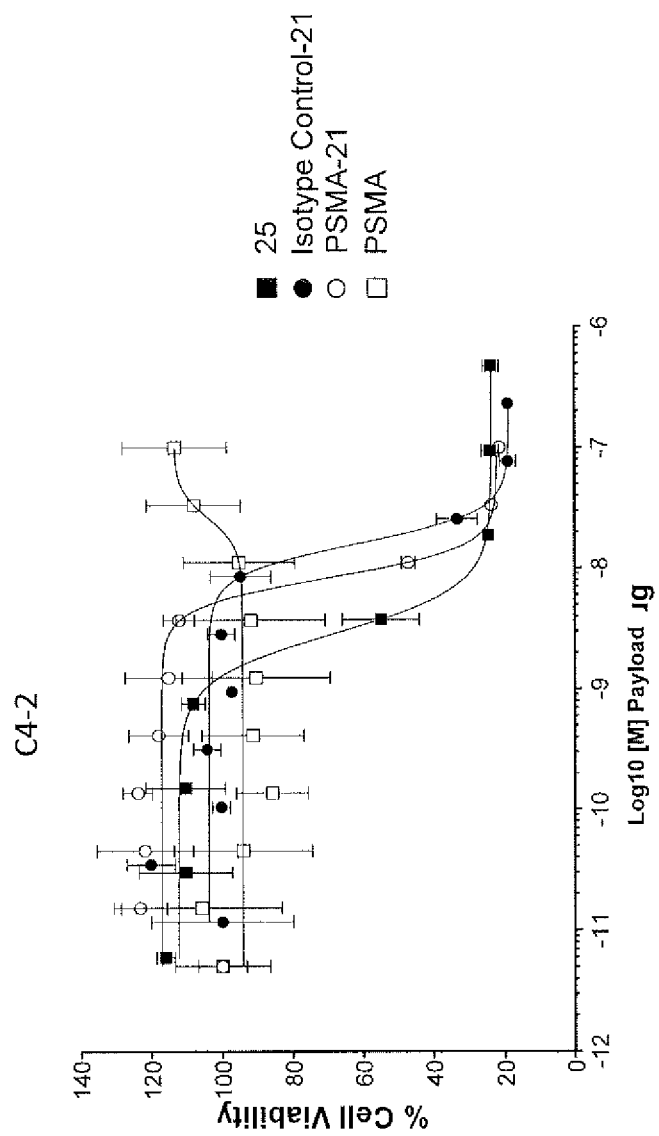

In C4-2 cells (prostate cancer line), natively expressing PSMA at 271 fold above isotype control binding, the maytansinoid conjugates PSMA-3, PSMA-7, and PSMA-21 possess IC$_{50}$ values of 3.8, 0.5, and 8.3 nM, respectively (FIG. 1). The naked PSMA antibody was devoid of any anti-proliferation activity.

Figure 2:
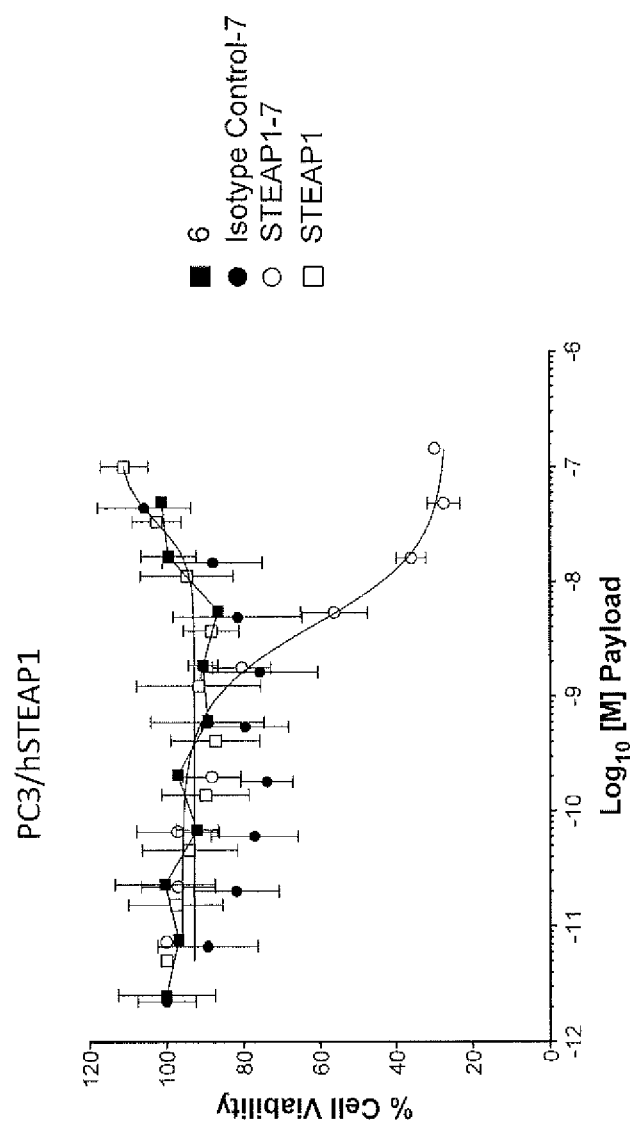

In PC3/hSTEAP1 cells (prostate cancer line), expressing hSTEAP1 at 352 fold above isotype control binding, the maytansinoid conjugate STEAP1-7 possesses an IC$_{50}$ value of 4 nM (FIG. 2). The naked STEAP1 antibody was devoid of any anti-proliferation activity.

Figure 3:
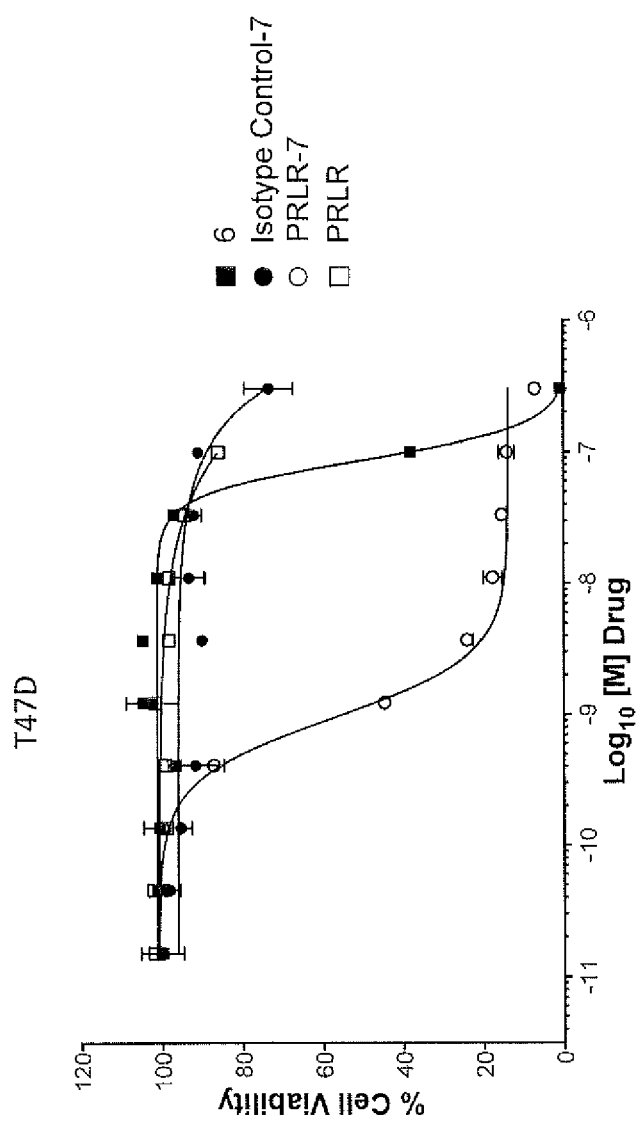

In T47D cells (breast cancer line), natively expressing PRLR at 14 fold above isotype control binding, the maytansinoid conjugate PRLR-7 possesses an IC$_{50}$ value of 1.0 nM (FIG. 3). The naked T47D antibody was devoid of any anti-proliferation activity.

Figure 4:
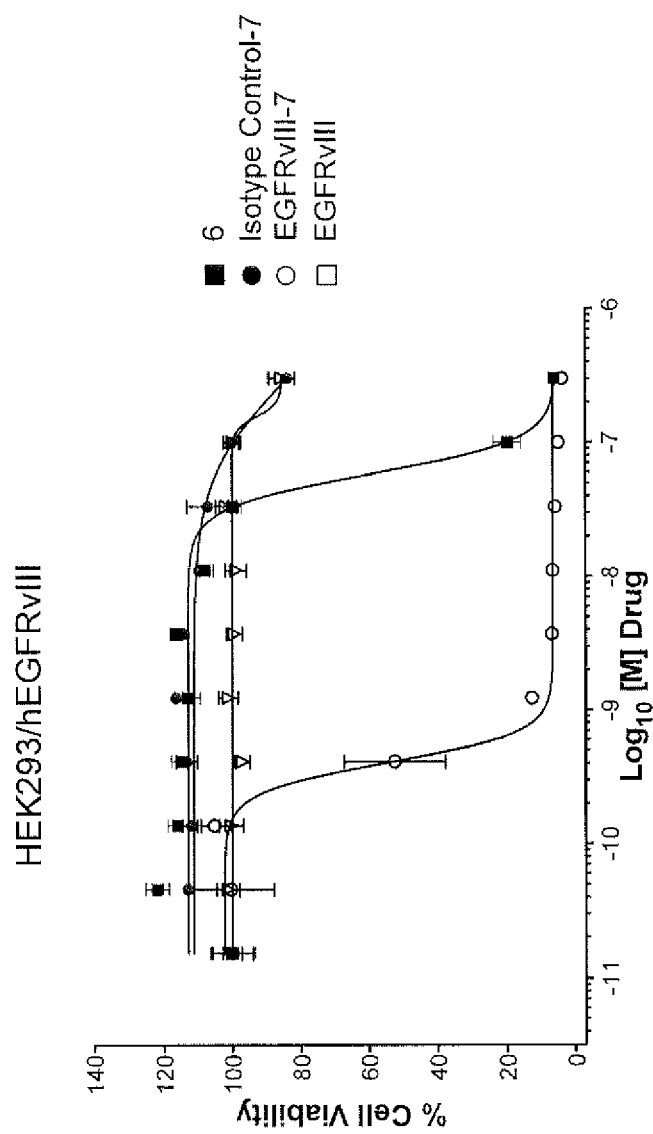

In HEK293/hEGFRvIII cells, expressing hEGFRvIII at 360 fold above isotype control binding, the maytansinoid conjugate EGFRvIII-7 possesses an IC$_{50}$ value of 0.4 nM (FIG. 4). The naked EGFRvIII antibody was devoid of any anti-proliferation activity.

Figure 5:
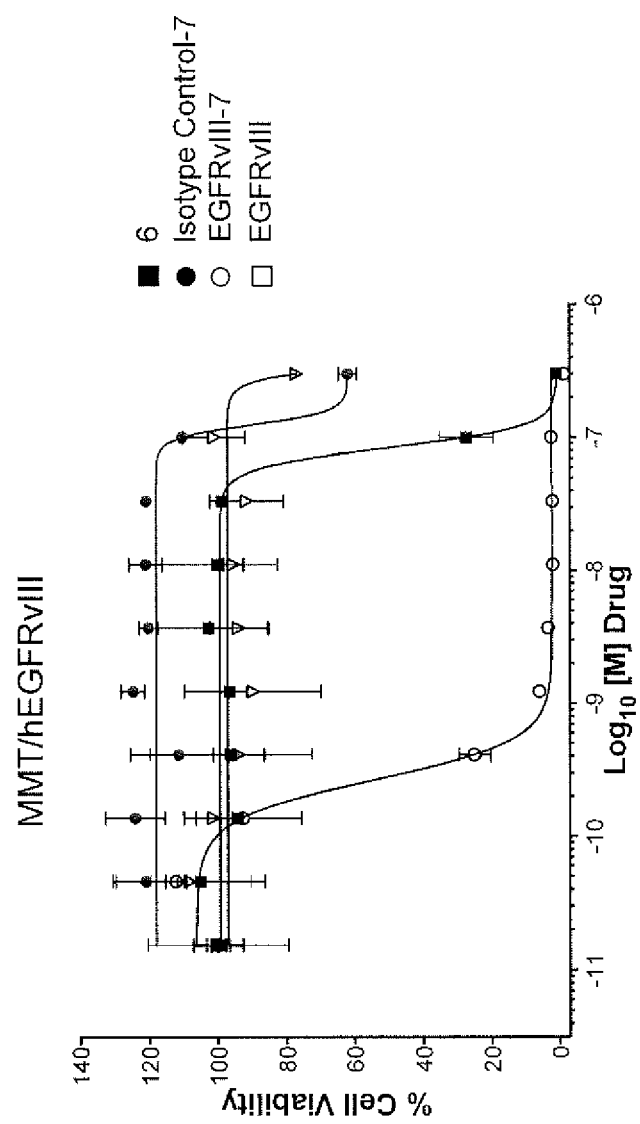

In MMT/hEGFRvIII cells, expressing hEGFRvIII at 280 fold above isotype control binding, the maytansinoid conjugate EGFRvIII-7 possesses an IC$_{50}$ value of 0.3 nM (FIG. 5). The naked EGFRvIII antibody was devoid of any anti-proliferation activity.

Figure 6:
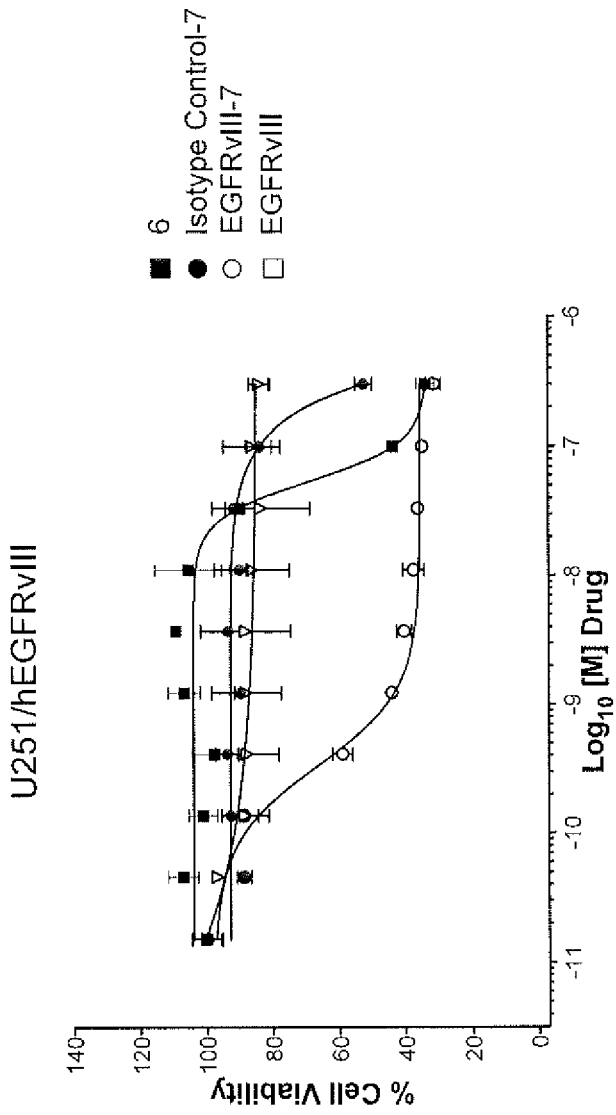

In U251/hEGFRvIII cells (glioblastoma cancer line), expressing hEGFRvIII at 165 fold above isotype control binding, the maytansinoid conjugate EGFRvIII-7 possesses an IC$_{50}$ value of 0.3 nM (FIG. 6). The naked EGFRvIII antibody was devoid of any anti-proliferation activity.

In vitro cytotoxicity of proposed released payloads ("free drugs") were also tested in the various cell lines described above and plotted along-side the conjugated antibodies for comparison (see closed squares (■) in FIGS. 1 to 6). For linker-payloads 3 and 7 the proposed released payloads 2 and 6, respectively, can be used in the cellular assays directly since they are stable. However, for linker-payload 21 the released payload is proposed to be the sulfhydryl compound 10. Since 10 could be a very reactive compound, which would lead to unreliable results, compound 25 was chosen to represent the released payload in these assays.

Figure 7:
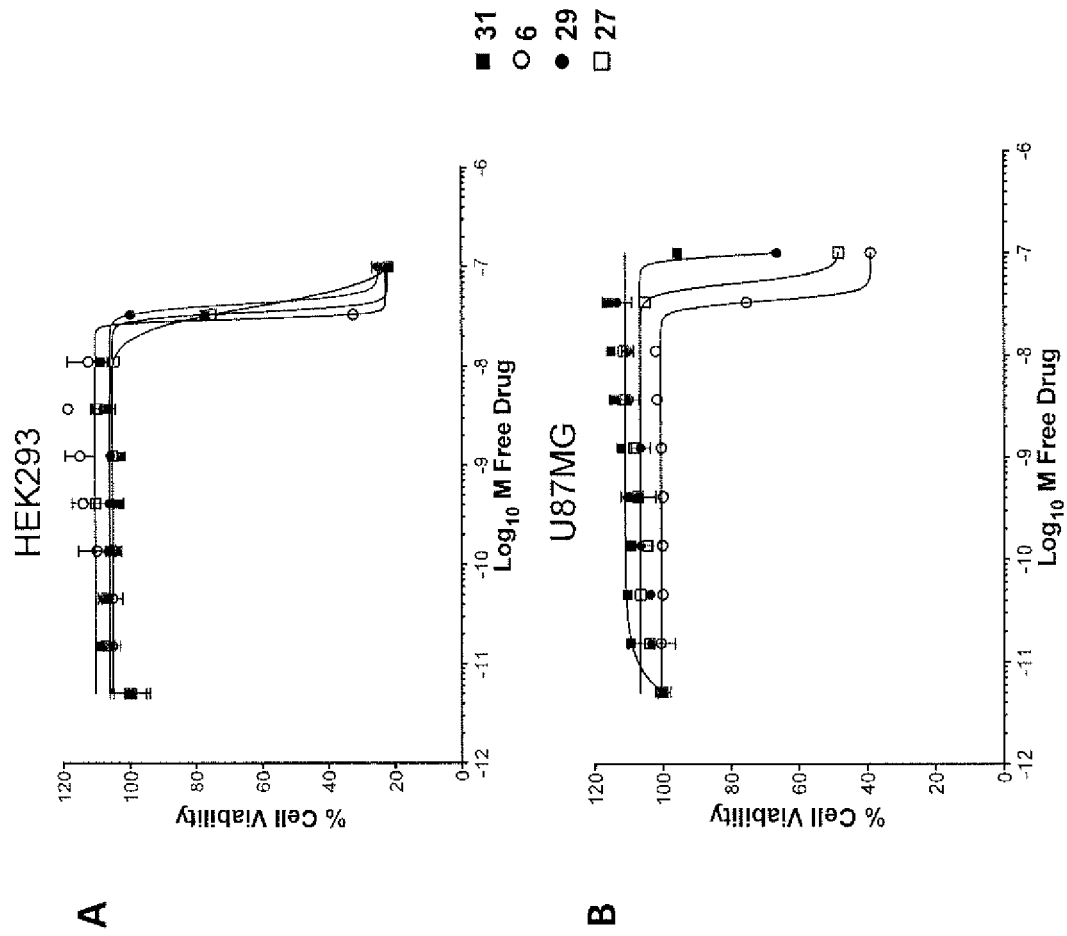

In a separate set of experiments, compound 6, along with amino analogs 27, 29, and 31 were assayed in HEK293 and U87MG for anti-proliferation activity (FIG. 7). These compounds all had >30 nM $IC_{50}$ values indicating that they are highly cytotoxic only when attached to an antibody via an appropriate linker. (For these experiments, background correction with digitonin was not performed).

Figure 8:
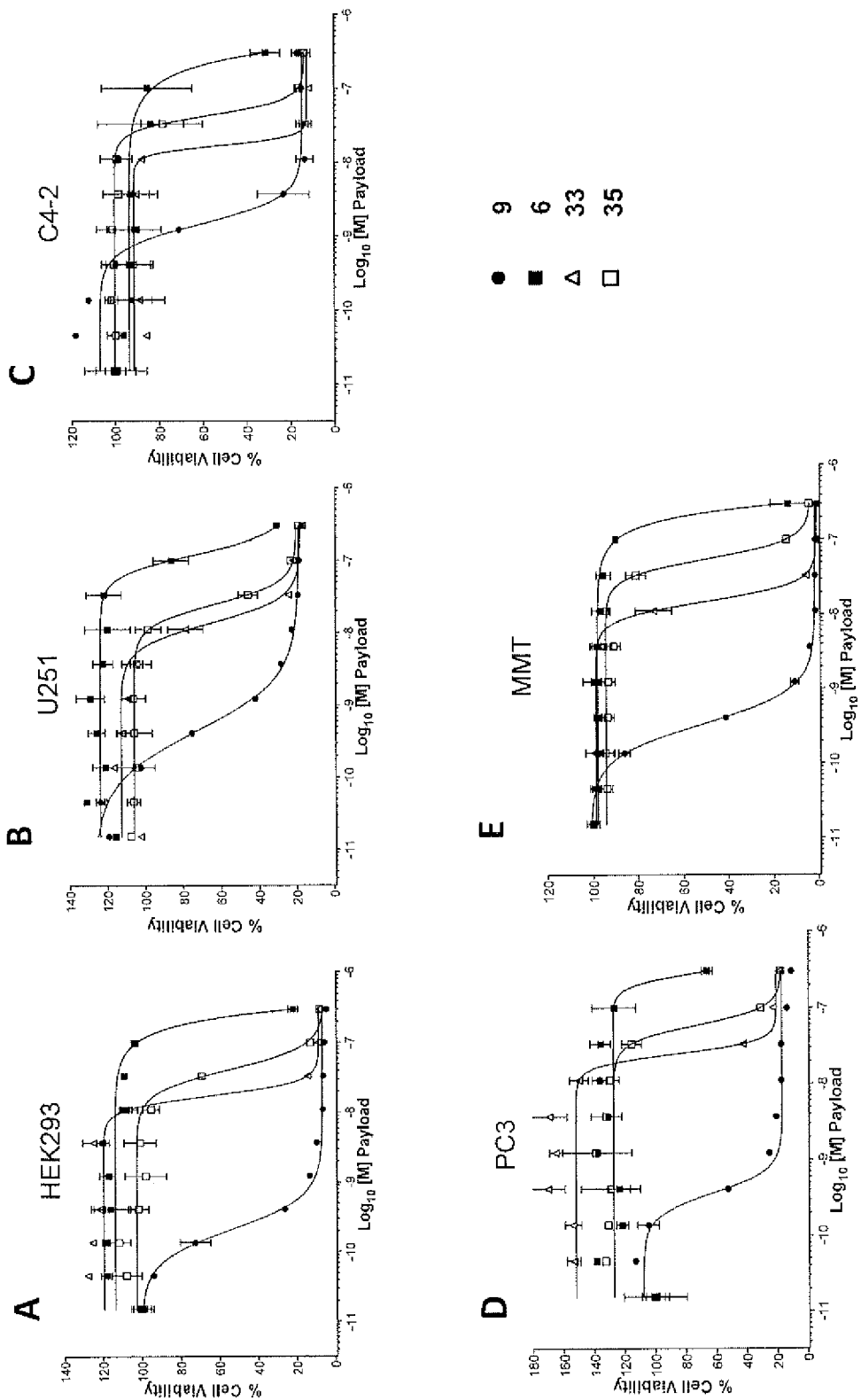

In yet another set of experiments, compounds 6, 9, 33, and 35 were assayed in HEK293, U251, C4-2, PC3, and MMT for anti-proliferation activity (FIG. 8). Amino compounds 6, 33, and 35 had varied $IC_{50}$s as listed in Table 2. The trend in potency follows 9>33>35>6 and is consistent for the 5 cell lines assayed.

TABLE 2

| Compound | $IC_{50}$ (nM) | | | | |
| --- | --- | --- | --- | --- | --- |
|  | HEK293 | U251 | C4-2 | PC3 | MMT |
| 9 | 0.2 | 0.4 | 1.5 | 0.4 | 0.3 |
| 33 | 20 | 15 | 20 | 30 | 20 |
| 35 | 50 | 25 | 55 | 65 | 60 |
| 6 | 200 | 150 | 200 | 250 | 250 |

Without being bound by any theory, the results of these experiments demonstrate that the "released" or "free drug" versions of the compounds of the present disclosure (i.e., the compounds not conjugated to an antibody) were, in most cases, substantially less cytotoxic than when conjugated to a targeting antibody. This feature of the present disclosure suggests that antibody-drug conjugates comprising the compounds of the invention will cause fewer side-effects and less unwanted toxicity since the cell killing properties will be concentrated at the site of the target antigen specifically.

Example 15

Anti-EGFRvIII Antibody Drug Conjugates are Potent Inhibitors of Tumor Growth in In Vivo EGFRvIII Positive Breast Cancer Allograft Models In this Example, two different antibody-drug conjugates of the exemplary anti-EGFRvIII antibody H1H1863N2 were tested for their ability to inhibit tumor growth in vivo. (The amino acid sequence and various properties of H1H1863N2 are set forth in U.S. 61/950,963, filed on Mar. 11, 2014, hereby incorporated by reference in its entirety). H1H1863N2 comprises a heavy chain variable region (HCVR) comprising SEQ ID NO:1; a light chain variable region (LCVR) comprising SEQ ID NO:5; heavy chain complementarity determining regions (HCDR1, HCDR2 and HCDR3) comprising SEQ ID NOs: 2, 3 and 4, respectively; and light chain complementarity determining regions (LCDR1, LCDR2 and LCDR3) comprising SEQ ID NOs: 6, 7 and 8, respectively.

A first ADC was produced by conjugating H1H1863N2 to the maytansinoid DM1 via a non-cleavable MCC linker (see, e.g., U.S. Pat. No. 5,208,020 and US application 20100129314) to produce "H1H1863N2-MCC-DM1." A second ADC was produced by conjugating H1H1863N2 to 7 to yield "H1H1863N2-7." When tested for cytotoxicity in vitro against MMT/EGFRvIII cells using the assay format described in Example 14, H1H1863N2-MCC-DM1 exhibited an $IC_{50}$ of 12 nM whereas H1H1863N2-7 exhibited an $IC_{50}$ of only 0.8 nM. Thus, in vitro, the anti-EGFRvIII ADC H1H1863N2-7 exhibited much more potent tumor cell killing ability than the corresponding antibody conjugated to DM1 via an MCC linker.

To compare the in vivo efficacy of the anti-EGFRvIII antibodies conjugated to MCC-DM1 and 7, studies were performed in immunocompromised mice bearing EGFRvIII positive breast cancer allografts. Briefly, tumor allografts were established by subcutaneous implantation of $0.5 \times 10^6$ MMT/EGFRvIII cells into the left flank of female CB17 SCID mice (Taconic, Hudson, NY). Once tumors had reached an average volume of 140 mm³ (~Day 8), mice were randomized into groups of seven, and dosed with anti-EGFRvIII ADCs using either the MCC-DM1 or 7 linker-drug format. Control reagents, including non-binding ADCs using either the MCC-DM1 or 7 linker-drug format, and PBS vehicle were also assessed. ADCs were dosed at 1 and 5 mg/kg three times over one week and thereafter monitored until an average tumor size of approximately 2000 mm³ was attained in the group administered with vehicle alone. At this point the Tumor Growth Inhibition was calculated.

Average tumor size relative to the vehicle treated group were calculated as follows: tumors were measured with calipers twice a week until the average size of the vehicle group reached 1000 mm³; tumor size was calculated using the formula (length×width²)/2. Tumor growth inhibition was calculated according to the following formula: $(1-((T_{final}-T_{initial})/(C_{final}-C_{initial})))*100$, where T (treated group) and C (control group) represent the mean tumor mass on the day the vehicle group reached 1000 mm³. Results are summarized in Table 3.

TABLE 3

Tumor Size and Tumor Growth Inhibition Following Administration of Anti-EGFRvIII Antibody-Drug Conjugates and Controls, administered in repeat dose

| Treatment Group | Final Tumor size at Day 8 mm³ (mean ± SD) | Average Tumor Growth Inhibition (%) |
| --- | --- | --- |
| PBS Vehicle | 2253 ± 217 | 0 |
| Control-MCC-DM1 (1 mg/kg) | 2827 ± 278 | −27 |
| Control-MCC-DM1 (5 mg/kg) | 2402 ± 256 | −7 |
| Control-7 (1 mg/kg) | 2729 ± 470 | −22 |
| Control-7 (5 mg/kg) | 2787 ± 503 | −25 |
| H1H1863N2-MCC-DM1 (1 mg/kg) | 931 ± 292 | 62 |
| H1H1863N2-MCC-DM1 (5 mg/kg) | 471 ± 227 | 84 |
| H1H1863N2-7 (1 mg/kg) | 679 ± 265 | 74 |
| H1H1863N2-7 (5 mg/kg) | 96 ± 34 | 102 |

As shown in this Example, the greatest tumor inhibition was observed in mice dosed with 5 mg/kg H1H1863N2-7, where regression of the initial tumor was observed. The tumor growth inhibition of 102% resulting from treatment with 5 mg/kg H1H1863N2-7 was significantly greater relative to that observed following treatment of tumor with 5 mg/kg H1H1862N2-MCC-DM1 (83%). The superiority of the tumor growth inhibition induced by H1H1863N2-7 compared to H1H1863N2-MCC-DM1 was maintained at the 1 mg/kg dose as well. No anti-tumor effect was observed in groups treated with Control ADC using MCC-DM1 or 7.

What is claimed is:

1. A method for reducing, retarding, or stopping an abnormal cell growth comprising contacting one or more cells growing abnormally with a compound, in an amount sufficient to retard, reduce, or stop the abnormal cell growth, and wherein the compound has the following formula

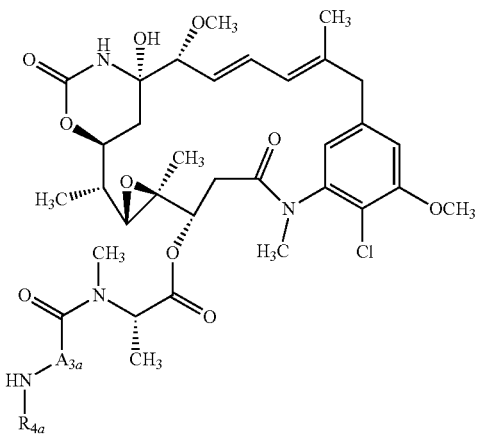

wherein $A_{3a}$ is —CH$_2$—, —CH$_2$CH$_2$—, or —CH$_2$CH$_2$CH$_2$CH$_2$—; and $R_{4a}$ is a substituted or unsubstituted alkyl, alkenyl, alkynyl, aryl, heteroaryl, or heterocyclyl.

2. The method of claim 1, wherein $A_{3a}$ is —CH$_2$CH$_2$—.

3. The method of claim 2, wherein $R_{4a}$ is a substituted or unsubstituted alkyl.

4. The method of claim 3, wherein the compound is

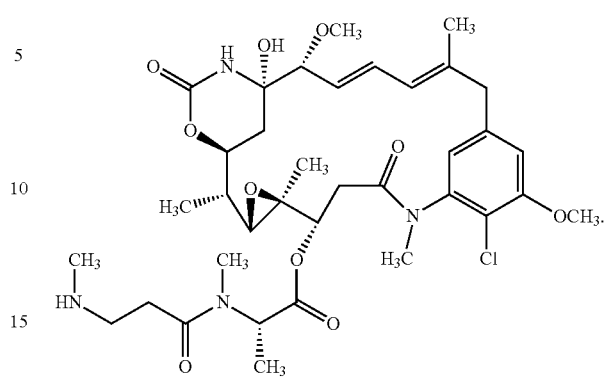

5. The method of claim 1, wherein the one or more cells growing abnormally is within a mammal.

6. The method of claim 1, wherein the one or more cells growing abnormally comprise a tumor cell.

7. The method of claim 1, wherein the one or more cells growing abnormally comprise a colon cancer cell.

8. The method of claim 1, wherein the one or more cells growing abnormally comprise a lung cancer cell.

9. The method of claim 1, wherein $A_3$ is —CH$_2$CH$_2$—.

10. The method of claim 1, further comprising administering sequentially or consecutively an additional therapy.

11. The method of claim 10, wherein the additional therapy is radiation therapy, chemotherapy, or a combination of both.

12. The method of claim 1, further comprising administering at least one additional therapeutic agent.

* * * * *

SEQUENCE LISTING

<160> NUMBER OF SEQ ID NOS: 8

<210> SEQ ID NO 1
<211> LENGTH: 122
<212> TYPE: PRT
<213> ORGANISM: Artificial Sequence
<220> FEATURE:
<223> OTHER INFORMATION: Synthetic

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Ala Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Asp Tyr Val Trp Gly Thr Tyr Arg Pro Leu Phe Asp Tyr Trp
            100                 105                 110

Gly Gln Gly Thr Leu Val Thr Val Ser Ser
        115                 120

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Gly Phe Pro Phe Ser Ser Tyr Asp
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3

Ile Gly Thr Ala Gly Ala Thr
1               5

<210> SEQ ID NO 4
<211> LENGTH: 16
<212> TYPE: PRT
<213> ORGANISM: Artificial Sequence
<220> FEATURE:
<223> OTHER INFORMATION: Synthetic

<400> SEQUENCE: 4

Ala Arg Gly Asp Tyr Val Trp Gly Thr Tyr Arg Pro Leu Phe Asp Tyr
1               5                   10                  15

<210> SEQ ID NO 5
<211> LENGTH: 107
<212> TYPE: PRT

<213> ORGANISM: Artificial Sequence
<220> FEATURE:
<223> OTHER INFORMATION: Synthetic

<400> SEQUENCE: 5

```
Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Asn Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105
```

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

```
Gln Gly Ile Asn Asn Tyr
1               5
```

<210> SEQ ID NO 7
<211> LENGTH: 3
<212> TYPE: PRT
<213> ORGANISM: Artificial Sequence
<220> FEATURE:
<223> OTHER INFORMATION: Synthetic

<400> SEQUENCE: 7

```
Ala Ala Ser
1
```

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

```
Gln Gln Leu Asn Ser Tyr Pro Leu Thr
1               5
```